(12) United States Patent
Baumhof

(10) Patent No.: US 10,799,602 B2
(45) Date of Patent: *Oct. 13, 2020

(54) METHOD FOR INCREASING EXPRESSION OF RNA-ENCODED PROTEINS

(71) Applicant: CureVac AG, Tübingen (DE)

(72) Inventor: Patrick Baumhof, Dusslingen (DE)

(73) Assignee: CureVac AG, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/371,304

(22) Filed: Apr. 1, 2019

(65) Prior Publication Data

US 2019/0216951 A1    Jul. 18, 2019

Related U.S. Application Data

(63) Continuation of application No. 15/048,031, filed on Feb. 19, 2016, now Pat. No. 10,293,060, which is a continuation of application No. PCT/EP2014/002300, filed on Aug. 21, 2014.

(51) Int. Cl.

| A61K 48/00 | (2006.01) |
|---|---|
| A61K 9/00 | (2006.01) |
| C07K 14/005 | (2006.01) |
| C07K 14/505 | (2006.01) |
| C12N 7/00 | (2006.01) |
| C12N 9/02 | (2006.01) |
| C12N 15/67 | (2006.01) |
| C12N 15/68 | (2006.01) |
| C12N 15/88 | (2006.01) |
| A61K 38/00 | (2006.01) |

(52) U.S. Cl.
CPC ........ *A61K 48/0075* (2013.01); *A61K 9/0021* (2013.01); *A61K 48/0066* (2013.01); *A61K 48/0083* (2013.01); *C07K 14/005* (2013.01); *C07K 14/505* (2013.01); *C12N 7/00* (2013.01); *C12N 9/0069* (2013.01); *C12N 15/67* (2013.01); *C12N 15/68* (2013.01); *C12N 15/88* (2013.01); *A61K 38/00* (2013.01); *C12N 2760/00034* (2013.01); *C12N 2760/20134* (2013.01); *C12Y 113/12007* (2013.01); *Y02A 50/402* (2018.01); *Y02A 50/415* (2018.01); *Y02A 50/423* (2018.01)

(58) Field of Classification Search
CPC .............. A61K 48/0075; A61K 9/0021; C07K 14/005; C07K 14/505; C12N 7/00; C12N 9/0021
See application file for complete search history.

(56) References Cited

U.S. PATENT DOCUMENTS

| 10,293,060 B2 * | 5/2019 | Baumhof ........... A61K 48/0075 |
|---|---|---|
| 2005/0032730 A1 | 2/2005 | Von der Mulbe et al. |
| 2005/0059624 A1 | 3/2005 | Hoerr et al. |
| 2005/0250723 A1 | 11/2005 | Hoerr et al. |
| 2006/0188490 A1 | 8/2006 | Hoerr et al. |
| 2008/0025944 A1 | 1/2008 | Hoerr et al. |
| 2008/0267873 A1 | 10/2008 | Hoerr et al. |
| 2009/0324584 A1 | 12/2009 | Hoerr et al. |
| 2010/0047261 A1 * | 2/2010 | Hoerr .................... A61K 39/00 424/184.1 |
| 2010/0048883 A1 | 2/2010 | Ketterer et al. |
| 2010/0189729 A1 | 7/2010 | Hoerr et al. |
| 2010/0203076 A1 | 8/2010 | Fotin-Mleczek et al. |
| 2010/0291156 A1 | 11/2010 | Barner et al. |
| 2010/0305196 A1 | 12/2010 | Probst et al. |
| 2011/0053829 A1 | 3/2011 | Baumhof et al. |
| 2011/0250225 A1 | 10/2011 | Fotin-Mleczek et al. |
| 2012/0021043 A1 | 1/2012 | Kramps et al. |
| 2012/0258046 A1 | 10/2012 | Mutzke |
| 2013/0129754 A1 | 5/2013 | Thess et al. |
| 2013/0142818 A1 | 6/2013 | Baumhof et al. |
| 2013/0259879 A1 | 10/2013 | Baumhof et al. |

(Continued)

FOREIGN PATENT DOCUMENTS

| CN | 101519449 | 9/2009 |
|---|---|---|
| EP | 2083851 | 8/2009 |

(Continued)

OTHER PUBLICATIONS

Holtkamp et al., "Modification of antigen-encoding RNA increases stability, translational efficacy, and T-cell stimulatory capacity of dendritic cells," *Blood*, 108(13):4009-4017, 2006.
Office Action issued in U.S. Appl. No. 15/048,031, dated Apr. 19, 2018.
Office Action issued in U.S. Appl. No. 15/048,031, dated Dec. 27, 2017.
Office Action issued in U.S. Appl. No. 15/048,031, dated Jan. 27, 2017.
Office Action issued in U.S. Appl. No. 15/048,031, dated Jun. 15, 2017.

(Continued)

*Primary Examiner* — Antonio Galisteo Gonzalez
(74) *Attorney, Agent, or Firm* — Parker Highlander PLLC

(57) ABSTRACT

The invention relates to an RNA comprising at least one open reading frame (ORF) and comprising at least one modification, which increases the expression of the encoded peptide or protein. Furthermore, the invention relates to the medical use of such a modified RNA administered to a subject by jet injection. The invention relates further to a pharmaceutical composition and to a kit of parts comprising said modified RNA for administration by jet injection, preferably for use in the field of gene therapy and/or genetic vaccination. Additionally, the invention relates to a method for enhancing the (localized) expression of RNA-encoded peptides or proteins in the dermis or muscle (of a mammal) comprising administering the modified RNA by jet injection. And finally, the invention relates to a method of treatment comprising administering the modified RNA by jet injection to a subject in need thereof.

20 Claims, 17 Drawing Sheets

Specification includes a Sequence Listing.

(56) References Cited

U.S. PATENT DOCUMENTS

| | | | |
|---|---|---|---|
| 2013/0259923 A1* | 10/2013 | Bancel | A61K 48/005 424/450 |
| 2013/0280283 A1 | 10/2013 | Lorenz et al. | |
| 2013/0295043 A1 | 11/2013 | Kallen et al. | |
| 2013/0336998 A1 | 12/2013 | Kallen et al. | |
| 2015/0037326 A1 | 2/2015 | Cutler-Ransofhoff et al. | |
| 2015/0050302 A1* | 2/2015 | Thess | C12N 15/67 424/185.1 |
| 2015/0057340 A1 | 2/2015 | Thess et al. | |
| 2015/0093413 A1 | 4/2015 | Thess et al. | |
| 2015/0118183 A1 | 4/2015 | Baumhof | |
| 2015/0118264 A1 | 4/2015 | Baumhof et al. | |
| 2015/0165006 A1 | 6/2015 | Thess et al. | |
| 2015/0184195 A1* | 7/2015 | Thess | C12N 15/67 424/185.1 |
| 2015/0218554 A1* | 8/2015 | Thess | C12N 15/67 424/184.1 |
| 2015/0306249 A1 | 10/2015 | Baumhof et al. | |
| 2015/0320847 A1 | 11/2015 | Thess et al. | |
| 2016/0130345 A1 | 5/2016 | Fotin-Mleczek et al. | |
| 2016/0166668 A1 | 6/2016 | Kallen et al. | |
| 2016/0166678 A1 | 6/2016 | Kallen et al. | |
| 2016/0166710 A1 | 6/2016 | Baumhof | |
| 2016/0166711 A1 | 6/2016 | Schnee et al. | |
| 2016/0168207 A1 | 6/2016 | Kramps et al. | |
| 2016/0168227 A1 | 6/2016 | Kallen et al. | |

FOREIGN PATENT DOCUMENTS

| | | |
|---|---|---|
| JP | 2008/507271 | 3/2008 |
| JP | 2010/508014 | 3/2010 |
| JP | 2012/509071 | 4/2012 |
| JP | 2013/501014 | 1/2013 |
| WO | WO 1999/014346 | 3/1999 |
| WO | WO 2002/098443 | 12/2002 |
| WO | WO 2006/022712 | 3/2006 |
| WO | WO 2008/052770 | 5/2008 |
| WO | WO 2010/057501 | 5/2010 |
| WO | WO 2011/015347 | 2/2011 |
| WO | WO 2012/019360 | 2/2012 |
| WO | WO 2013/143698 | 10/2013 |
| WO | WO 2013/143699 | 10/2013 |
| WO | WO 2013/143700 | 10/2013 |
| WO | WO 2015/062738 | 5/2015 |
| WO | WO 2015/101414 | 7/2015 |
| WO | WO 2015/101415 | 7/2015 |
| WO | WO 2015/101416 | 7/2015 |
| WO | WO 2015/135558 | 9/2015 |
| WO | WO 2015/149944 | 10/2015 |

OTHER PUBLICATIONS

PCT International Search Report and Written Opinion issued in International Application No. PCT/EP2014/002300, dated Nov. 14, 2014.

Stein et al., "Complete *in vivo* reversal of the multidrug resistance phenotype by jet-injection of anti-MDR1 short hairpin RNA-encoding plasmid DNA," *Molecular Therapy*, 16(1):178-186, 2008.

Villemjane et al., "Physical methods of nucleic acid transfer: general concepts and applications," *British Journal of Pharmacology*, 157(2):207-219, 2009.

\* cited by examiner

R1265: PpLuc(GC) – muag – A64 - C30 – histoneSL

GGGAGAAAGCUUGAGGAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAGACUAGUUAUA
AGACUGACUAGCCCGAUGGGCCUCCCAACGGGCCCUCCUCCCCUCCUUGCACCGAGAUUA
AUAAAAAAAAAAAAAAAAAAAAAAAAAAAAAAAAAAAAAAAAAAAAAAAAAAAAAAAAAA
AAAAAAUGCAUCCCCCCCCCCCCCCCCCCCCCCCCCCCCCCAAAGGCUCUUUUCAGAGC
CACCAGAAUU

Fig. 4

R2652: PpLuc(wt) – A30

GGGAGAAAGCUUACCAUGGAAGACGCCAAAAACAUAAAGAAAGGCCCGGCGCCAUUCUAU
CCUUUAGAGGAUGGAACCGCUGGAGAGCAACUGCAUAAGGCUAUGAAGAGAUACGCCCUG
GUUCCUGGAACAAUUGCUUUUACAGAUGCACAUAUCGAGGUGAACAUCACGUACGCGGAA
UACUUCGAAAUGUCCGUUCGGUUGGCAGAAGCUAUGAAACGAUAUGGGCUGAAUACAAAU
CACAGAAUCGUCGUAUGCAGUGAAAACUCUCUUCAAUUCUUUAUGCCGGUGUUGGGCGCG
UUAUUUAUCGGAGUUGCAGUUGCGCCCGCGAACGACAUUUAUAAUGAACGUGAAUUGCUC
AACAGUAUGAACAUUUCGCAGCCUACCGUAGUGUUUGUUUCCAAAAAGGGGUUGCAAAAA
AUUUUGAACGUGCAAAAAAAAUUACCAAUAAUCCAGAAAAUUAUUAUCAUGGAUUCUAAA
ACGGAUUACCAGGGAUUUCAGUCGAUGUACACGUUCGUCACAUCUCAUCUACCUCCCGGU
UUUAAUGAAUACGAUUUUGUACCAGAGUCCUUUGAUCGUGACAAAACAAUUGCACUGAUA
AUGAAUAGCUCUGGAUCUACGGGUUACCUAAGGGUGUGGCCCUUCCGCAUAGAACUGCC
UGCGUCAGAUUCUCGCAUGCCAGAGAUCCUAUUUUUGGCAAUCAAAUCAUUCCGGAUACU
GCGAUUUUAAGUGUUGUUCCAUUCCAUCACGGUUUUGGAAUGUUUACUACACUCGGAUAU
UUGAUAUGUGGAUUUCGAGUCGUCUUAAUGUAUAGAUUUGAAGAAGAGCUGUUUUUACGA
UCCCUUCAGGAUUACAAAAUUCAAAGUGCGUUGCUAGUACCAACCCUAUUUUCAUUCUUC
GCCAAAAGCACUCUGAUUGACAAAUACGAUUUAUCUAAUUUACACGAAAUUGCUUCUGGG
GGCGCACCUCUUUCGAAAGAAGUCGGGGAAGCGGUUGCAAAACGCUUCCAUCUUCCAGGG
AUACGACAAGGAUAUGGGCUCACUGAGACUACAUCAGCUAUUCUGAUUACACCCGAGGGG
GAUGAUAAACCGGGCGCGGUCGGUAAAGUUGUUCCAUUUUUUGAAGCGAAGGUUGUGGAU
CUGGAUACCGGGAAAACGCUGGGCGUUAAUCAGAGAGGCGAAUUAUGUGUCAGAGGACCU
AUGAUUAUGUCCGGUUAUGUAAACAAUCCGGAAGCGACCAACGCCUUGAUUGACAAGGAU
GGAUGGCUACAUUCUGGAGACAUAGCUUACUGGGACGAAGACGAACACUUCUUCAUAGUU
GACCGCUUGAAGUCUUUAAUUAAAUACAAAGGAUAUCAGGUGGCCCCCGCUGAAUUGGAA
UCGAUAUUGUUACAACACCCCAACAUCUUCGACGCGGGCGUGGCAGGUCUUCCCGACGAU
GACGCCGGUGAACUUCCCGCCGCCGUUGUUGUUUGGAGCACGGAAAGACGAUGACGGAA
AAAGAGAUCGUGGAUUACGUCGCCAGUCAAGUAACAACCGCGAAAAGUUGCGCGGAGGA
GUUGUGUUUGUGGACGAAGUACCGAAAGGUCUUACCGGAAAACUCGACGCAAGAAAAAUC
AGAGAGAUCCUCAUAAAGGCCAAGAAGGGCGGAAAGUCCAAAUUGUGAGGACUAGUAGAU
CUAAAAAAAAAAAAAAAAAAAAAAAAAAAAAA

Fig. 5

R3454: PpLuc(wt) – A64

GGGAGAAAGCUUACCAUGGAAGACGCCAAAAACAUAAAGAAAGGCCCGGCGCCAUUCUAU
CCUUUAGAGGAUGGAACCGCUGGAGAGCAACUGCAUAAGGCUAUGAAGAGAUACGCCCUG
GUUCCUGGAACAAUUGCUUUUACAGAUGCACAUAUCGAGGUGAACAUCACGUACGCGGAA
UACUUCGAAAUGUCCGUUCGGUUGGCAGAAGCUAUGAAACGAUAUGGGCUGAAUACAAAU
CACAGAAUCGUCGUAUGCAGUGAAAACUCUCUUCAAUUCUUUAUGCCGGUGUUGGGCGCG
UUAUUUAUCGGAGUUGCAGUUGCGCCCGCGAACGACAUUUAUAAUGAACGUGAAUUGCUC
AACAGUAUGAACAUUCGCAGCCUACCGUAGUGUUUGUUUCCAAAAGGGGUUGCAAAAA
AUUUUGAACGUGCAAAAAAAUUACCAAUAAUCCAGAAAAUUAUUAUCAUGGAUUCUAAA
ACGGAUUACCAGGGAUUUCAGUCGAUGUACACGUUCGUCACAUCUCAUCUACCUCCCGGU
UUUAAUGAAUACGAUUUUGUACCAGAGUCCUUUGAUCGUGACAAAACAAUUGCACUGAUA
AUGAAUAGCUCUGGAUCUACGGGUUACCUAAGGGUGUGGCCCUUCCGCAUAGAACUGCC
UGCGUCAGAUUCUCGCAUGCCAGAGAUCCUAUUUUUGGCAAUCAAAUCAUUCCGGAUACU
GCGAUUUUAAGUGUUGUUCCAUUCCAUCACGGUUUUGGAAUGUUUACUACACUCGGAUAU
UUGAUAUGUGGAUUUCGAGUCGUCUUAAUGUAUAGAUUUGAAGAAGAGCUGUUUUUACGA
UCCCUUCAGGAUUACAAAAUUCAAAGUGCGUUGCUAGUACCAACCCUAUUUUCAUUCUUC
GCCAAAAGCACUCUGAUUGACAAAUACGAUUUAUCUAAUUUACACGAAAUUGCUUCUGGG
GGCGCACCUCUUUCGAAAGAAGUCGGGGAAGCGGUUGCAAAACGCUUCCAUCUUCCAGGG
AUACGACAAGGAUAUGGGCUCACUGAGACUACAUCAGCUAUUCUGAUUACACCCGAGGGG
GAUGAUAAACCGGGCGCGGUCGGUAAAGUUGUUCCAUUUUUUGAAGCGAAGGUUGUGGAU
CUGGAUACCGGGAAAACGCUGGGCGUUAAUCAGAGAGGCGAAUUAUGUGUCAGAGGACCU
AUGAUUAUGUCCGGUUAUGUAAACAAUCCGGAAGCGACCAACGCCUUGAUUGACAAGGAU
GGAUGGCUACAUUCUGGAGACAUAGCUUACUGGGACGAAGACGAACACUUCUUCAUAGUU
GACCGCUUGAAGUCUUUAAUUAAAUACAAAGGAUAUCAGGUGGCCCCCGCUGAAUUGGAA
UCGAUAUUGUUACAACACCCCAACAUCUUCGACGCGGGCGUGGCAGGUCUUCCCGACGAU
GACGCCGGUGAACUUCCCGCCGCCGUUGUUGUUUUGGAGCACGGAAAGACGAUGACGGAA
AAAGAGAUCGUGGAUUACGUCGCCAGUCAAGUAACAACCGCGAAAAAGUUGCGCGGAGGA
GUUGUGUUUGUGGACGAAGUACCGAAAGGUCUUACCGGAAAACUCGACGCAAGAAAAAUC
AGAGAGAUCCUCAUAAAGGCCAAGAAGGGCGGAAAGUCCAAAUUGUGAGGACUAGUAGAU
CUAAAAAAAAAAAAAAAAAAAAAAAAAAAAAAAAAAAAAAAAAAAAAAAAAAAAAAAAAAAAAA
AAAAAA

Fig. 6

R2462: PpLuc(GC)-A64-C30-HistoneSL

GGGAGAAAGCUUGAGGAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAGACUAGUAGAU
CUAAAAAAAAAAAAAAAAAAAAAAAAAAAAAAAAAAAAAAAAAAAAAAAAAAAAAAAAAA
AAAAAAUGCAUCCCCCCCCCCCCCCCCCCCCCCCCCCCCCCAAAGGCUCUUUUCAGAGC
CACCAGAAUU

Fig. 7

R1256: PpLuc(GC)-muag-A64-C30

GGGAGAAAGCUUGAGGAUGGAGGACGCCAAGAACAUCAAGAAGGGCCCGGCGCCCUUCUA
CCCGCUGGAGGACGGGACCGCCGGCGAGCAGCUCCACAAGGCCAUGAAGCGGUACGCCCU
GGUGCCGGGCACGAUCGCCUUCACCGACGCCCACAUCGAGGUCGACAUCACCUACGCGGA
GUACUUCGAGAUGAGCGUGCGCCUGGCCGAGGCCAUGAAGCGGUACGGCCUGAACACCAA
CCACCGGAUCGUGGUGUGCUCGGAGAACAGCCUGCAGUUCUUCAUGCCGGUGCUGGGCGC
CCUCUUCAUCGGCGUGGCCGUCGCCCCGGCGAACGACAUCUACAACGAGCGGGAGCUGCU
GAACAGCAUGGGGAUCAGCCAGCCGACCGUGGUGUUCGUGAGCAAGAAGGGCCUGCAGAA
GAUCCUGAACGUGCAGAAGAAGCUGCCCAUCAUCCAGAAGAUCAUCAUCAUGGACAGCAA
GACCGACUACCAGGGCUUCCAGUCGAUGUACACGUUCGUGACCAGCCACCUCCCGCCGGG
CUUCAACGAGUACGACUUCGUCCCGGAGAGCUUCGACCGGGACAAGACCAUCGCCCUGAU
CAUGAACAGCAGCGGCAGCACCGGCCUGCCGAAGGGGGUGGCCCUGCCGCACCGGACCGC
CUGCGUGCGCUUCUCGCACGCCCGGGACCCCAUCUUCGGCAACCAGAUCAUCCCGGACAC
CGCCAUCCUGAGCGUGGUGCCGUUCCACCACGGCUUCGGCAUGUUCACGACCCUGGGCUA
CCUCAUCUGCGGCUUCCGGGUGGUCCUGAUGUACCGGUUCGAGGAGGAGCUGUUCCUGCG
GAGCCUGCAGGACUACAAGAUCCAGAGCGCGCUGCUCGUGCCGACCCUGUUCAGCUUCUU
CGCCAAGAGCACCCUGAUCGACAAGUACGACCUGUCGAACCUGCACGAGAUCGCCAGCGG
GGGCGCCCCGCUGAGCAAGGAGGUGGGCGAGGCCGUGGCCAAGCGGUUCCACCUCCCGGG
CAUCCGCCAGGGCUACGGCCUGACCGAGACCACGAGCGCGAUCCUGAUCACCCCCGAGGG
GGACGACAAGCCGGGCGCCGUGGGCAAGGUGGUCCCGUUCUUCGAGGCCAAGGUGGUGGA
CCUGGACACCGGCAAGACCCUGGGCGUGAACCAGCGGGGCGAGCUGUGCGUGCGGGGGCC
GAUGAUCAUGAGCGGCUACGUGAACAACCCGGAGGCCACCAACGCCCUCAUCGACAAGGA
CGGCUGGCUGCACAGCGGCGACAUCGCCUACUGGGACGAGGACGAGCACUUCUUCAUCGU
CGACCGGCUGAAGUCGCUGAUCAAGUACAAGGGCUACCAGGUGGCGCCGGCCGAGCUGGA
GAGCAUCCUGCUCCAGCACCCCAACAUCUUCGACGCCGGCGUGGCCGGGCUGCCGGACGA
CGACGCCGGCGAGCUGCCGGCCGCGGUGGUGGUGCUGGAGCACGGCAAGACCAUGACGGA
GAAGGAGAUCGUCGACUACGUGGCCAGCCAGGUGACCACCGCCAAGAAGCUGCGGGGCGG
CGUGGUGUUCGUGGACGAGGUCCCGAAGGGCCUGACCGGGAAGCUCGACGCCCGGAAGAU
CCGCGAGAUCCUGAUCAAGGCCAAGAAGGGCGGCAAGAUCGCCGUGUAAGACUAGUUAUA
AGACUGACUAGCCCGAUGGGCCUCCCAACGGGCCCUCCUCCCCUCCUUGCACCGAGAUUA
AUAAAAAAAAAAAAAAAAAAAAAAAAAAAAAAAAAAAAAAAAAAAAAAAAAAAAAAAAAA
AAAAAAUGCAUCCCCCCCCCCCCCCCCCCCCCCCCCCCCCCCUCUAG

Fig. 8

R2393: PpLuc(nat)-muag-A64-C30-HistoneSL

GGGAGAAAGCUUACCAUGGAAGACGCCAAAAACAUAAAGAAAGGCCCGGCGCCAUUCUAU
CCUUUAGAGGAUGGAACCGCUGGAGAGCAACUGCAUAAGGCUAUGAAGAGAUACGCCCUG
GUUCCUGGAACAAUUGCUUUUACAGAUGCACAUAUCGAGGUGAACAUCACGUACGCGGAA
UACUUCGAAAUGUCCGUUCGGUUGGCAGAAGCUAUGAAACGAUAUGGGCUGAAUACAAAU
CACAGAAUCGUCGUAUGCAGUGAAAACUCUCUUCAAUUCUUUAUGCCGGUGUUGGGCGCG
UUAUUUAUCGGAGUUGCAGUUGCGCCCGCGAACGACAUUUAUAAUGAACGUGAAUUGCUC
AACAGUAUGAACAUUUCGCAGCCUACCGUAGUGUUUGUUUCCAAAAAGGGGUUGCAAAAA
AUUUUGAACGUGCAAAAAAAAUUACCAAUAAUCCAGAAAAUUAUUAUCAUGGAUUCUAAA
ACGGAUUACCAGGGAUUUCAGUCGAUGUACACGUUCGUCACAUCUCAUCUACCUCCCGGU
UUUAAUGAAUACGAUUUUGUACCAGAGUCCUUUGAUCGUGACAAAACAAUUGCACUGAUA
AUGAAUAGCUCUGGAUCUACUGGGUUACCUAAGGGUGUGGCCCUUCCGCAUAGAACUGCC
UGCGUCAGAUUCUCGCAUGCCAGAGAUCCUAUUUUUGGCAAUCAAAUCAUUCCGGAUACU
GCGAUUUUAAGUGUUGUUCCAUUCCAUCACGGUUUUGGAAUGUUUACUACACUCGGAUAU
UUGAUAUGUGGAUUUCGAGUCGUCUUAAUGUAUAGAUUUGAAGAAGAGCUGUUUUUACGA
UCCCUUCAGGAUUACAAAAUUCAAAGUGCGUUGCUAGUACCAACCCUAUUUUCAUUCUUC
GCCAAAAGCACUCUGAUUGACAAAUACGAUUUAUCUAAUUUACACGAAAUUGCUUCUGGG
GGCGCACCUCUUUCGAAAGAAGUCGGGGAAGCGGUUGCAAAACGCUUCCAUCUUCCAGGG
AUACGACAAGGAUAUGGGCUCACUGAGACUACAUCAGCUAUUCUGAUUACACCCGAGGGG
GAUGAUAAACCGGGCGCGGUCGGUAAAGUUGUUCCAUUUUUUGAAGCGAAGGUUGUGGAU
CUGGAUACCGGGAAAACGCUGGGCGUUAAUCAGAGAGGCGAAUUAUGUGUCAGAGGACCU
AUGAUUAUGUCCGGUUAUGUAAACAAUCCGGAAGCGACCAACGCCUUGAUUGACAAGGAU
GGAUGGCUACAUUCUGGAGACAUAGCUUACUGGGACGAAGACGAACACUUCUUCAUAGUU
GACCGCUUGAAGUCUUUAAUUAAAUACAAAGGAUAUCAGGUGGCCCCCGCUGAAUUGGAA
UCGAUAUUGUUACAACACCCCAACAUCUUCGACGCGGGCGUGGCAGGUCUUCCCGACGAU
GACGCCGGUGAACUUCCCGCCGCCGUUGUUGUUUGGAGCACGGAAAGACGAUGACGGAA
AAAGAGAUCGUGGAUUACGUCGCCAGUCAAGUAACAACCGCGAAAAGUUGCGCGGAGGA
GUUGUGUUUGUGGACGAAGUACCGAAAGGUCUUACCGGAAAACUCGACGCAAGAAAAAUC
AGAGAGAUCCUCAUAAAGGCCAAGAAGGGCGGAAAGUCCAAAUUGUGAGGACUAGUUAUA
AGACUGACUAGCCCGAUGGGCCUCCCAACGGGCCCUCCUCCCCUCCUUGCACCGAGAUUA
AUAAAAAAAAAAAAAAAAAAAAAAAAAAAAAAAAAAAAAAAAAAAAAAAAAAAAAAAAAA
AAAAAAUGCAUCCCCCCCCCCCCCCCCCCCCCCCCCCCCCCAAAGGCUCUUUUCAGAGC
CACCAGAAUU

Fig. 9

R2403: RAV-G(GC)-muag-A64-C30-histoneSL

GGGAGAAAGCUUACCAUGGUGCCCCAGGCCCUGCUCUUCGUCCCGCUGCUGGUGUUCCCC
CUCUGCUUCGGCAAGUUCCCCAUCUACACCAUCCCCGACAAGCUGGGGCCGUGGAGCCCC
AUCGACAUCCACCACCUGUCCUGCCCCAACAACCUCGUGGUCGAGGACGAGGGCUGCACC
AACCUGAGCGGGUUCUCCUACAUGGAGCUGAAGGUGGGCUACAUCAGCGCCAUCAAGAUG
AACGGGUUCACGUGCACCGGCGUGGUCACCGAGGCGGAGACCUACACGAACUUCGUGGGC
UACGUGACCACCACCUUCAAGCGGAAGCACUUCCGCCCCACGCCGGACGCCUGCCGGGCC
GCCUACAACUGGAAGAUGGCCGGGGACCCCCGCUACGAGGAGUCCUCCACAACCCCUAC
CCCGACUACCACUGGCUGCGGACCGUCAAGACCACCAAGGAGAGCCUGGUGAUCAUCUCC
CCGAGCGUGGCGGACCUCGACCCCUACGACCGCUCCCUGCACAGCCGGGUCUUCCCCGGC
GGGAACUGCUCCGGCGUGGCCGUGAGCUCCACGUACUGCAGCACCAACCACGACUACACC
AUCUGGAUGCCCGAGAACCCGCGCCUGGGGAUGUCCUGCGACAUCUUCACCAACAGCCGG
GGCAAGCGCGCCUCCAAGGGCAGCGAGACGUGCGGGUUCGUCGACGAGCGGGGCCUCUAC
AAGUCCCUGAAGGGGGCCUGCAAGCUGAAGCUCUGCGGCGUGCUGGGCCUGCGCCUCAUG
GACGGGACCUGGGUGGCGAUGCAGACCAGCAACGAGACCAAGUGGUGCCCCCCGGCCAG
CUGGUCAACCUGCACGACUUCCGGAGCGACGAGAUCGAGCACCUCGUGGUGGAGGAGCUG
GUCAAGAAGCGCGAGGAGUGCCUGGACGCCCUCGAGUCCAUCAUGACGACCAAGAGCGUG
UCCUUCCGGCGCCUGAGCCACCUGCGGAAGCUCGUGCCCGGGUUCGGCAAGGCCUACACC
AUCUUCAACAAGACCCUGAUGGAGGCCGACGCCCACUACAAGUCCGUCCGCACGUGGAAC
GAGAUCAUCCCGAGCAAGGGGUGCCUGCGGGUGGCGGCCGCUGCCACCCCCACGUCAAC
GGGGUGUUCUUCAACGGCAUCAUCCUCGGGCCCGACGGCAACGUGCUGAUCCCCGAGAUG
CAGUCCAGCCUGCUCCAGCAGCACAUGGAGCUGCUGGUCUCCAGCGUGAUCCCGCUCAUG
CACCCCCUGGCGGACCCCUCCACCGUGUUCAAGAACGGGGACGAGGCCGAGGACUUCGUC
GAGGUGCACCUGCCCGACGUGCACGAGCGGAUCAGCGGCGUCGACCUCGGCCUGCCGAAC
UGGGGGAAGUACGUGCUGCUCUCCGCCGGCGCCCUGACCGCCCUGAUGCUGAUCAUCUUC
CUCAUGACCUGCUGGCGCCGGGUGAACCGGAGCGAGCCCACGCAGCACAACCUGCGCGGG
ACCGGCCGGGAGGUCUCCGUGACCCCGCAGAGCGGGAAGAUCAUCUCCAGCUGGGAGUCC
UACAAGAGCGGCGGCGAGACCGGGCUGUGAGGACUAGUUAUAAGACUGACUAGCCCGAUG
GGCCUCCCAACGGGCCCUCCUCCCCUCCUUGCACCGAGAUUAAUAAAAAAAAAAAAAAAA
AAAAAAAAAAAAAAAAAAAAAAAAAAAAAAAAAAAAAAAAAAAAAAAAUGCAUCCCCCCC
CCCCCCCCCCCCCCCCCCCCCCCAAAGGCUCUUUUCAGAGCCACCAGAAUU

Fig. 10

R3513: EPO (wt)-A30

GGGAGAAAGCUUACCAUGGGGGUGCCCGAACGUCCCACCCUGCUGCUUUUACUCUCCUUG
CUACUGAUUCCUCUGGGCCUCCCAGUCCUCUGUGCUCCCCCACGCCUCAUCUGCGACAGU
CGAGUUCUGGAGAGGUACAUCUUAGAGGCCAAGGAGGCAGAAAAUGUCACGAUGGGUUGU
GCAGAAGGUCCCAGACUGAGUGAAAAUAUUACAGUCCCAGAUACCAAAGUCAACUUCUAU
GCUUGGAAAGAAUGGAGGUGGAAGAACAGGCCAUAGAAGUUUGGCAAGGCCUGUCCCUG
CUCUCAGAAGCCAUCCUGCAGGCCCAGGCCCUGCUAGCCAAUUCCUCCCAGCCACCAGAG
ACCCUUCAGCUUCAUAUAGACAAAGCCAUCAGUGGUCUACGUAGCCUCACUUCACUGCUU
CGGGUACUGGGAGCUCAGAAGGAAUUGAUGUCGCCUCCAGAUACCACCCCACCUGCUCCA
CUCCGAACACUCACAGUGGAUACUUUCUGCAAGCUCUUCCGGGUCUACGCCAACUUCCUC
CGGGGGAAACUGAAGCUGUACACGGGAGAGGUCUGCAGGAGAGGGGACAGGUGACCACUA
GUAGAUCUAAAAAAAAAAAAAAAAAAAAAAAAAAAAAA

Fig. 11

R3135: HSD17B4-EPO (GC)-albumin7-A64-C30-histoneSL

GGGUCCCGCAGUCGGCGUCCAGCGGCUCUGCUUGUUCGUGUGUGUGUCGUUGCAGGCCUU
AUUCAAGCUUACCAUGGGCGUGCCCGAGCGGCCGACCCUGCUCCUGCUGCUCAGCCUGCU
GCUCAUCCCCUGGGGCUGCCCGUCCUCUGCGCCCCCCGCGCCUGAUCUGCGACUCCCG
GGUGCUGGAGCGCUACAUCCUCGAGGCCAAGGAGGCGGAGAACGUGACCAUGGGCUGCGC
CGAGGGGCCCCGGCUGAGCGAGAACAUCACGGUCCCCGACACCAAGGUGAACUUCUACGC
CUGGAAGCGCAUGGAGGUGGAGGAGCAGGCCAUCGAGGUCUGGCAGGGCCUGUCCCUCCU
GAGCGAGGCCAUCCUGCAGGCGCAGGCCCUCCUGGCCAACUCCAGCCAGCCCCGGAGAC
ACUGCAGCUCCACAUCGACAAGGCCAUCUCCGGGCUGCGGAGCCUGACCUCCCUCCUGCG
CGUGCUGGGCGCGCAGAAGGAGCUCAUGAGCCCGCCCGACACGACCCCCCCGGCCCCGCU
GCGGACCCUGACCGUGGACACGUUCUGCAAGCUCUUCCGCGUCUACGCCAACUUCCUGCG
GGGCAAGCUGAAGCUCUACACCGGGGAGGUGUGCCGCCGGGGCGACCGCUGACCACUAGU
GCAUCACAUUUAAAAGCAUCUCAGCCUACCAUGAGAAUAAGAGAAAGAAAAUGAAGAUCA
AUAGCUUAUUCAUCUCUUUUUCUUUUUCGUUGGUGUAAAGCCAACACCCUGUCUAAAAAA
CAUAAAUUUCUUUAAUCAUUUUGCCUCUUUUCUCUGUGCUUCAAUUAAUAAAAAAUGGAA
AGAACCUAGAUCUAAAAAAAAAAAAAAAAAAAAAAAAAAAAAAAAAAAAAAAAAAAAAAA
AAAAAAAAAAAAAAAAAAAUGCAUCCCCCCCCCCCCCCCCCCCCCCCCCCCCAAAGGCU
CUUUUCAGAGCCACCAGAAUU

Fig. 12

RSV-F long (GC) R2510

GGGGCGCUGCCUACGGAGGUGGCAGCCAUCUCCUUCUCGGCAUCAAGCUUACCAUGGAGC
UGCCCAUCCUCAAGGCCAACGCCAUCACCACCAUCCUGGCGGCCGUGACGUUCUGCUUCG
CCAGCUCCCAGAACAUCACCGAGGAGUUCUACCAGAGCACCUGCUCCGCCGUCAGCAAGG
GCUACCUGUCCGCCCUCCGGACCGGGUGGUACACGAGCGUGAUCACCAUCGAGCUGUCCA
ACAUCAAGGAGAACAAGUGCAACGGCACCGACGCGAAGGUGAAGCUGAUCAACCAGGAGC
UCGACAAGUACAAGAACGCCGUCACCGAGCUGCAGCUGCUCAUGCAGAGCACGACCGCCG
CCAACAACCGCGCGCGGCGCGAGCUGCCGCGGUUCAUGAACUACACCCUGAACAACACCA
AGAAGACGAACGUGACCCUCUCCAAGAAGCGCAAGCGGCGCUUCCUGGGGUUCCUGCUCG
GCGUGGGGAGCGCCAUCGCCUCCGGCAUCGCCGUCAGCAAGGUGCUGCACCUGGAGGGCG
AGGUGAACAAGAUCAAGUCCGCCCUCCUGAGCACCAACAAGGCGGUCGUGUCCCUGAGCA
ACGGGGUGUCCGUCCUCACCAGCAAGGUGCUGGACCUGAAGAACUACAUCGACAAGCAGC
UCCUGCCCAUCGUGAACAAGCAGUCCUGCCGGAUCAGCAACAUCGAGACGGUCAUCGAGU
UCCAGCAGAAGAACAACCGCCUGCUCGAGAUCACCCGGGAGUUCAGCGUGAACGCCGGCG
UGACCACCCCCGUCUCCACGUACAUGCUGACCAACAGCGAGCUGCUCUCCCUGAUCAACG
ACAUGCCCAUCACCAACGACCAGAAGAAGCUGAUGAGCAACAACGUGCAGAUCGUGCGCC
AGCAGUCCUACAGCAUCAUGUCCAUCAUCAAGGAGGAGGUCCUCGCCUACGUGGUGCAGC
UGCCGCUGUACGGGGUCAUCGACACCCCCUGCUGGAAGCUCCACACGAGCCCCCUGUGCA
CCACCAACACCAAGGAGGGCUCCAACAUCUGCCUGACGCGGACCGACCGCGGGUGGUACU
GCGACAACGCCGGCAGCGUGUCCUUCUUCCCCCAGGCCGAGACCUGCAAGGUCCAGAGCA
ACCGGGUGUUCUGCGACACCAUGAACUCCCUCACGCUGCCGAGCGAGGUGAACCUGUGCA
ACGUCGACAUCUUCAACCCCAAGUACGACUGCAAGAUCAUGACCUCCAAGACCGACGUGA
GCUCCAGCGUGAUCACCUCCCUCGGCGCGAUCGUCAGCUGCUACGGGAAGACGAAGUGCA
CCGCCAGCAACAAGAACCGCGGCAUCAUCAAGACCUUCUCCAACGGGUGCGACUACGUGA
GCAACAAGGGCGUGGACACCGUCUCCGUGGGCAACACCCUGUACUACGUGAACAAGCAGG
AGGGGAAGAGCCUGUACGUCAAGGGCGAGCCCAUCAUCAACUUCUACGACCCCCUCGUGU
UCCCGUCCGACGAGUUCGACGCCAGCAUCUCCCAGGUGAACGAGAAGAUCAACCAGAGCC
UGGCCUUCAUCCGGAAGUCCGACGAGCUGCUGCACCACGUCAACGCCGGGAAGAGCACGA
CCAACAUCAUGAUCACCACCAUCAUCAUCGUGAUCAUCGUGAUCCUCCUGUCCCUGAUCG
CGGUCGGCCUCCUGCUGUACUGCAAGGCCCGCAGCACGCCCGUGACCCUCUCCAAGGACC
AGCUGAGCGGGAUCAACAACAUCGCCUUCUCCAACUGAGGACUAGUGCAUCACAUUUAAA
AGCAUCUCAGCCUACCAUGAGAAUAAGAGAAAGAAAAUGAAGAUCAAUAGCUUAUUCAUC
UCUUUUUCUUUUUCGUUGGUGUAAAGCCAACACCCUGUCUAAAAAACAUAAAUUUCUUUA
AUCAUUUUGCCUCUUUUCUCUGUGCUUCAAUUAAUAAAAAAUGGAAAGAACCUAGAUCUA
AAAAAAAAAAAAAAAAAAAAAAAAAAAAAAAAAAAAAAAAAAAAAAAAAAAAAAAAAAAA
AAAUGCAUCCCCCCCCCCCCCCCCCCCCCCCCCCCCCCCAAAGGCUCUUUUCAGAGCCAC
CAGAAUU

SEQUENCE LISTING

```
<160> NUMBER OF SEQ ID NOS: 64

<210> SEQ ID NO 1
<211> LENGTH: 16
<212> TYPE: RNA
<213> ORGANISM: Artificial Sequence
<220> FEATURE:
<223> OTHER INFORMATION: Sequence according to formula (Ic)
<220> FEATURE:
<221> NAME/KEY: misc_feature
<222> LOCATION: (1)..(1)
<223> OTHER INFORMATION: n is a, u, t, g, and c, or a nucleotide
      analogue thereof
<220> FEATURE:
<221> NAME/KEY: misc_feature
<222> LOCATION: (3)..(8)
<223> OTHER INFORMATION: n is a, u, t, g, and c, or a nucleotide
      analogue thereof
<220> FEATURE:
<221> NAME/KEY: misc_feature
<222> LOCATION: (10)..(14)
<223> OTHER INFORMATION: n is a, u, t, g, and c, or a nucleotide
      analogue thereof
<220> FEATURE:
<221> NAME/KEY: misc_feature
<222> LOCATION: (16)..(16)
<223> OTHER INFORMATION: n is a, u, t, g, and c, or a nucleotide
      analogue thereof

<400> SEQUENCE: 1
ngnnnnnnun nnnncn                                                      16

<210> SEQ ID NO 2
<211> LENGTH: 26
<212> TYPE: RNA
<213> ORGANISM: Artificial Sequence
<220> FEATURE:
<223> OTHER INFORMATION: Sequence according to formula (IIc)
<220> FEATURE:
<221> NAME/KEY: misc_feature
<222> LOCATION: (1)..(2)
<223> OTHER INFORMATION: n is a, u, t, g, and c, or a nucleotide
      analogue thereof; may be
      present or not
<220> FEATURE:
<221> NAME/KEY: misc_feature
<222> LOCATION: (3)..(6)
<223> OTHER INFORMATION: n is a, u, t, g, and c, or a nucleotide
      analogue thereof
<220> FEATURE:
<221> NAME/KEY: misc_feature
<222> LOCATION: (8)..(13)
<223> OTHER INFORMATION: n is a, u, t, g, and c, or a nucleotide
      analogue thereof
<220> FEATURE:
<221> NAME/KEY: misc_feature
<222> LOCATION: (15)..(19)
<223> OTHER INFORMATION: n is a, u, t, g, and c, or a nucleotide
      analogue thereof
<220> FEATURE:
<221> NAME/KEY: misc_feature
<222> LOCATION: (21)..(24)
<223> OTHER INFORMATION: n is a, u, t, g, and c, or a nucleotide
```

```
    analogue thereof
<220> FEATURE:
<221> NAME/KEY: misc_feature
<222> LOCATION: (25)..(26)
<223> OTHER INFORMATION: n is a, u, t, g, and c, or a nucleotide
      analogue thereof; may be
      present or not.

<400> SEQUENCE: 2
nnnnnngnnn nnnunnnnnc nnnnnn                                              26

<210> SEQ ID NO 3
<211> LENGTH: 16
<212> TYPE: RNA
<213> ORGANISM: Artificial Sequence
<220> FEATURE:
<223> OTHER INFORMATION: Sequence according to formula (Id)
<220> FEATURE:
<221> NAME/KEY: misc_feature
<222> LOCATION: (1)..(1)
<223> OTHER INFORMATION: n is a, u, t, g, and c, or a nucleotide
      analogue thereof
<220> FEATURE:
<221> NAME/KEY: misc_feature
<222> LOCATION: (3)..(8)
<223> OTHER INFORMATION: n is a, u, t, g, and c, or a nucleotide
      analogue thereof
<220> FEATURE:
<221> NAME/KEY: misc_feature
<222> LOCATION: (10)..(14)
<223> OTHER INFORMATION: n is a, u, t, g, and c, or a nucleotide
      analogue thereof
<220> FEATURE:
<221> NAME/KEY: misc_feature
<222> LOCATION: (16)..(16)
<223> OTHER INFORMATION: n is a, u, t, g, and c, or a nucleotide
      analogue thereof

<400> SEQUENCE: 3
ncnnnnnnun nnnngn                                                         16

<210> SEQ ID NO 4
<211> LENGTH: 26
<212> TYPE: RNA
<213> ORGANISM: Artificial Sequence
<220> FEATURE:
<223> OTHER INFORMATION: Sequence according to formula (IId)
<220> FEATURE:
<221> NAME/KEY: misc_feature
<222> LOCATION: (1)..(2)
<223> OTHER INFORMATION: n is a, u, t, g, and c, or a nucleotide
      analogue thereof; may be
      present or not.
<220> FEATURE:
<221> NAME/KEY: misc_feature
<222> LOCATION: (3)..(6)
<223> OTHER INFORMATION: n is a, u, t, g, and c, or a nucleotide
      analogue thereof
<220> FEATURE:
<221> NAME/KEY: misc_feature
<222> LOCATION: (8)..(13)
<223> OTHER INFORMATION: n is a, u, t, g, and c, or a nucleotide
      analogue thereof
<220> FEATURE:
<221> NAME/KEY: misc_feature
<222> LOCATION: (15)..(19)
<223> OTHER INFORMATION: n is a, u, t, g, and c, or a nucleotide
      analogue thereof
<220> FEATURE:
<221> NAME/KEY: misc_feature
<222> LOCATION: (21)..(23)
<223> OTHER INFORMATION: n is a, u, t, g, and c, or a nucleotide
      analogue thereof
<220> FEATURE:
<221> NAME/KEY: misc_feature
```

```
<222> LOCATION: (24)..(26)
<223> OTHER INFORMATION: n is a, u, t, g, and c, or a nucleotide
      analogue thereof; may be
      present or not

<400> SEQUENCE: 4
nnnnnncnnn nnnunnnnng nnnnnn                                          26

<210> SEQ ID NO 5
<211> LENGTH: 16
<212> TYPE: RNA
<213> ORGANISM: Artificial Sequence
<220> FEATURE:
<223> OTHER INFORMATION: Sequence according to formula (Ie)
<220> FEATURE:
<221> NAME/KEY: misc_feature
<222> LOCATION: (3)..(8)
<223> OTHER INFORMATION: n is a, u, t, g, and c, or a nucleotide
      analogue thereof
<220> FEATURE:
<221> NAME/KEY: misc_feature
<222> LOCATION: (10)..(14)
<223> OTHER INFORMATION: n is a, u, t, g, and c, or a nucleotide
      analogue thereof

<400> SEQUENCE: 5
dgnnnnnnun nnnnch                                                     16

<210> SEQ ID NO 6
<211> LENGTH: 26
<212> TYPE: RNA
<213> ORGANISM: Artificial Sequence
<220> FEATURE:
<223> OTHER INFORMATION: Sequence according to formula (IIe)
<220> FEATURE:
<221> NAME/KEY: misc_feature
<222> LOCATION: (1)..(2)
<223> OTHER INFORMATION: n is a, u, t, g, and c, or a nucleotide
      analogue thereof; may be
      present or not
<220> FEATURE:
<221> NAME/KEY: misc_feature
<222> LOCATION: (3)..(5)
<223> OTHER INFORMATION: n is a, u, t, g, and c, or a nucleotide
      analogue thereof
<220> FEATURE:
<221> NAME/KEY: misc_feature
<222> LOCATION: (8)..(13)
<223> OTHER INFORMATION: n is a, u, t, g, and c, or a nucleotide
      analogue thereof
<220> FEATURE:
<221> NAME/KEY: misc_feature
<222> LOCATION: (15)..(19)
<223> OTHER INFORMATION: n is a, u, t, g, and c, or a nucleotide
      analogue thereof
<220> FEATURE:
<221> NAME/KEY: misc_feature
<222> LOCATION: (22)..(23)
<223> OTHER INFORMATION: n is a, u, t, g, and c, or a nucleotide
      analogue thereof
<220> FEATURE:
<221> NAME/KEY: misc_feature
<222> LOCATION: (24)..(26)
<223> OTHER INFORMATION: n is a, u, t, g, and c, or a nucleotide
      analogue thereof; may be
      present or not

<400> SEQUENCE: 6
nnnnndgnnn nnnunnnnnc hnnnnn                                          26

<210> SEQ ID NO 7
<211> LENGTH: 16
<212> TYPE: RNA
```

```
<213> ORGANISM: Artificial Sequence
<220> FEATURE:
<223> OTHER INFORMATION: Sequence according to formula (If)
<220> FEATURE:
<221> NAME/KEY: misc_feature
<222> LOCATION: (1)..(1)
<223> OTHER INFORMATION: n is a, u, t, g, and c, or a nucleotide
      analogue thereof
<220> FEATURE:
<221> NAME/KEY: misc_feature
<222> LOCATION: (3)..(3)
<223> OTHER INFORMATION: n is a, u, t, g, and c, or a nucleotide
      analogue thereof
<220> FEATURE:
<221> NAME/KEY: misc_feature
<222> LOCATION: (7)..(8)
<223> OTHER INFORMATION: n is a, u, t, g, and c, or a nucleotide
      analogue thereof
<220> FEATURE:
<221> NAME/KEY: misc_feature
<222> LOCATION: (10)..(10)
<223> OTHER INFORMATION: n is a, u, t, g, and c, or a nucleotide
      analogue thereof
<220> FEATURE:
<221> NAME/KEY: misc_feature
<222> LOCATION: (12)..(12)
<223> OTHER INFORMATION: n is a, u, t, g, and c, or a nucleotide
      analogue thereof
<220> FEATURE:
<221> NAME/KEY: misc_feature
<222> LOCATION: (14)..(14)
<223> OTHER INFORMATION: n is a, u, t, g, and c, or a nucleotide
      analogue thereof
<220> FEATURE:
<221> NAME/KEY: misc_feature
<222> LOCATION: (16)..(16)
<223> OTHER INFORMATION: n is a, u, t, g, and c, or a nucleotide
analogue thereof

<400> SEQUENCE: 7
ngnbyynnun vndncn                                                       16

<210> SEQ ID NO 8
<211> LENGTH: 26
<212> TYPE: RNA
<213> ORGANISM: Artificial Sequence
<220> FEATURE:
<223> OTHER INFORMATION: Sequence according to formula (IIf)
<220> FEATURE:
<221> NAME/KEY: misc_feature
<222> LOCATION: (1)..(2)
<223> OTHER INFORMATION: n is a, u, t, g, and c, or a nucleotide
      analogue thereof; may be present or not
<220> FEATURE:
<221> NAME/KEY: misc_feature
<222> LOCATION: (3)..(6)
<223> OTHER INFORMATION: n is a, u, t, g, and c, or a nucleotide
      analogue thereof
<220> FEATURE:
<221> NAME/KEY: misc_feature
<222> LOCATION: (8)..(8)
<223> OTHER INFORMATION: n is a, u, t, g, and c, or a nucleotide
      analogue thereof
<220> FEATURE:
<221> NAME/KEY: misc_feature
<222> LOCATION: (12)..(13)
<223> OTHER INFORMATION: n is a, u, t, g, and c, or a nucleotide
      analogue thereof
<220> FEATURE:
<221> NAME/KEY: misc_feature
<222> LOCATION: (15)..(15)
<223> OTHER INFORMATION: n is a, u, t, g, and c, or a nucleotide
      analogue thereof
<220> FEATURE:
<221> NAME/KEY: misc_feature
<222> LOCATION: (17)..(17)
<223> OTHER INFORMATION: n is a, u, t, g, and c, or a nucleotide
```

```
      analogue thereof
<220> FEATURE:
<221> NAME/KEY: misc_feature
<222> LOCATION: (19)..(19)
<223> OTHER INFORMATION: n is a, u, t, g, and c, or a nucleotide
      analogue thereof
<220> FEATURE:
<221> NAME/KEY: misc_feature
<222> LOCATION: (21)..(23)
<223> OTHER INFORMATION: n is a, u, t, g, and c, or a nucleotide
      analogue thereof
<220> FEATURE:
<221> NAME/KEY: misc_feature
<222> LOCATION: (24)..(26)
<223> OTHER INFORMATION: n is a, u, t, g, and c, or a nucleotide
      analogue thereof; may be present or not

<400> SEQUENCE: 8
nnnnnngnby ynnunvndnc nnnnnn                                          26

<210> SEQ ID NO 9
<211> LENGTH: 16
<212> TYPE: RNA
<213> ORGANISM: Artificial Sequence
<220> FEATURE:
<223> OTHER INFORMATION: Sequence according to formula (Ig)
<220> FEATURE:
<221> NAME/KEY: misc_feature
<222> LOCATION: (1)..(1)
<223> OTHER INFORMATION: n is a, u, t, g, and c, or a nucleotide
      analogue thereof
<220> FEATURE:
<221> NAME/KEY: misc_feature
<222> LOCATION: (8)..(8)
<223> OTHER INFORMATION: n is a, u, t, g, and c, or a nucleotide
      analogue thereof
<220> FEATURE:
<221> NAME/KEY: misc_feature
<222> LOCATION: (16)..(16)
<223> OTHER INFORMATION: n is a, u, t, g, and c, or a nucleotide
      analogue thereof

<400> SEQUENCE: 9
nghyyydnuh abrdcn                                                     16

<210> SEQ ID NO 10
<211> LENGTH: 26
<212> TYPE: RNA
<213> ORGANISM: Artificial Sequence
<220> FEATURE:
<223> OTHER INFORMATION: Sequence according to formula (IIg)
<220> FEATURE:
<221> NAME/KEY: misc_feature
<222> LOCATION: (1)..(2)
<223> OTHER INFORMATION: n is a, u, t, g, and c, or a nucleotide
      analogue thereof; may be present or not
<220> FEATURE:
<221> NAME/KEY: misc_feature
<222> LOCATION: (4)..(6)
<223> OTHER INFORMATION: n is a, u, t, g, and c, or a nucleotide
      analogue thereof
<220> FEATURE:
<221> NAME/KEY: misc_feature
<222> LOCATION: (13)..(13)
<223> OTHER INFORMATION: n is a, u, t, g, and c, or a nucleotide
      analogue thereof
<220> FEATURE:
<221> NAME/KEY: misc_feature
<222> LOCATION: (21)..(23)
<223> OTHER INFORMATION: n is a, u, t, g, and c, or a nucleotide
      analogue thereof
<220> FEATURE:
<221> NAME/KEY: misc_feature
<222> LOCATION: (24)..(25)
<223> OTHER INFORMATION: n is a, u, t, g, and c, or a nucleotide
```

```
                         analogue thereof; may be present or not
<220> FEATURE:
<221> NAME/KEY: misc_feature
<222> LOCATION: (26)..(26)
<223> OTHER INFORMATION: may be present or not

<400> SEQUENCE: 10
nnhnnnghyy ydnuhabrdc nnnnnh                                        26

<210> SEQ ID NO 11
<211> LENGTH: 16
<212> TYPE: RNA
<213> ORGANISM: Artificial Sequence
<220> FEATURE:
<223> OTHER INFORMATION: Sequence according to formula (Ih)

<400> SEQUENCE: 11
dghycudyuh asrrcc                                                   16

<210> SEQ ID NO 12
<211> LENGTH: 26
<212> TYPE: RNA
<213> ORGANISM: Artificial Sequence
<220> FEATURE:
<223> OTHER INFORMATION: Sequence according to formula (IIh)
<220> FEATURE:
<221> NAME/KEY: misc_feature
<222> LOCATION: (1)..(1)
<223> OTHER INFORMATION: n is a, u, t, g, and c, or a nucleotide
                         analogue thereof; may be present or not
<220> FEATURE:
<221> NAME/KEY: misc_feature
<222> LOCATION: (2)..(2)
<223> OTHER INFORMATION: may be present or not
<220> FEATURE:
<221> NAME/KEY: misc_feature
<222> LOCATION: (25)..(25)
<223> OTHER INFORMATION: n is a, u, t, g, and c, or a nucleotide
                         analogue thereof; may be present or not
<220> FEATURE:
<221> NAME/KEY: misc_feature
<222> LOCATION: (26)..(26)
<223> OTHER INFORMATION: may be present or not

<400> SEQUENCE: 12
nhaahdghyc udyuhasrrc cvhbnh                                        26

<210> SEQ ID NO 13
<211> LENGTH: 16
<212> TYPE: DNA
<213> ORGANISM: Artificial Sequence
<220> FEATURE:
<223> OTHER INFORMATION: Sequence according to formula (Ic)

<400> SEQUENCE: 13
vgyyyyhhth rvvrcb                                                   16

<210> SEQ ID NO 14
<211> LENGTH: 16
<212> TYPE: DNA
<213> ORGANISM: Artificial Sequence
<220> FEATURE:
<223> OTHER INFORMATION: Sequence according to formula (Ic)

<400> SEQUENCE: 14
sgyyyttytm arrrcs                                                   16

<210> SEQ ID NO 15
<211> LENGTH: 16
```

```
<212> TYPE: DNA
<213> ORGANISM: Artificial Sequence
<220> FEATURE:
<223> OTHER INFORMATION: Sequence according to formula (Ic)

<400> SEQUENCE: 15
sgyycttttm agrrcs                                                16

<210> SEQ ID NO 16
<211> LENGTH: 16
<212> TYPE: DNA
<213> ORGANISM: Artificial Sequence
<220> FEATURE:
<223> OTHER INFORMATION: Sequence according to formula (Ie)
<220> FEATURE:
<221> NAME/KEY: misc_feature
<222> LOCATION: (3)..(5)
<223> OTHER INFORMATION: n is a, u, t, g, and c, or a nucleotide
      analogue thereof
<220> FEATURE:
<221> NAME/KEY: misc_feature
<222> LOCATION: (7)..(8)
<223> OTHER INFORMATION: n is a, u, t, g, and c, or a nucleotide
      analogue thereof
<220> FEATURE:
<221> NAME/KEY: misc_feature
<222> LOCATION: (12)..(14)
<223> OTHER INFORMATION: n is a, u, t, g, and c, or a nucleotide
      analogue thereof

<400> SEQUENCE: 16
dgnnnbnnth vnnnch                                                16

<210> SEQ ID NO 17
<211> LENGTH: 16
<212> TYPE: DNA
<213> ORGANISM: Artificial Sequence
<220> FEATURE:
<223> OTHER INFORMATION: Sequence according to formula (Ie)
<220> FEATURE:
<221> NAME/KEY: misc_feature
<222> LOCATION: (3)..(5)
<223> OTHER INFORMATION: n is a, u, t, g, and c, or a nucleotide
      analogue thereof
<220> FEATURE:
<221> NAME/KEY: misc_feature
<222> LOCATION: (13)..(14)
<223> OTHER INFORMATION: n is a, u, t, g, and c, or a nucleotide
      analogue thereof

<400> SEQUENCE: 17
rgnnnyhbth rdnncy                                                16

<210> SEQ ID NO 18
<211> LENGTH: 16
<212> TYPE: DNA
<213> ORGANISM: Artificial Sequence
<220> FEATURE:
<223> OTHER INFORMATION: Sequence according to formula (Ie)
<220> FEATURE:
<221> NAME/KEY: misc_feature
<222> LOCATION: (3)..(3)
<223> OTHER INFORMATION: n is a, u, t, g, and c, or a nucleotide
      analogue thereof
<220> FEATURE:
<221> NAME/KEY: misc_feature
<222> LOCATION: (14)..(14)
<223> OTHER INFORMATION: n is a, u, t, g, and c, or a nucleotide
      analogue thereof

<400> SEQUENCE: 18
rgndbyhyth rdhncy                                                16
```

```
<210> SEQ ID NO 19
<211> LENGTH: 16
<212> TYPE: DNA
<213> ORGANISM: Artificial Sequence
<220> FEATURE:
<223> OTHER INFORMATION: Sequence according to formula (If)

<400> SEQUENCE: 19
vgyyytyhth rvrrcb                                                16

<210> SEQ ID NO 20
<211> LENGTH: 16
<212> TYPE: DNA
<213> ORGANISM: Artificial Sequence
<220> FEATURE:
<223> OTHER INFORMATION: Sequence according to formula (If)

<400> SEQUENCE: 20
sgyycttytm agrrcs                                                16

<210> SEQ ID NO 21
<211> LENGTH: 16
<212> TYPE: DNA
<213> ORGANISM: Artificial Sequence
<220> FEATURE:
<223> OTHER INFORMATION: Sequence according to formula (If)

<400> SEQUENCE: 21
sgyycttttm agrrcs                                                16

<210> SEQ ID NO 22
<211> LENGTH: 16
<212> TYPE: DNA
<213> ORGANISM: Artificial Sequence
<220> FEATURE:
<223> OTHER INFORMATION: Sequence according to formula (Ig)

<400> SEQUENCE: 22
ggyycttyth agrrcc                                                16

<210> SEQ ID NO 23
<211> LENGTH: 16
<212> TYPE: DNA
<213> ORGANISM: Artificial Sequence
<220> FEATURE:
<223> OTHER INFORMATION: Sequence according to formula (Ig)

<400> SEQUENCE: 23
ggcycttytm agrgcc                                                16

<210> SEQ ID NO 24
<211> LENGTH: 16
<212> TYPE: DNA
<213> ORGANISM: Artificial Sequence
<220> FEATURE:
<223> OTHER INFORMATION: Sequence according to formula (Ig)

<400> SEQUENCE: 24
ggctcttttm agrgcc                                                16

<210> SEQ ID NO 25
<211> LENGTH: 16
<212> TYPE: DNA
<213> ORGANISM: Artificial Sequence
<220> FEATURE:
```

<223> OTHER INFORMATION: Sequence according to formula (Ih)

<400> SEQUENCE: 25
dghyctdyth asrrcc 16

<210> SEQ ID NO 26
<211> LENGTH: 16
<212> TYPE: DNA
<213> ORGANISM: Artificial Sequence
<220> FEATURE:
<223> OTHER INFORMATION: Sequence according to formula (Ih)

<400> SEQUENCE: 26
ggcyctttth agrgcc 16

<210> SEQ ID NO 27
<211> LENGTH: 16
<212> TYPE: DNA
<213> ORGANISM: Artificial Sequence
<220> FEATURE:
<223> OTHER INFORMATION: Sequence according to formula (Ih)

<400> SEQUENCE: 27
ggcycttttm agrgcc 16

<210> SEQ ID NO 28
<211> LENGTH: 26
<212> TYPE: DNA
<213> ORGANISM: Artificial Sequence
<220> FEATURE:
<223> OTHER INFORMATION: Sequence according to formula (IIc)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (25)..(26)
<223> OTHER INFORMATION: n is a, u, t, g, and c, or a nucleotide
analogue thereof; may be present or not

<400> SEQUENCE: 28
hhhhvvgyyy yhhthrvvrc bvhhnn 26

<210> SEQ ID NO 29
<211> LENGTH: 26
<212> TYPE: DNA
<213> ORGANISM: Artificial Sequence
<220> FEATURE:
<223> OTHER INFORMATION: Sequence according to formula (IIc)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (25)..(26)
<223> OTHER INFORMATION: may be present or not

<400> SEQUENCE: 29
mhmhmsgyyy ttytmarrrc smchhh 26

<210> SEQ ID NO 30
<211> LENGTH: 26
<212> TYPE: DNA
<213> ORGANISM: Artificial Sequence
<220> FEATURE:
<223> OTHER INFORMATION: Sequence according to formula (IIc)
<220> FEATURE:

<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (25)..(26)
<223> OTHER INFORMATION: may be present or not

<400> SEQUENCE: 30
mmmmmsgyyc ttttmagrrc sachmh                                    26

<210> SEQ ID NO 31
<211> LENGTH: 26
<212> TYPE: DNA
<213> ORGANISM: Artificial Sequence
<220> FEATURE:
<223> OTHER INFORMATION: Sequence according to formula (IIe)
<220> FEATURE:
<221> NAME/KEY: misc_feature
<222> LOCATION: (1)..(2)
<223> OTHER INFORMATION: n is a, u, t, g, and c, or a nucleotide
      analogue thereof; may be present or not
<220> FEATURE:
<221> NAME/KEY: misc_feature
<222> LOCATION: (3)..(5)
<223> OTHER INFORMATION: n is a, u, t, g, and c, or a nucleotide
      analogue thereof
<220> FEATURE:
<221> NAME/KEY: misc_feature
<222> LOCATION: (8)..(10)
<223> OTHER INFORMATION: n is a, u, t, g, and c, or a nucleotide
      analogue thereof
<220> FEATURE:
<221> NAME/KEY: misc_feature
<222> LOCATION: (12)..(13)
<223> OTHER INFORMATION: n is a, u, t, g, and c, or a nucleotide
      analogue thereof
<220> FEATURE:
<221> NAME/KEY: misc_feature
<222> LOCATION: (17)..(19)
<223> OTHER INFORMATION: n is a, u, t, g, and c, or a nucleotide
      analogue thereof
<220> FEATURE:
<221> NAME/KEY: misc_feature
<222> LOCATION: (22)..(22)
<223> OTHER INFORMATION: n is a, u, t, g, and c, or a nucleotide
      analogue thereof
<220> FEATURE:
<221> NAME/KEY: misc_feature
<222> LOCATION: (24)..(26)
<223> OTHER INFORMATION: n is a, u, t, g, and c, or a nucleotide
      analogue thereof; may be present or not

<400> SEQUENCE: 31
nnnnndgnnn bnnthvnnnc hnhnnn                                    26

<210> SEQ ID NO 32
<211> LENGTH: 26
<212> TYPE: DNA
<213> ORGANISM: Artificial Sequence
<220> FEATURE:
<223> OTHER INFORMATION: Sequence according to formula (IIe)
<220> FEATURE:
<221> NAME/KEY: misc_feature
<222> LOCATION: (1)..(1)
<223> OTHER INFORMATION: n is a, u, t, g, and c, or a nucleotide
      analogue thereof; may be present or not
<220> FEATURE:
<221> NAME/KEY: misc_feature
<222> LOCATION: (2)..(2)
<223> OTHER INFORMATION: n is a, u, t, g, and c, or a nucleotide
      analogue thereof; may be present or not
<220> FEATURE:
<221> NAME/KEY: misc_feature
<222> LOCATION: (5)..(5)

```
<223> OTHER INFORMATION: n is a, u, t, g, and c, or a nucleotide
      analogue thereof
<220> FEATURE:
<221> NAME/KEY: misc_feature
<222> LOCATION: (8)..(10)
<223> OTHER INFORMATION: n is a, u, t, g, and c, or a nucleotide
      analogue thereof
<220> FEATURE:
<221> NAME/KEY: misc_feature
<222> LOCATION: (18)..(19)
<223> OTHER INFORMATION: n is a, u, t, g, and c, or a nucleotide
      analogue thereof
<220> FEATURE:
<221> NAME/KEY: misc_feature
<222> LOCATION: (24)..(24)
<223> OTHER INFORMATION: may be present or not
<220> FEATURE:
<221> NAME/KEY: misc_feature
<222> LOCATION: (25)..(26)
<223> OTHER INFORMATION: n is a, u, t, g, and c, or a nucleotide
      analogue thereof; may be present or not

<400> SEQUENCE: 32
nnhhnrgnnn yhbthrdnnc ydhhnn                                            26

<210> SEQ ID NO 33
<211> LENGTH: 26
<212> TYPE: DNA
<213> ORGANISM: Artificial Sequence
<220> FEATURE:
<223> OTHER INFORMATION: Sequence according to formula (IIe)
<220> FEATURE:
<221> NAME/KEY: misc_feature
<222> LOCATION: (1)..(1)
<223> OTHER INFORMATION: n is a, u, t, g, and c, or a nucleotide
      analogue thereof; may be present or not
<220> FEATURE:
<221> NAME/KEY: misc_feature
<222> LOCATION: (2)..(2)
<223> OTHER INFORMATION: may be present or not
<220> FEATURE:
<221> NAME/KEY: misc_feature
<222> LOCATION: (8)..(8)
<223> OTHER INFORMATION: n is a, u, t, g, and c, or a nucleotide
      analogue thereof
<220> FEATURE:
<221> NAME/KEY: misc_feature
<222> LOCATION: (19)..(19)
<223> OTHER INFORMATION: n is a, u, t, g, and c, or a nucleotide
      analogue thereof
<220> FEATURE:
<221> NAME/KEY: misc_feature
<222> LOCATION: (24)..(26)
<223> OTHER INFORMATION: may be present or not

<400> SEQUENCE: 33
nhhhvrgndb yhythrdhnc yrhhhh                                            26

<210> SEQ ID NO 34
<211> LENGTH: 26
<212> TYPE: DNA
<213> ORGANISM: Artificial Sequence
<220> FEATURE:
<223> OTHER INFORMATION: Sequence according to formula (IIf)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (25)..(25)
<223> OTHER INFORMATION: may be present or not
<220> FEATURE:
<221> NAME/KEY: misc_feature
<222> LOCATION: (26)..(26)
```

```
<223> OTHER INFORMATION: n is a, u, t, g, and c, or a nucleotide
      analogue thereof; may be present or not

<400> SEQUENCE: 34
hhmhmvgyyy tyhthrvrrc bvmhhn                                        26

<210> SEQ ID NO 35
<211> LENGTH: 26
<212> TYPE: DNA
<213> ORGANISM: Artificial Sequence
<220> FEATURE:
<223> OTHER INFORMATION: Sequence according to formula (IIf)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (25)..(26)
<223> OTHER INFORMATION: may be present or not

<400> SEQUENCE: 35
mmmmmsgyyc ttytmagrrc smchhh                                        26

<210> SEQ ID NO 36
<211> LENGTH: 26
<212> TYPE: DNA
<213> ORGANISM: Artificial Sequence
<220> FEATURE:
<223> OTHER INFORMATION: Sequence according to formula (IIf)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (25)..(26)
<223> OTHER INFORMATION: may be present or not

<400> SEQUENCE: 36
mmmmmsgyyc ttttmagrrc sachmh                                        26

<210> SEQ ID NO 37
<211> LENGTH: 26
<212> TYPE: DNA
<213> ORGANISM: Artificial Sequence
<220> FEATURE:
<223> OTHER INFORMATION: Sequence according to formula (IIg)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (24)..(25)
<223> OTHER INFORMATION: n is a, u, t, g, and c, or a nucleotide
      analogue thereof; may be present or not
<220> FEATURE:
<221> NAME/KEY: misc_feature
<222> LOCATION: (26)..(26)
<223> OTHER INFORMATION: may be present or not

<400> SEQUENCE: 37
hhmamggyyc ttythagrrc cvhnnm                                        26

<210> SEQ ID NO 38
<211> LENGTH: 26
<212> TYPE: DNA
<213> ORGANISM: Artificial Sequence
<220> FEATURE:
<223> OTHER INFORMATION: Sequence according to formula (IIg)
```

-continued

```
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (25)..(26)
<223> OTHER INFORMATION: may be present or not

<400> SEQUENCE: 38
hhaamggcyc ttytmagrgc cvchhm                                              26

<210> SEQ ID NO 39
<211> LENGTH: 26
<212> TYPE: DNA
<213> ORGANISM: Artificial Sequence
<220> FEATURE:
<223> OTHER INFORMATION: Sequence according to formula (IIg)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (24)..(26)
<223> OTHER INFORMATION: may be present or not

<400> SEQUENCE: 39
mmaamggctc ttttmagrgc cmcymm                                              26

<210> SEQ ID NO 40
<211> LENGTH: 26
<212> TYPE: DNA
<213> ORGANISM: Artificial Sequence
<220> FEATURE:
<223> OTHER INFORMATION: Sequence according to formula (IIh)
<220> FEATURE:
<221> NAME/KEY: misc_feature
<222> LOCATION: (1)..(1)
<223> OTHER INFORMATION: n is a, u, t, g, and c, or a nucleotide
      analogue thereof; may be present or not
<220> FEATURE:
<221> NAME/KEY: misc_feature
<222> LOCATION: (2)..(2)
<223> OTHER INFORMATION: may be present or not
<220> FEATURE:
<221> NAME/KEY: misc_feature
<222> LOCATION: (24)..(24)
<223> OTHER INFORMATION: may be present or not
<220> FEATURE:
<221> NAME/KEY: misc_feature
<222> LOCATION: (25)..(25)
<223> OTHER INFORMATION: n is a, u, t, g, and c, or a nucleotide
      analogue thereof; may be present or not
<220> FEATURE:
<221> NAME/KEY: misc_feature
<222> LOCATION: (26)..(26)
<223> OTHER INFORMATION: may be present or not

<400> SEQUENCE: 40
nhaahdghyc tdythasrrc cvhbnh                                              26

<210> SEQ ID NO 41
<211> LENGTH: 26
<212> TYPE: DNA
<213> ORGANISM: Artificial Sequence
<220> FEATURE:
<223> OTHER INFORMATION: Sequence according to formula (IIh)
<220> FEATURE:
<221> NAME/KEY: misc_feature
<222> LOCATION: (1)..(2)
<223> OTHER INFORMATION: may be present or not
<220> FEATURE:
```

```
<221> NAME/KEY: misc_feature
<222> LOCATION: (24)..(24)
<223> OTHER INFORMATION: may be present or not
<220> FEATURE:
<221> NAME/KEY: misc_feature
<222> LOCATION: (25)..(25)
<223> OTHER INFORMATION: n is a, u, t, g, and c, or a nucleotide
     analogue thereof; may be present or not
<220> FEATURE:
<221> NAME/KEY: misc_feature
<222> LOCATION: (26)..(26)
<223> OTHER INFORMATION: may be present or not

<400> SEQUENCE: 41
hhaamggcyc tttthagrgc cvmynm                                          26

<210> SEQ ID NO 42
<211> LENGTH: 26
<212> TYPE: DNA
<213> ORGANISM: Artificial Sequence
<220> FEATURE:
<223> OTHER INFORMATION: Sequence according to formula (IIh)
<220> FEATURE:
<221> NAME/KEY: misc_feature
<222> LOCATION: (1)..(2)
<223> OTHER INFORMATION: may be present or not
<220> FEATURE:
<221> NAME/KEY: misc_feature
<222> LOCATION: (24)..(26)
<223> OTHER INFORMATION: may be present or not

<400> SEQUENCE: 42
hmaaaggcyc ttttmagrgc crmyhm                                          26

<210> SEQ ID NO 43
<211> LENGTH: 24
<212> TYPE: DNA
<213> ORGANISM: Artificial Sequence
<220> FEATURE:
<223> OTHER INFORMATION: Specific histone stem-loop sequence

<400> SEQUENCE: 43
caaaggctct tttcagagcc acca                                            24

<210> SEQ ID NO 44
<211> LENGTH: 24
<212> TYPE: RNA
<213> ORGANISM: Artificial Sequence
<220> FEATURE:
<223> OTHER INFORMATION: Specific histone stem-loop sequence

<400> SEQUENCE: 44
caaaggcucu uuucagagcc acca                                            24

<210> SEQ ID NO 45
<211> LENGTH: 44
<212> TYPE: DNA
<213> ORGANISM: Artificial Sequence
<220> FEATURE:
<223> OTHER INFORMATION: mutated UTR of (alphe-) globin

<400> SEQUENCE: 45
gcccgatggg cctcccaacg ggccctcctc ccctccttgc accg                      44

<210> SEQ ID NO 46
<211> LENGTH: 1870
<212> TYPE: RNA
<213> ORGANISM: Artificial Sequence
<220> FEATURE:
```

<223> OTHER INFORMATION: mRNA sequence ppluc(gc) - muag - a64 - c30 -
      histoneSL

<400> SEQUENCE: 46
gggagaaagc uugaggaugg aggacgccaa gaacaucaag aagggcccgg cgcccuucua      60
cccgcuggag gacgggaccg ccggcgagca gcuccacaag gccaugaagc gguacgcccu     120
ggugccgggc acgaucgccu ucaccgacgc ccacaucgag gucgacauca ccuacgcgga     180
guacuucgag augagcgugc gccuggccga ggccaugaag cgguacggcc ugaacaccaa     240
ccaccggauc gugguguqcu cggagaacag ccugcaguuc uucaugccgg ugcugggcgc     300
ccucuucauc ggcguggccg ucgccccggc gaacgacauc uacaacgagc gggagcugcu     360
gaacagcaug gggaucagcc agccgaccgu ggucuucgug agcaagaagg ccugcagaa      420
gauccugaac gugcagaaga gcugcccau cauccgaaag aucaucauca uggacagcaa     480
gaccgacuac cagggcuucc agucgaugua cacguucgug accagccacc ucccgccggg     540
cuucaacgag uacgacuucg ucccggagag cuucgaccgg gacaagacca ucgcccugau     600
caugaacagc agcggcagca ccggccugcc gaaggggggug gcccugccgc accggaccgc     660
cugcgugcgc uucucgcacg cccgggaccc caucuucggc aaccagauca ucccggacac     720
cgccauccug agcguggugc cguuccacca cggcuucggc auguucacga cccugggcua     780
ccucaucugc ggcuuccggg ugguccugau guaccggguc gaggaggagc uguuccugcg     840
gagccugcag gacuacaaga uccagagcgc gcugcucgug ccgacccugu ucagcuucuu     900
cgccaagagc cccugaucg acaaguacga ccugucgaac cugcacgaga ucgccagcgg     960
gggcgccccg cugagcaagg agugggcga ggccguggcc aagcgguucc accucccggg    1020
cauccgccag ggcuacggcc ugaccgagac cacgagcgcg auccugauca cccccgaggg    1080
ggacgacaag ccgggcgccg ugggcaaggu ggucccguuc uucgaggcca ggugguga     1140
ccuggacacc ggcaagaccc ugggcgugaa ccagcggggc gagcugugcg ugcggggcc    1200
gaugaucaug agcggcuacg ugaacaaccc ggaggccacc aacgcccuca ucgacaagga    1260
cggcuggcug cacagcggcg acaucgccua cugggacgag gacagcacu ucuucaucgu     1320
cgaccggcug aagucgcuga ucaaguacaa gggcuaccag guggcgccgg ccgagcugga    1380
gagcauccug cuccagcacc ccaacaucuu cgacgccggc guggccgggc ugccggacga    1440
cgacgccggc gagcugccgg ccgcgguggu ggugcuggag cacggcaaga ccaugacgga    1500
gaaggagauc gucgacuacg uggccagcca ggugaccacc gccaagaagc ugcggggcgg    1560
cguggguuc guggacgagg ucccgaaggg ccugaccggg aagcucgacg cccggaagau    1620
ccgcgagauc cugaucaagg ccaagaaggg cggcaagauc gccguguaag acuaguuaua    1680
agacugacua gcccgauggg ccucccaacg ggcccuccuc cccuccuugc accgagauua    1740
auaaaaaaaa aaaaaaaaaa aaaaaaaaaa aaaaaaaaaa aaaaaaaaaa aaaaaaaaaa    1800
aaaaaaugca uccccccccc cccccccccc cccccccccc ccaaaggcuc uuuucagagc    1860
caccagaauu                                                          1870

<210> SEQ ID NO 47
<211> LENGTH: 1712
<212> TYPE: RNA
<213> ORGANISM: Artificial Sequence
<220> FEATURE:
<223> OTHER INFORMATION: PpLuc(wt) - A30

<400> SEQUENCE: 47

```
ggagaaagc uuaccaugga agacgccaaa aacauaaaga aaggcccggc gccauucuau      60
ccuuuagagg auggaaccgc ugagagcaa cugcauaagg cuaugaagag auacgcccug     120
guuccuggaa caauugcuuu uacagaugca cauaucgagg ugaacaucac guacgcggaa    180
uacuucgaaa uguccguucg guuggcagaa gcuaugaaac gauaugggcu gaauacaaau    240
cacagaaucg ucguaugcag ugaaaacucu cuucaauucu uuaugccggu guugggcgcg    300
uuauuuaucg gaguugcagu ugcgcccgcg aacgacauuu auaaugaacg ugaauugcuc    360
aacaguauga acauuucgca gccuaccgua guguuguuu ccaaaaaggg guugcaaaaa     420
auuuugaacg ugcaaaaaaa auuaccaaua uccagaaaaa uuauuaucau ggauucuaaa    480
acggauuacc agggauuuca gucgauguac acguucguca caucucaucu accucccggu    540
uuuaaugaau acgauuuugu accagagucc uuugaucgug acaaaacaau ugcacugaua    600
augaauagcu cuggaucuac ugggguuaccu aaggguguagg cccuuccgca uagaacugcc    660
ugcgucagau ucucgcaugc cagagauccu auuuuuggca aucaaaucau uccggauacu    720 gcgauuuaa guguuguucc auccaucac gguuuugaa uguuuacuac acucggauau       780
uugauaugug gauuucgagu cgucuuaaug uauagauuug aagaagagcu guuuuuacga    840
ucccuucagg auuacaaaau ucaaagugcg uugcuaguac caacccauau ucauucuuc     900 gccaaaagca cucugauuga caaauacgau uuaucuaauu uacacgaaau ugcuucuggg    960
ggcgcaccuc uuucgaaaga agucggggaa gcgguugcaa aacgcuucca ucuuccaggg   1020
auacgacaag gauaugggcu cacugagacu acaucagcua uucugauuac acccgagggg   1080
gaugauaaac cgggcgcggu cgguaaaguu guuccauuuu ugaagcgaa gguuuggau     1140 cuggauaccg gaaaacgcu gggcguuaau cagagagcg aauuagugu cagaggaccu      1200 augauuaugu ccgguaugu aaacaauccg gaagcgacca acgccuugau ugacaaggau    1260
ggauggcuac auucuggaga cauagcuuac ugggacgaag acgaacacuu cuucauaguu   1320
gaccgcuuga agucuuuaau uaaauacaaa ggauaucagg uggccccgc ugaauuggaa    1380 ucgauauugu uacaacacc caacaucuuc gacgcgggcg uggcaggucu ucccgacgau   1440
gacgccggug aacuucccgc cgccguuguu guuuuggagc acgaaagac gaugacggaa    1500 aaagagaucg uggauuacgu cgccagucaa guaacaaccg cgaaaaaguu gcgcggagga   1560
guugugguuu uggacgaagu accgaaaggu cuuaccggaa aacucgacgc aagaaaaauc   1620
agagagaucc ucauaaaggc caagaagggc ggaaagucca aauugugagg acuaguagau   1680
cuaaaaaaaa aaaaaaaaaa aaaaaaaaaa aa                                 1712

<210> SEQ ID NO 48
<211> LENGTH: 1746
<212> TYPE: RNA
<213> ORGANISM: Artificial Sequence
<220> FEATURE:
<223> OTHER INFORMATION: R3454: PpLuc(wt) - A64

<400> SEQUENCE: 48 ggagaaagc uuaccaugga agacgccaaa aacauaaaga aaggcccggc gccauucuau      60
ccuuuagagg auggaaccgc ugagagcaa cugcauaagg cuaugaagag auacgcccug     120
guuccuggaa caauugcuuu uacagaugca cauaucgagg ugaacaucac guacgcggaa    180
uacuucgaaa uguccguucg guuggcagaa gcuaugaaac gauaugggcu gaauacaaau    240
cacagaaucg ucguaugcag ugaaaacucu cuucaauucu uuaugccggu guugggcgcg    300
uuauuuaucg gaguugcagu ugcgcccgcg aacgacauuu auaaugaacg ugaauugcuc    360
```

```
aacaguauga acauuucgca gccuaccgua guguuuguuu ccaaaaaggg guugcaaaaa    420
auuuugaacg ugcaaaaaaa auuaccaaua auccagaaaa uuauuaucau ggauucuaaa    480
acggauuacc agggauuuca gucgauguac acguucguca caucucaucu accucccggu    540
uuuaaugaau acgauuuugu accagagucc uuugaucgug acaaaacaau ugcacgauua    600
augaauagcu cuggaucuac uggguuaccu aagggugugg cccuuccgca uagaacugcc    660
ugcgucagau ucucgcaugc cagagauccu auuuuggca aucaaaucau ccggauacu    720 gcgauuuuaa guguuguucc auuccaucac gguuuuggaa uguuuacuac acucggauau    780
uugauaugug gauuucgagu cgucuuaaug uauagauuug aagaagagcu guuuuuacga    840
ucccuucagg auuacaaaau ucaaagugcg uugcuaguac caacccuauu uucauucuuc    900
gccaaaagca cucugauuga caaauacgau uuaucuaauu uacacgaaau ugcuucuggg    960
ggcgcaccuc uuucgaaaga agucggggaa gcgguugcaa aacgcuucca ucuuccaggg    1020
auacgacaag auaugggcu cacugagacu acaucagcua uucugauuac acccgagggg    1080
gaugauaaac cgggcgcggu cgguaaaguu guuccauuuu uugaagcgaa gguuguggau    1140
cuggauaccg ggaaaacgcu gggcguuaau cagagaggcg aauuaugugu cagaggaccu    1200
augauuaugu ccgguuaugu aaacaauccg gaagcgacca acgccuugau ugacaaggau    1260
ggauggcuac auucuggaga cauagcuuac ugggacgaag acgaacacuu cuucauaguu    1320
gaccgcuuga agucuuuaau uaaauacaaa ggauaucagg uggccccgc ugaauuggaa    1380 ucgauauugu uacaacaccc caacaucuuc gacgcgggcg uggcaggucu cccgacgau    1440 gacgccggug aacuucccgc cgccguuguu guuuggagc acggaaagac gaugacggaa    1500
aaagagaucg uggauuacgu cgccagucaa guaacaaccg cgaaaaaguu gcgcggagga    1560
guuguguuug uggacgaagu accgaaaggu cuuaccggaa aacucgacgc aagaaaaauc    1620
agagagaucc ucauaaaggc caagaagggc ggaaagucca aauugugagg acuaguagau    1680
cuaaaaaaaa aaaaaaaaaa aaaaaaaaaa aaaaaaaaaa aaaaaaaaaa aaaaaaaaaa    1740
aaaaaa                                                              1746

<210> SEQ ID NO 49
<211> LENGTH: 1810
<212> TYPE: RNA
<213> ORGANISM: Artificial Sequence
<220> FEATURE:
<223> OTHER INFORMATION: R2462: PpLuc(GC)-A64-C30-HistoneSL

<400> SEQUENCE: 49
gggagaaagc uugaggaugg aggacgccaa gaacaucaag aagggcccgg cgcccuucua     60
cccgcuggag gacgggaccg ccggcgagca gcuccacaag gccaugaagc gguacgcccu    120
ggugccgggc acgaucgccu uccgacgc ccacaucgag gucgacauca ccuacgcgga    180
guacuucgag augagcgugc gccuggccga ggccaugaag cgguacggcc ugaacaccaa    240
ccaccggauc guggugugcu cggagaacag ccugcaguuc uucaugccgg ugcugggcgc    300
ccucuucauc ggcguggccg ucgccccggc gaacgacauc uacaacgagc gggagcugcu    360
gaacagcaug gggaucagcc agccgaccgu gguguucgug agcaagaagg ccugcagaa    420 gauccugaac gugcagaaga agcugcccau cauccagaag aucaucauca uggacagcaa    480
gaccgacuac cagggcuucc agucgaugua cacguucgug accagccacc ucccgccggg    540
cuucaacgag uacgacuucg ucccggagag cuucgaccgg gacaagacca ucgcccugau    600
```

-continued

| | |
|---|---|
| caugaacagc agcggcagca ccggccugcc aaggggggug gcccugccgc accggaccgc | 660 |
| cugcgugcgc uucucgcacg cccgggaccc caucuucggc aaccagauca cccggacac | 720 |
| cgccauccug agcgugguc cguuccacca cggcuucggc auguucacga cccugggcua | 780 |
| ccucaucugc ggcuuccggg ugguccugau guaccgguuc gaggaggagc uguuccugcg | 840 |
| gagccugcag gacuacaaga uccagagcgc gcugucgug ccgacccugu ucagcuucuu | 900 |
| cgccaagagc acccugaucg acaaguacga ccugucgaac cugcacgaga ucgccagcgg | 960 |
| gggcgccccg cugagcaagg aggugggcga ggccguggcc aagcgguucc accucccggg | 1020 |
| cauccgccag ggcuacggcc ugaccgagac cacgagcgcg auccugauca cccccgaggg | 1080 |
| ggacgacaag ccgggcgccg ugggcaaggu gguccccguuc uucgaggcca aggugguga | 1140 |
| ccuggacacc ggcaagaccc uggcgcgugaa ccagcggggc gagcugugcg ugcggggggcc | 1200 |
| gaugaucaug agcggcuacg ugaacaaccc ggaggccacc aacgcccuca ucgacaagga | 1260 |
| cggcuggcug cacagcggcg acaucgccua cugggacgag gacgagcacu ucuucaucgu | 1320 |
| cgaccggcug aagucgcuga ucaaguacaa gggcuaccag guggcgccgg ccgagcugga | 1380 |
| gagcauccug cuccagcacc ccaacaucuu cgacgccggc guggccgggc ugccggacga | 1440 |
| cgacgccggc gagcugccgg ccgcggugu ggugcuggag cacggcaaga ccaugacgga | 1500 |
| gaaggagauc gucgacuacg uggccagcca ggugaccacc gccaagaagc ugcggggcgg | 1560 |
| cguggguuc guggacgagg ucccgaaggg ccugaccggg aagcucgacg cccggaagau | 1620 |
| ccgcgagauc cugaucaagg ccaagaaggg cggcaagauc gccguguaag acuaguagau | 1680 |
| cuaaaaaaaa aaaaaaaaaa aaaaaaaaaa aaaaaaaaaa aaaaaaaaaa aaaaaaaaaa | 1740 |
| aaaaaaugca uccccccccc cccccccccc cccccccccc ccaaaggcuc uuuucagagc | 1800 |
| caccagaauu | 1810 |

<210> SEQ ID NO 50
<211> LENGTH: 1846
<212> TYPE: RNA
<213> ORGANISM: Artificial Sequence
<220> FEATURE:
<223> OTHER INFORMATION: R1256: PpLuc(GC)-muag-A64-C30

<400> SEQUENCE: 50

| | |
|---|---|
| gggagaaagc uugaggaugg aggacgccaa gaacaucaag aagggcccgg cgcccuucua | 60 |
| cccgcuggag gacgggaccg ccggcgagca gcuccacaag gccaugaagc gguacgcccu | 120 |
| ggugccgggc acgaucgccu ucaccgacgc ccacaucgag gucgacauca ccuacgcgga | 180 |
| guacuucgag augagcgugc gccuggccga ggccaugaag cgguacggcc ugaacaccaa | 240 |
| ccaccggauc guggugugcu cggagaacag ccugcaguuc uucaugccgg ugcugggcgc | 300 |
| ccucuucauc ggcguggccg ucgccccggc gaacgacauc uacaacgagc gggagcugcu | 360 |
| gaacagcaug gggaucagcc agccgaccgu gguguucgug agcaagaagg gccugcagaa | 420 |
| gauccugaac gugcagaaga gcugcccau caucagaag aucaucauca uggacagcaa | 480 |
| gaccgacuac cagggcuucc agucgaugua cacguucgug accagccacc uccgccggg | 540 |
| cuucaacgag uacgacuucg uccggagag cuucgaccgg acaagacca ucgcccugau | 600 |
| caugaacagc agcggcagca ccggccugcc aaggggggug gcccugccgc accggaccgc | 660 |
| cugcgugcgc uucucgcacg cccgggaccc caucuucggc aaccagauca cccggacac | 720 |
| cgccauccug agcgugguc cguuccacca cggcuucggc auguucacga cccugggcua | 780 |
| ccucaucugc ggcuuccggg ugguccugau guaccgguuc gaggaggagc uguuccugcg | 840 |

```
gagccugcag gacuacaaga uccagagcgc gcugcucgug ccgacccugu ucagcuucuu    900
cgccaagagc acccugaucg acaaguacga ccugucgaac cugcacgaga ucgccagcgg    960
gggcgccccg cugagcaagg aggugggcga ggccguggcc aagcgguucc accucccggg   1020
cauccgccag ggcuacggcc ugaccgagac cacgagcgcg auccugauca cccccgaggg   1080
ggacgacaag ccgggcgccg ugggcaaggu gguccccguuc uucgaggcca aggugguga    1140 ccuggacacc ggcaagaccc uggggcgugaa ccagcggggc gagcugugcg ugcggggggcc  1200 gaugaucaug agcggcuacg ugaacaaccc ggaggccacc aacgcccuca ucgacaagga   1260
cggcuggcug cacagcggcg acaucgccua cugggacgag gacgagcacu ucuucaucgu   1320
cgaccggcug aagucgcuga ucaaguacaa gggcuaccag guggcgccgg ccgagcugga   1380
gagcauccug cuccagcacc ccaacaucuu cgacgccggc guggccgggc ugccggacga   1440
cgacgccggc gagcugccgg ccgcgguggu ggugcuggag cacggcaaga ccaugacgga   1500
gaaggagauc gucgacuacg uggccagcca ggugaccacc gccaagaagc ugcggggcgg   1560
cguggcguuc guggacgagg ucccgaaggg ccugaccggg aagcucgacg cccggaagau   1620
ccgcgagauc cugaucaagg ccaagaaggg cggcaagauc gccguguaag acuaguuaua   1680
agacugacua gcccgauggg ccucccaacg ggccccuccuc cccuccuugc accgagauua   1740
auaaaaaaaa aaaaaaaaaa aaaaaaaaaa aaaaaaaaaa aaaaaaaaaa aaaaaaaaaa   1800
aaaaaaugca uccccccccc cccccccccc cccccccccc cucuag                 1846

<210> SEQ ID NO 51
<211> LENGTH: 1870
<212> TYPE: RNA
<213> ORGANISM: Artificial Sequence
<220> FEATURE:
<223> OTHER INFORMATION: R2393: PpLuc(nat)-muag-A64-C30-HistoneSL

<400> SEQUENCE: 51
gggagaaagc uuaccaugga agacgccaaa aacauaaaga aaggcccggc gccauucuau     60
ccuuuagagg auggaaccgc uggagagcaa cugcauaagg cuaugaagag auacgcccug    120
guuccuggaa caauugcuuu uacagaugca cauaucgagg ugaacaucac guacgcggaa    180
uacuucgaaa ugucccuucg guuggcagaa gcuaugaaac gauauggcu gaauacaaau    240 cacagaaucg ucguaugcag ugaaaacucu cuucaauucu uuaugccggu guugggcgcg    300
uuauuuaucg gaguugcagu ugcgcccgcg aacgacauuu auaaugaacg ugaauugcuc    360
aacaguauga acauuucgca gccuaccgua guguuuguuu ccaaaaaggg guugcaaaaa    420
auuuugaacg ugcaaaaaaa auuaccaaua auccagaaaa uuauuaucau ggauucuaaa    480
acggauuacc agggauuuca gucgauguac acguucguca caucucaucu accucccggu    540
uuuaaugaau acgauuuugu accagaaucc uuugaucgug acaaaacaau ugcacugaua    600
augaauagcu cuggaucuac uggguuaccu aaggggugugg cccuuccgca uagaacugcc    660
ugcgucagau ucucgcaugc cagagauccu auuuuuggca aucaaaucau ccggauacu    720 gcgauuuuaa guguuguucc auccaucac gguuuuggaa uguuuacuac acucggauau    780 uugauauguggg gauuucgagu cgucuuaaug uauagauuug aagaagagcu guuuuuacga    840
ucccuucagg auuacaaaau ucaaagugcg uugcuaguac caacccuauu uucauucuuc    900
gccaaaagca cucugauuga caaauacgau uuaucuaauu uacacgaaau ugcuucuggg    960
ggcgcaccuc uuucgaaaga agucggggaa gcgguugcaa aacgcuucca ucuuccaggg   1020
```

| | |
|---|---|
| auacgacaag gauaugggcu cacugagacu acaucagcua uucugauuac acccgagggg | 1080 |
| gaugauaaac cgggcgcggu cgguaaaguu guuccauuuu uugaagcgaa gguuguggau | 1140 |
| cuggauaccg ggaaaacgcu gggcguuaau cagagaggcg aauuaugugu cagaggaccu | 1200 |
| augauuaugu ccgguuaugu aaacaauccg gaagcgacca acgccuugau ugacaaggau | 1260 |
| ggauggcuac auucuggaga cauagcuuac ugggacgaag acgaacacuu cuucauaguu | 1320 |
| gaccgcuuga agucuuuaau uaaauacaaa ggauaucagg uggcccccgc ugaauuggaa | 1380 |
| ucgauauugu uacaacaccc caacaucuuc gacgcgggcg uggcaggucu ucccgacgau | 1440 |
| gacgccggug aacuucccgc cgccguuguu guuuuggagc acggaaagac gaugacggaa | 1500 |
| aaagagaucg uggauuacgu cgccagucaa guaacaaccg cgaaaaaguu gcgcggagga | 1560 |
| guuguguuug uggacgaagu accgaaaggu cuuaccggaa aacucgacgc aagaaaaauc | 1620 |
| agagagaucc ucauaaaggc caagaagggc ggaaagucca aauugugagg acuaguuaua | 1680 |
| agacugacua gcccgauggg ccucccaacg ggcccuccuc cccuccugc accgagauua | 1740 |
| auaaaaaaaa aaaaaaaaaa aaaaaaaaaa aaaaaaaaaa aaaaaaaaaa aaaaaaaaaa | 1800 |
| aaaaaaugca uccccccccc cccccccccc cccccccccc ccaaaggcuc uuuucagagc | 1860 |
| caccagaauu | 1870 |

<210> SEQ ID NO 52
<211> LENGTH: 1792
<212> TYPE: RNA
<213> ORGANISM: Artificial Sequence
<220> FEATURE:
<223> OTHER INFORMATION: R2403: RAV-G(GC)-muag-A64-C30-histoneSL

<400> SEQUENCE: 52

| | |
|---|---|
| gggagaaagc uuaccauggu gccccaggcc cugucuuucg uccgcugcu gguguucccc | 60 |
| cucugcuucg gcaaguuccc caucuacacc auccccgaca agcuggggcc guggagcccc | 120 |
| aucgacaucc accaccuguc cugccccaac aaccucgugg ucgaggacga gggcugcacc | 180 |
| aaccugagcg gguucuccua caugagcug aaggugggcu acaucagcgc caucaagaug | 240 |
| aacggguuca cgugcaccgg cguggucacc gaggcggaga ccuacacgaa cuucguggc | 300 |
| uacgugacca ccaccuucaa gcggaagcac uuccgcccca cgccggacgc cugccgggcc | 360 |
| gccuacaacu ggaagauggc cggggacccc cgcuacgagg aguccccuca caaccccuac | 420 |
| cccgacuacc acuggcugcg gaccgucaag accaccaagg agagccuggu gaucaucucc | 480 |
| ccgagcgugg cggaccucga ccccuacgac cgcccccugc acagccgggu cuuccccggc | 540 |
| gggaacugcu ccggcgugge cgugagcucc acguacugca gcaccaacca cgacuacacc | 600 |
| aucuggaugc ccgagaaccc cgcgcugggg auguccugcg acaucuucac caacagccgg | 660 |
| ggcaagcgcg ccuccaaggg cagcgagacg ugcgggguucg ucgacgagcg gggccucuac | 720 |
| aagucccuga ggggggccug caagcugaag cucugcggcg ugcugggccu cgcgcucaug | 780 |
| gacgggaccu ggguggcgau gcagaccagc aacgagacca guggugccc cccggccag | 840 |
| cuggucaacc ugcacgacuu ccggagcgac gagaucgagc accucguggu ggaggagcug | 900 |
| gucaagaagc gcgaggagug ccuggacgcc cucgagucca ucaugacgac caagagcgug | 960 |
| uccuuccggc gccugagcca ccugcggaag cucgugcccg gguucggcaa ggccuacacc | 1020 |
| aucuucaaca gacccugau ggaggccgac gcccacuaca guccguccg cacguggaac | 1080 |
| gagaucaucc cgagcaaggg gugccugcgg ugggcggcc gcugcacccc ccacgucaac | 1140 |
| gggguguucu ucaacggcau caucccucggg cccgacggca acgugcugau ccccgagaug | 1200 |

```
caguccagcc ugcuccagca gcacauggag cugcugguc u ccagcgugau cccgcucaug    1260
cacccccugg cggacccc uc caccguguuc aagaacgggg acgaggccga ggacuucguc    1320
gaggugcacc ugcccgacgu gcacgagcgg aucagcggcg ucgaccucgg ccugccgaac    1380 uggggga agu acgugcugcu cuccgccggc gcccugaccg cccugaugcu gaucaucuuc    1440
cucaugaccu gcuggcgccg ggugaaccgg agcgagccca cgcagcacaa ccugcgcggg    1500
accggcgggg aggucuccgu gacccgcag agcgggaaga ucauccc ag cuggagucc      1560 uacaagagcg gcggcgagac cgggcuguga ggacuaguua uagacugac uagcccgaug     1620 ggccucccaa cgggcccucc uccccuccuu gcaccgagau uaau aaaaaa aaaaaaaaaa   1680 aaaaaaaaaa aaaaaaaaaa aaaaaaaaaa aaaaaaaaa a aaaaaaaug caucccccc     1740 cccccccccc cccccccccc cccaaaggc ucuuucaga gccaccgaaa uu              1792
```

<210> SEQ ID NO 53
<211> LENGTH: 638
<212> TYPE: RNA
<213> ORGANISM: Artificial Sequence
<220> FEATURE:
<223> OTHER INFORMATION: R3513: EPO (wt)-A30

<400> SEQUENCE: 53

```
gggagaaagc uuaccauggg ggugcccgaa cgucccaccc ugcugcuuuu acucuccuug      60
cuacugauuc cucugggccu cccagcc ucu gugcucccc c acgccucau cugcgacagu    120 cgaguucugg agaguacau cuuagaggcc aaggaggcag aaaaugucac gaugggu ugu    180 gcagaaggu c ccagacugag ugaaaauauu acagucccag auaccaaagu caacuucuau    240
gcuuggaaaa gaauggaggu ggaagaacag gccauagaag uuuggcaagg ccugucccug    300
cucucagaag ccauccugca ggcccaggcc cugcuagcca auuccuccca gccaccagag    360
acccuucagc uucauauaga caaagccauc aguggcuuac guagcucuc uucacugcuu    420 cggguacugg gagcucagaa ggaauugaug ucgccuccag auacc acccc accugcucca    480 cuccgaacac ucacaguuga uacuuucugc aagcucuucc gggucuacgc caacuuccuc    540
cgggggaaac ugaagcugua cacggggagag gucugcagga gaggggacag gugaccacua   600
guagaucuaa aaaaaaaaaa aaaaaaaaaa aaaaaaaa                             638
```

<210> SEQ ID NO 54
<211> LENGTH: 981
<212> TYPE: RNA
<213> ORGANISM: Artificial Sequence
<220> FEATURE:
<223> OTHER INFORMATION: R3135: HSD17B4-EPO (GC)-albumin7-A64-C30-
      histoneSL

<400> SEQUENCE: 54

```
ggucccgca gucggcgucc agcggcucug cuuguucgug ugugucgu ugcaggccuu        60 auucaagcuu accaugggcg ugcccgagcg gccgacccug cuccugcugc ucagccugcu    120 gcucauccc c cuggggcugc ccguccucug cgccccccg cgccugaucu gcgacucccg    180
ggugcuggag cgcuacaucc ucgaggccaa ggaggcggag aacgugacca ugggcugcgc    240
cgaggggccc cggcugagcg agaacaucac gguccccgac accaagguga acuucuacgc    300
cuggaagcgu auggaggugg aggagcaggc caucgagguc ugg cagggcc ugucccuccu   360 gagcgaggcc auccugcagg cgcaggcccu ccugccca ac uccagccagc ccccgggagac   420 acugcagcuc cacaucgaca aggccaucuc cgggcugcgg agccugaccu cccuccugcg    480
```

```
cgugcugggc gcgcagaagg agcucaugag cccgcccgac acgacccccc cggccccgcu    540
gcggacccug accguggaca cguucugcaa gcucuuccgc gucuacgcca acuuccugcg    600
gggcaagcug aagcucuaca ccggggaggu gugccgccgg ggcgaccgcu gaccacuagu    660
gcaucacauu uaaaagcauc ucagccuacc augagaauaa gagaaagaaa augaagauca    720
auagcuuauu caucucuuuu ucuuuuucgu uggguguaaag ccaacacccu gucuaaaaaa    780
cauaaauuuc uuuaaucauu uugccucuuu ucucugugcu ucaauuaaua aaaauggaa     840 agaaccuaga ucuaaaaaaa aaaaaaaaa aaaaaaaaa aaaaaaaaa                 900 aaaaaaaaaa aaaaaaaugc auccccccccc cccccccccc cccaaaggcu              960
cuuuucagag ccaccagaau u                                              981
```

<210> SEQ ID NO 55
<211> LENGTH: 42
<212> TYPE: DNA
<213> ORGANISM: Homo sapiens

<400> SEQUENCE: 55

```
ggcgctgcct acggaggtgg cagccatctc cttctcggca tc                       42
```

<210> SEQ ID NO 56
<211> LENGTH: 75
<212> TYPE: DNA
<213> ORGANISM: Homo sapiens

<400> SEQUENCE: 56

```
gcggctcggc cattttgtcc cagtcagtcc ggaggctgcg gctgcagaag taccgcctgc    60
ggagtaactg caaag                                                     75
```

<210> SEQ ID NO 57
<211> LENGTH: 186
<212> TYPE: DNA
<213> ORGANISM: Homo sapiens

<400> SEQUENCE: 57

```
catcacattt aaaagcatct cagcctacca tgagaataag agaaagaaaa tgaagatcaa    60
aagcttattc atctgttttt cttttcgtt ggtgtaaagc caacaccctg tctaaaaaac    120
ataaatttct ttaatcattt tgcctctttt ctctgtgctt caattaataa aaatggaaa    180 gaatct                                                              186
```

<210> SEQ ID NO 58
<211> LENGTH: 186
<212> TYPE: DNA
<213> ORGANISM: Homo sapiens

<400> SEQUENCE: 58

```
catcacattt aaaagcatct cagcctacca tgagaataag agaaagaaaa tgaagatcaa    60
tagcttattc atctcttttt cttttcgtt ggtgtaaagc caacaccctg tctaaaaaac    120
ataaatttct ttaatcattt tgcctctttt ctctgtgctt caattaataa aaatggaaa    180 gaacct                                                              186
```

<210> SEQ ID NO 59
<211> LENGTH: 110
<212> TYPE: DNA
<213> ORGANISM: Homo sapiens

<400> SEQUENCE: 59
gctggagcct cggtggccat gcttcttgcc ccttgggcct ccccccagcc cctcctcccc 60
ttcctgcacc cgtacccccg tggtctttga ataaagtctg agtgggcggc 110

<210> SEQ ID NO 60
<211> LENGTH: 108
<212> TYPE: DNA
<213> ORGANISM: Homo sapiens

<400> SEQUENCE: 60
gctggagcct cggtagccgt tcctcctgcc cgctgggcct cccaacgggc cctcctcccc 60
tccttgcacc ggcccttcct ggtctttgaa taaagtctga gtgggcag 108

<210> SEQ ID NO 61
<211> LENGTH: 132
<212> TYPE: DNA
<213> ORGANISM: Homo sapiens

<400> SEQUENCE: 61
gctcgctttc ttgctgtcca atttctatta aaggttcctt tgttccctaa gtccaactac 60
taaactgggg gatattatga agggccttga gcatctggat tctgcctaat aaaaaacatt 120
tattttcatt gc 132

<210> SEQ ID NO 62
<211> LENGTH: 44
<212> TYPE: DNA
<213> ORGANISM: Artificial Sequence
<220> FEATURE:
<223> OTHER INFORMATION: Center, alpha-complex-binding portion of the 3'UTR of an alpha-globin gene

<400> SEQUENCE: 62
gcccgatggg cctcccaacg ggccctcctc ccctccttgc accg 44

<210> SEQ ID NO 63
<211> LENGTH: 574
<212> TYPE: PRT
<213> ORGANISM: respiratory syncytial virus

<400> SEQUENCE: 63

Met Glu Leu Pro Ile Leu Lys Ala Asn Ala Ile Thr Thr Ile Leu Ala
1 5 10 15

Ala Val Thr Phe Cys Phe Ala Ser Ser Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Asn
65 70 75 80

Gln Glu Leu Asp Lys Tyr Lys Asn Ala Val Thr Glu Leu Gln Leu Leu
85 90 95

Met Gln Ser Thr Thr Ala Ala Asn Asn Arg Ala Arg Arg Glu Leu Pro
100 105 110

Arg Phe Met Asn Tyr Thr Leu Asn Asn Thr Lys Lys Thr Asn Val Thr
115 120 125

Leu Ser Lys Lys Arg Lys Arg Arg Phe Leu Gly Phe Leu Leu Gly Val
130 135 140

```
Gly Ser Ala Ile Ala Ser Gly Ile Ala Val Ser Lys Val Leu His Leu
145                 150                 155                 160

Glu Gly Glu Val Asn Lys Ile Lys Ser Ala Leu Leu Ser Thr Asn Lys
            165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
            195                 200                 205

Lys Gln Ser Cys Arg Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
            245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
            275                 280                 285

Met Ser Ile Ile Lys Glu Glu Val Leu Ala Tyr Val Val Gln Leu Pro
290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
            325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
            355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
            435                 440                 445

Thr Val Ser Val Gly Asn Thr Leu Tyr Tyr Val Asn Lys Gln Glu Gly
            450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
            500                 505                 510

Leu His His Val Asn Ala Gly Lys Ser Thr Thr Asn Ile Met Ile Thr
            515                 520                 525

Thr Ile Ile Ile Val Ile Ile Val Ile Leu Leu Ser Leu Ile Ala Val
            530                 535                 540

Gly Leu Leu Leu Tyr Cys Lys Ala Arg Ser Thr Pro Val Thr Leu Ser
545                 550                 555                 560
```

Lys Asp Gln Leu Ser Gly Ile Asn Asn Ile Ala Phe Ser Asn
         565                 570

<210> SEQ ID NO 64
<211> LENGTH: 2107
<212> TYPE: RNA
<213> ORGANISM: Artificial Sequence
<220> FEATURE:
<223> OTHER INFORMATION: RSV-F long (GC) R2510

<400> SEQUENCE: 64

| | | | | | |
|---|---|---|---|---|---|
| ggggcgcugc | cuacggaggu | ggcagccauc | uccuucucgg | caucaagcuu | accauggagc | 60 |
| ugcccauccu | caaggccaac | gccaucacca | ccauccuggc | ggccgugacg | uucugcuucg | 120 |
| ccagcucccu | gaacaucacc | gaggaguucu | accagagcac | cugcuccgcc | gucagcaagg | 180 |
| gcuaccuguc | cgccuccgg | accggguggu | acacgagcgu | gaucaccauc | gagcugucca | 240 |
| acaucaagga | gaacaagugc | aacggcaccg | acgcgaaggu | gaagcugauc | aaccaggagc | 300 |
| ucgacaagua | caagaacgcc | gucaccgagc | ugcagcugcu | caugcagagc | acgaccgccg | 360 |
| ccaacaaccg | cgcgcggcgc | gagcugccgc | gguucaugaa | cuacacccug | aacaacacca | 420 |
| agaagacgaa | cgugacccuc | uccaagaagc | gcaagcggcg | cuuccugggg | uuccugcucg | 480 |
| gcgugggag | cgccaucgcc | uccggcaucg | ccgucagcaa | ggugcugcac | cuggagggcg | 540 |
| aggugaacaa | gaucaagucc | gccuccuga | gcaccaacaa | ggcggucgug | cccugagca | 600 |
| acggggugcu | cguccucacc | agcaaggugc | uggaccugaa | gaacuacauc | gacaagcagc | 660 |
| uccugcccau | cgugaacaag | caguccugcc | ggaucagcaa | caucgagacg | gucaucgagu | 720 |
| uccagcagaa | gaacaaccgc | cugcucgaga | ucacccggga | guucagcgug | aacgccggcg | 780 |
| ugaccacccc | cgucuccacg | uacaugcuga | ccaacagcga | gcugcucucc | cugaucaacg | 840 |
| acaugcccau | caccaacgac | cagaagaagc | ugaugagcaa | caacgugcag | aucgugcgcc | 900 |
| agcaguccua | cagcaucaug | uccaucauca | aggaggaggu | cccgccuac | guggugcagc | 960 |
| ugccgcugua | cggggucauc | gacacccccu | gcuggaagcu | ccacacgagc | ccccugugca | 1020 |
| ccaccaacac | caaggagggc | uccaacaucu | gccugacgcg | gaccgaccgc | ggguggacu | 1080 |
| gcgacaacgc | cggcagcgug | uccuucuccc | ccaggccga | gaccugcaag | guccagagca | 1140 |
| accggguguu | cugcgacacc | augaacuccc | ucacgcugcc | gagcgaggug | aaccugugca | 1200 |
| acgucgacau | cuucaacccc | aaguacgacu | gcaagaucau | gaccuccaag | accgacguga | 1260 |
| gcuccagcgu | gaucaccucc | cucggcgcga | ucgucagcug | cuacgggaag | acgaagugca | 1320 |
| ccgccagcaa | caagaaccgc | ggcaucauca | agaccuucuc | caacgggugc | gacuacguga | 1380 |
| gcaacaaggg | cguggacacc | gucuccgugg | gcaacacccu | guacuacgug | aacaagcagg | 1440 |
| aggggaagag | ccuguacguc | aagggcgagc | ccaucaucaa | cuucuacgac | ccccucgugu | 1500 |
| ucccguccga | cgaguucgac | gccagcaucu | cccaggugaa | cgagaagauc | aaccagagcc | 1560 |
| uggccuucau | ccggaagucc | gacgagcugc | ugcaccacgu | caacgccggg | aagagcacga | 1620 |
| ccaacaucau | gaucaccacc | aucaucaucg | ugaucaucgu | gauccuccug | cccugaucg | 1680 |
| cggucggccu | ccugcuguac | ugcaaggccc | gcagcacgcc | cgugacccuc | uccaaggacc | 1740 |
| agcugagcgg | gaucaacaac | aucgccuucu | ccaacgagg | acuagugcau | cacauuuaaa | 1800 |
| agcaucucag | ccuaccauga | gaauaagaga | aagaaauga | agaucaauag | cuuauucauc | 1860 |
| ucuuuucuu | uuucguuggu | guaaagccaa | caccccugucu | aaaaaacaua | aauuucuuua | 1920 |
| aucauuuugc | cucuuuucuc | ugugcuucaa | uuaauaaaaa | auggaaagaa | ccuagaucua | 1980 |

```
aaaaaaaaaa aaaaaaaaaa aaaaaaaaaa aaaaaaaaaa aaaaaaaaaa aaaaaaaaaa    2040
aaaugcaucc cccccccccc cccccccccc ccccccccca aaggcucuuu ucagagccac    2100
cagaauu                                                              2107
```

METHOD FOR INCREASING EXPRESSION OF RNA-ENCODED PROTEINS

The present application is a continuation of U.S. application Ser. No. 15/048,031, now U.S. Pat. No. 10,293,060, filed Feb. 19, 2016, which is a continuation of International Application No. PCT/EP2014/002300, filed Aug. 21, 2014, which claims priority benefit of European Application No. PCT/EP2013/002512, filed Aug. 21, 2013, the entire text of each of the above referenced disclosures being specifically incorporated herein by reference.

BACKGROUND OF THE INVENTION

The sequence listing that is contained in the file named "CRVCP0139USC1.txt", which is 52 KB (as measured in Microsoft Windows®) and was created on Mar. 29, 2019, is filed herewith by electronic submission and is incorporated by reference herein.

FIELD OF THE INVENTION

The invention relates to an RNA comprising at least one open reading frame (ORF) and comprising at least one modification, which increases the expression of the encoded peptide or protein. Furthermore, the invention relates to the medical use of such a modified RNA administered to a subject by jet injection. The invention relates further to a pharmaceutical composition and to a kit of parts comprising said modified RNA for administration by jet injection, preferably for use in the field of gene therapy and/or genetic vaccination. Additionally, the invention relates to a method for enhancing the (localized) expression of RNA-encoded peptides or proteins in the dermis or muscle (of a mammal) comprising administering the modified RNA by jet injection. And finally, the invention relates to a method of treatment comprising administering the modified RNA by jet injection to a subject in need thereof.

BACKGROUND OF THE INVENTION

Gene therapy and genetic vaccination belong to the most promising and quickly developing methods of modern medicine. They may provide highly specific and individual options for therapy of a large variety of diseases. Particularly, inherited genetic diseases but also autoimmune diseases, infectious diseases, cancerous or tumour-related diseases as well as inflammatory diseases may be the subject of such treatment approaches. Also, it is envisaged to prevent (early) onset of such diseases by these approaches.

The main conceptual rational behind gene therapy is appropriate modulation of impaired gene expression associated with pathological conditions of specific diseases. Pathologically altered gene expression may result in lack or overproduction of essential gene products, for example, signalling factors such as hormones, housekeeping factors, metabolic enzymes, structural proteins or the like. Altered gene expression may not only be due to mis-regulation of transcription and/or translation, but also due to mutations within the ORF coding for a particular protein. Pathological mutations may be caused by e.g. chromosomal aberration, or by more specific mutations, such as point mutations or frame-shift mutations, all of which may result in limited functionality and, potentially, total loss of function of the gene product. However, misregulation of transcription and/or translation may also occur, if mutations affect genes encoding proteins, which are involved in the transcriptional or translational machinery of the cell. Such mutations may lead to pathological up- or down-regulation of genes, which are—as such—functional. Genes encoding gene products, which exert such regulating functions, may be, for instance, transcription factors, signal receptors, messenger proteins or the like. However, loss of function of such genes encoding regulatory proteins may, under certain circumstances, be reversed by artificial introduction of other factors acting further downstream of the impaired gene product. Such gene defects may also be compensated by gene therapy via substitution of the affected gene itself.

As can be seen from the above, both methods, gene therapy and genetic vaccination, are essentially based on the administration of nucleic acid molecules to a patient and subsequent transcription and/or translation of the encoded genetic information.

DNA as well as RNA may be used as nucleic acid molecules for administration in the context of gene therapy or genetic vaccination. DNA is known to be relatively stable and easy to handle. However, the use of DNA bears the risk of undesired insertion of the administered DNA-fragments into the patient's genome potentially resulting in loss of function of the impaired genes. As a further risk, the undesired generation of anti-DNA antibodies has emerged. Another drawback is the limited expression level of the encoded peptide or protein that can be achieved by DNA administration and its subsequent transcription/translation. Among other factors, the presence of specific transcription factors, which regulate DNA transcription, has a major impact on the expression level of the administered DNA. In the absence of such factors, DNA transcription will not yield satisfying amounts of RNA. As a result, the level of translated peptide or protein obtained is limited.

By using RNA instead of DNA for gene therapy or genetic vaccination, the risk of undesired genomic integration and generation of anti-DNA antibodies is minimized or can be avoided altogether. However, RNA is considered to be a rather unstable molecular species. On the one hand, in the extracellular space, RNA is subject to degradation by almost ubiquitous RNAses. On the other hand, in vivo mRNA half-life in the cytoplasm is limited by the rate of enzymatic mRNA decay, which depends, at least in part, on cis-acting elements in the mRNA molecule. Thereby, controlled degradation of mRNA contributes to the fine regulation of eukaryotic gene expression (Friedel et al., Conserved principles of mammalian transcriptional regulation revealed by RNA half-life, Nucleic Acid Research, 2009, 1-12). Accordingly, each naturally occurring mRNA has its individual half-life depending on the gene, from which the mRNA is derived.

For many years it was generally accepted that mRNA is too unstable to be efficiently used for gene therapy purposes. In the last decade, however, several research groups faced this challenge and not only proved the feasibility of mRNA-mediated transfection with surprising results regarding transfection efficiency and duration of protein expression, but were also able to demonstrate major advantages over the use of pDNA. One of these advantages is the circumstance that mRNA does not need to cross the nuclear barrier for its encoded proteins to be expressed (reviewed in Tavernier et al., J Control Release. 2011 Mar. 30; 150(3):238-47. PMID: 20970469).

For gene therapy and genetic vaccination, modified and therefore stabilized RNA is usually more suitable than unmodified RNA, which is usually degraded quickly. On the one hand, the product encoded by the RNA-sequence is desired to accumulate in vivo. On the other hand, the RNA has to maintain its structural and functional integrity when prepared for a suitable dosage form, in the course of its storage, and when administered. Thus, considerable efforts were undertaken to provide stable RNA molecules for gene therapy or genetic vaccination in order to prevent them from being subject to early degradation or decay.

After introduction into the cell, the half-life of (non-stabilized) mRNA is limited. As a result, the production of protein encoded by this mRNA lasts for a few days maximally. Obviously, this fact limits the applicability of (non-stabilized) mRNA-based gene therapy. It cannot e.g. be used to correct hereditary diseases, because this would require repetitive administrations (reviewed in Tavernier et al., J Control Release. 2011 Mar. 30; 150(3):238-47. PMID: 20970469).

As mentioned above, mRNA is generally considered as a fairly unstable molecule, compared to DNA, especially once it reaches the cytoplasm where it is exposed to degrading enzymes. The main reason for its instability is the presence of a hydroxyl group on the second carbon atom of the sugar moiety, which, due to sterical hindrance, prevents mRNA from adopting a stable double β-helix structure and which makes the molecule more prone to hydrolytic degradation. Initial reports of intracellular mRNA delivery were subject to scepticism, mainly because of the belief that mRNA is extremely labile and could not withstand the transfection protocols.

As mentioned above, it is one of the advantages of RNA that it is sufficient for its expression to occur to deliver the RNA to the cytoplasm of a cell (in contrast to DNA, which has to cross the nuclear envelope). However, naked nucleic acid molecules do not enter cells efficiently because of their large size and hydrophilic nature due to negatively charged phosphate groups. In addition, they are very susceptible to nuclease-mediated degradation. Therefore, a challenge for gene therapy is to develop effective and safe means of RNA delivery to a cell.

In general, viral and non-viral delivery methods have been described (see, for example, Tavernier et al., J Control Release. 2011 Mar. 30; 150(3):238-47. PMID: 20970469). With respect to safety and process economy, non-viral methods are usually preferred. While some of these methods are based on the physical interruption of the cell membrane's barrier function, others employ cationic carrier molecules in order to facilitate gene transfer to targeted cells without degradation of the delivered gene.

First insight into the uptake mechanism of naked mRNA was gained by a mouse study investigating intradermal administration by injection. In this context, it could be shown that local entry into cells of the dermis turned out to be saturable, which means that only a defined protein level can be reached by intradermal injection of the mRNA. More elaborate work in vitro confirmed saturability of uptake and demonstrated that it is also temperature and dose dependent (reviewed in Schlake et al.; RNA Biology 9:11, 1-12; November 2012).

Thus far, intradermal injection is most frequently used for mRNA-based applications, allowing uptake of the mRNA by Langerhans' cells and dermal DCs after which transport to the draining lymph nodes is assumed (reviewed in Van Lint et al.; Human Vaccines & Immunotherapeutics 9:2, 248-257; February 2013). Other administration routes that have been used in order to deliver RNA, comprise intramuscular injection, intranodal injection (injection into a lymph node) and intratumoral injection.

It is evident not only from experiments using RNA as a vaccine that protein expression mediated by introduction of heterologous mRNA in vivo is generally possible and sufficient for raising a detectable immune response. However, raising an effective immune response and, even more, achieving a therapeutic effect by mRNA-mediated protein supply may be more demanding in terms of the required level of protein expression.

The efficient transfer of RNA into the cells of a subject thus still represents a bottleneck in the efficient expression of proteins introduced into the cell by means of heterologous RNA. The therapeutic effectiveness of RNA-based medicaments, particularly in the field of gene therapy, largely depends on the efficient expression of the gene products encoded in the therapeutic RNA molecule.

Therefore it is an object of the invention to improve the expression of the genetic information comprised in an RNA molecule, which is introduced into a cell or a tissue. Specifically, it is the object of the invention to improve the expression of a protein encoded in an RNA molecule, which is used for gene therapy or genetic vaccination and which is administered to a subject.

The object underlying the present invention is solved by the claimed subject matter.

SUMMARY OF THE INVENTION

The present invention provides an RNA comprising at least one open reading frame (ORF) and comprising at least one modification ("modified RNA"), which increases the expression of the encoded protein, for medical use, wherein the modified RNA is administered to a subject by jet injection. Specifically, the invention provides a modified RNA coding for at least one peptide or protein, whose expression is further increased by jet injection. Furthermore the invention provides a pharmaceutical composition and a kit of parts comprising said modified RNA for administration by jet injection, preferably for use in the field of gene therapy and/or genetic vaccination. Additionally, the present invention provides a method for increasing protein expression by jet injection of a respective RNA comprising at least one modification, which increases the expression of the protein encoded in that RNA.

In summary, the object of the present invention is solved by the provision of a modified RNA, wherein the expression of the encoded protein in a target tissue or in a target cell is additionally increased by jet injection.

BRIEF DESCRIPTION OF THE FIGURES

The figures shown in the following are merely illustrative and shall describe the present invention in a further way. These figures shall not be construed to limit the present invention thereto.

Guinea pigs were injected with 20 μg of modified mRNA encoding *Photinus pyralis* luciferase (PpLuc(GC)-muag-A64-C30-histoneSL) by jet injection or conventional intradermal needle injection. 24 h after injection, skin samples were prepared and luciferase expression was measured.

Figure 2:
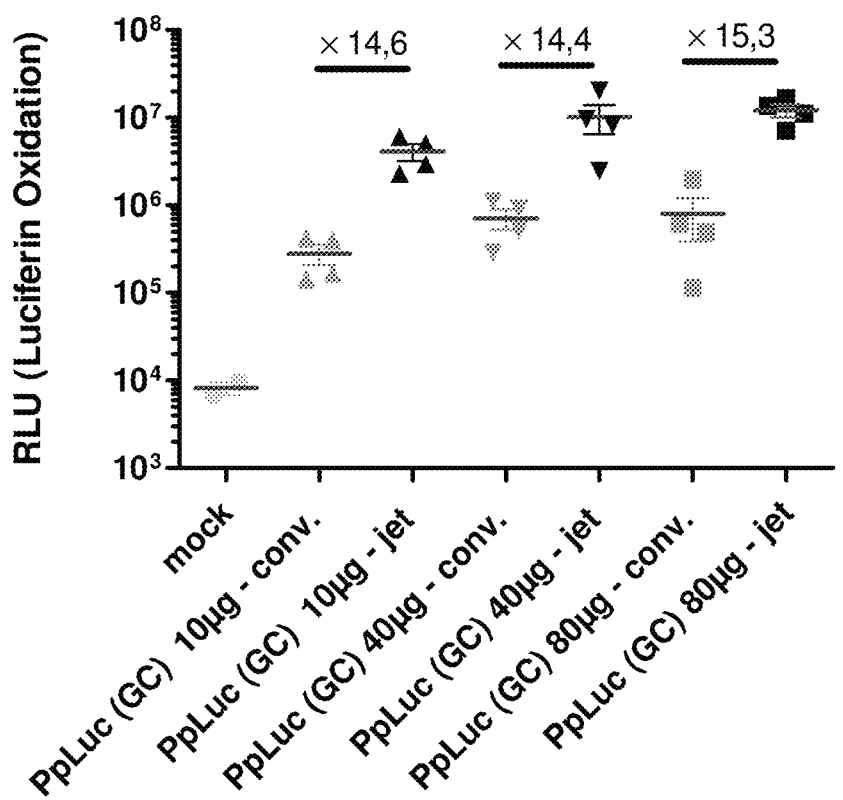

FIG. 2: Luciferase expression in guinea pigs

Guinea pigs were injected with different doses (10, 40 and 80 μg) of modified mRNA encoding *Photinus pyralis* luciferase (PpLuc(GC)-muag-A64-C30-histoneSL) by jet injection or conventional intradermal needle injection. 24 h after injection, skin samples were prepared and luciferase expression was measured.

Figure 3:
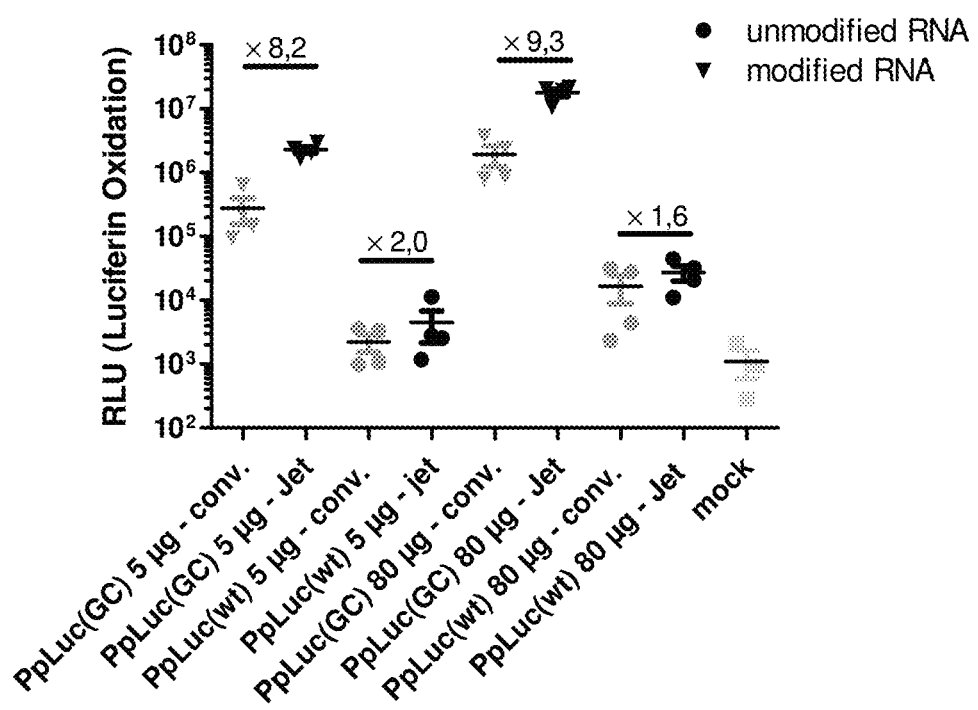

FIG. 3: Comparison of unmodified and modified mRNA

Guinea pigs were injected with different doses (5 and 80 μg) of unmodified mRNA (PpLuc(wt)-A30) and modified mRNA (PpLuc(GC)-muag-A64-C30-histoneSL) encoding *Photinus pyralis* luciferase by jet injection or conventional intradermal needle injection. 24 h after injection, skin samples were prepared and luciferase expression was measured.

FIG. 4: mRNA sequence R1265: PpLuc(GC)-muag-A64-C30-histoneSL (SEQ ID NO: 46)

FIG. 5: mRNA sequence R2652: PpLuc(wt)-A30 (SEQ ID NO: 47)

FIG. 6: mRNA sequence R3454: PpLuc(wt)-A64 (SEQ ID NO: 48)

FIG. 7: mRNA sequence R2462: PpLuc(GC)-A64-C30-HistoneSL (SEQ ID NO: 49)

FIG. 8: mRNA sequence R1256: PpLuc(GC)-muag-A64-C30 (SEQ ID NO: 50)

FIG. 9: mRNA sequence R2393: PpLuc(nat)-muag-A64-C30-HistoneSL (SEQ ID NO: 51)

FIG. 10: mRNA sequence R2403: RAV-G(GC)-muag-A64-C30-histoneSL (SEQ ID NO: 52)

FIG. 11: mRNA sequence R3513: EPO(wt)-A30 (SEQ ID NO: 53)

FIG. 12: mRNA sequence R3135: HSD17B4-EPO(GC)-albumin7-A64-C30-histoneSL (SEQ ID NO: 54)

Figure 13:
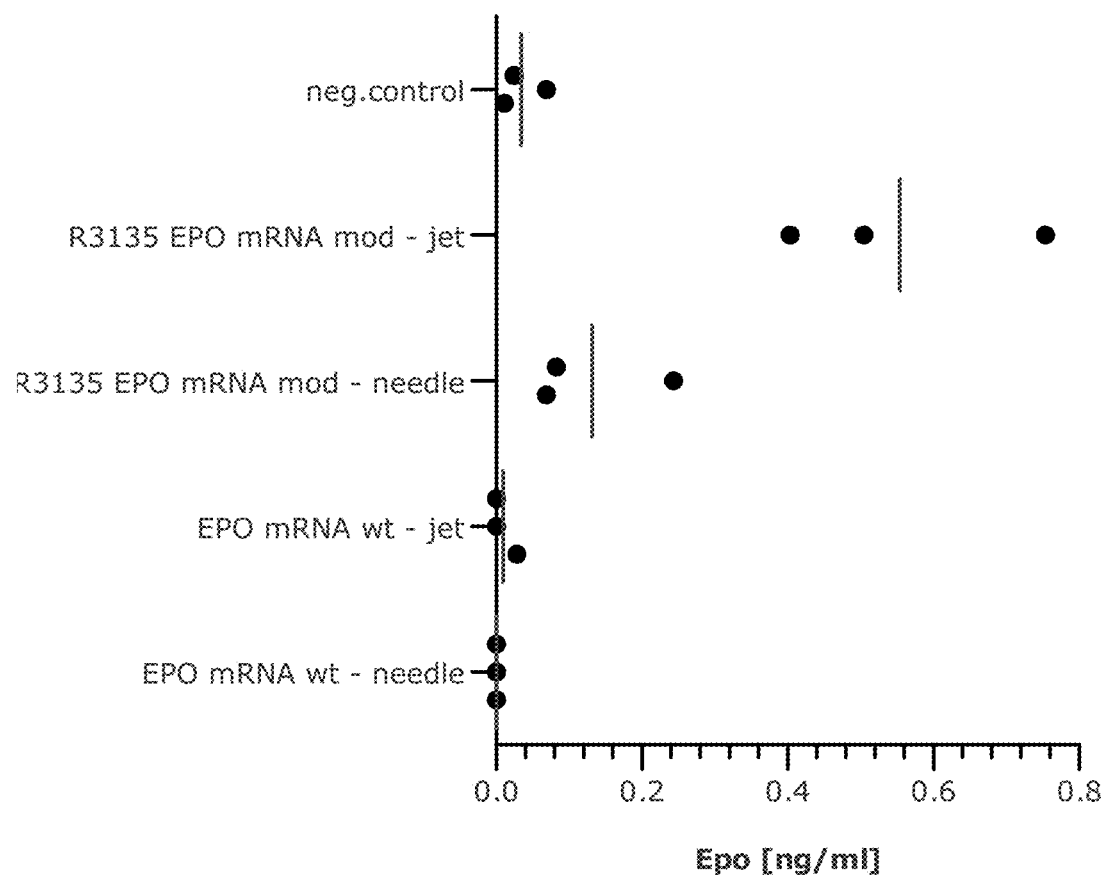

FIG. 13: Comparison of unmodified and modified mRNA coding for Erythropoetin (EPO)

Guinea pigs were injected with unmodified mRNA (R3513: EPO(wt)-A30) or modified mRNA (HSD17B4-EPO(GC)-albumin7-A64-C30-histoneSL) encoding Erythropoetin (EPO) by jet injection or conventional intradermal needle injection. Each animal was injected at 3 sites with 80 μg of RNA per injection site. 24 h after injection, blood was sampled and EPO expression was measured as described in Example 5.

FIG. 14: G/C optimized mRNA sequence R2510 (SEQ ID NO: 64) coding for RSV-F protein of the RSV long strain (RSV-F long) as comprised in the RSV-F mRNA vaccine.

FIGS. 15A-B: Comparison of conventional syringe-needle injection and jet injection of an RSV mRNA vaccine (antibody titers).

Female guinea pigs (n=8/group) were intradermally (i.d.) injected with the RSV-F mRNA vaccine (80 μg of R2510), either 1×100 μl with conventional needle injection (i.d.), 4×25 μl with needle injection (i.d.), or 1×100 μl with jet injection (i.d.). A control group (n=2) was needle-injected intramuscularly (i.m.) with 20 μg of inactivated RSV long (2×50 μl). All animals received boost injections on days 14 and 28. Blood samples were collected on day −3 (three days before the first vaccination) and on days 7, 21 and 42 for the determination of anti-RSV F antibody titers. The experiment was performed as described in Example 4.

Figure 15:
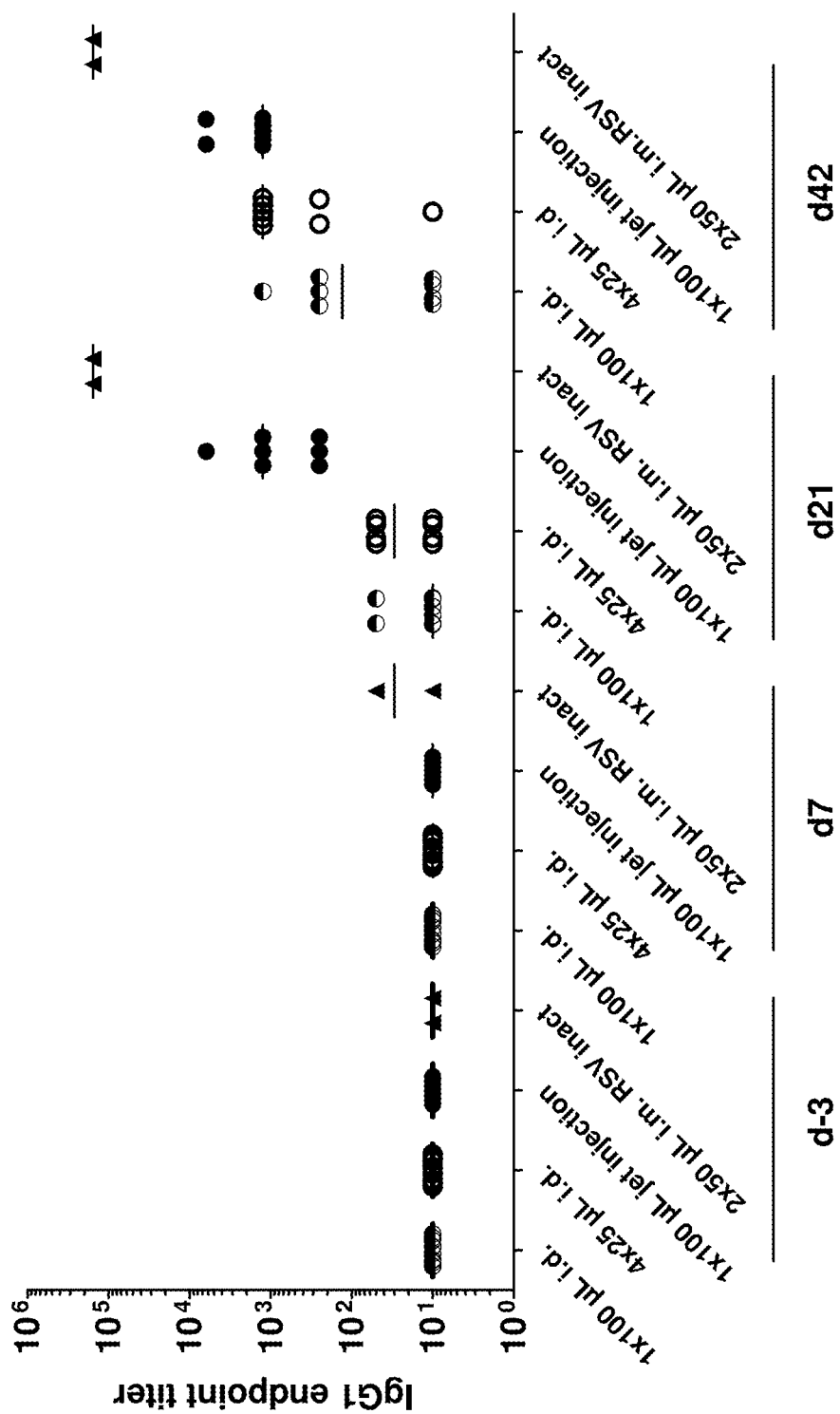
Figure 15:
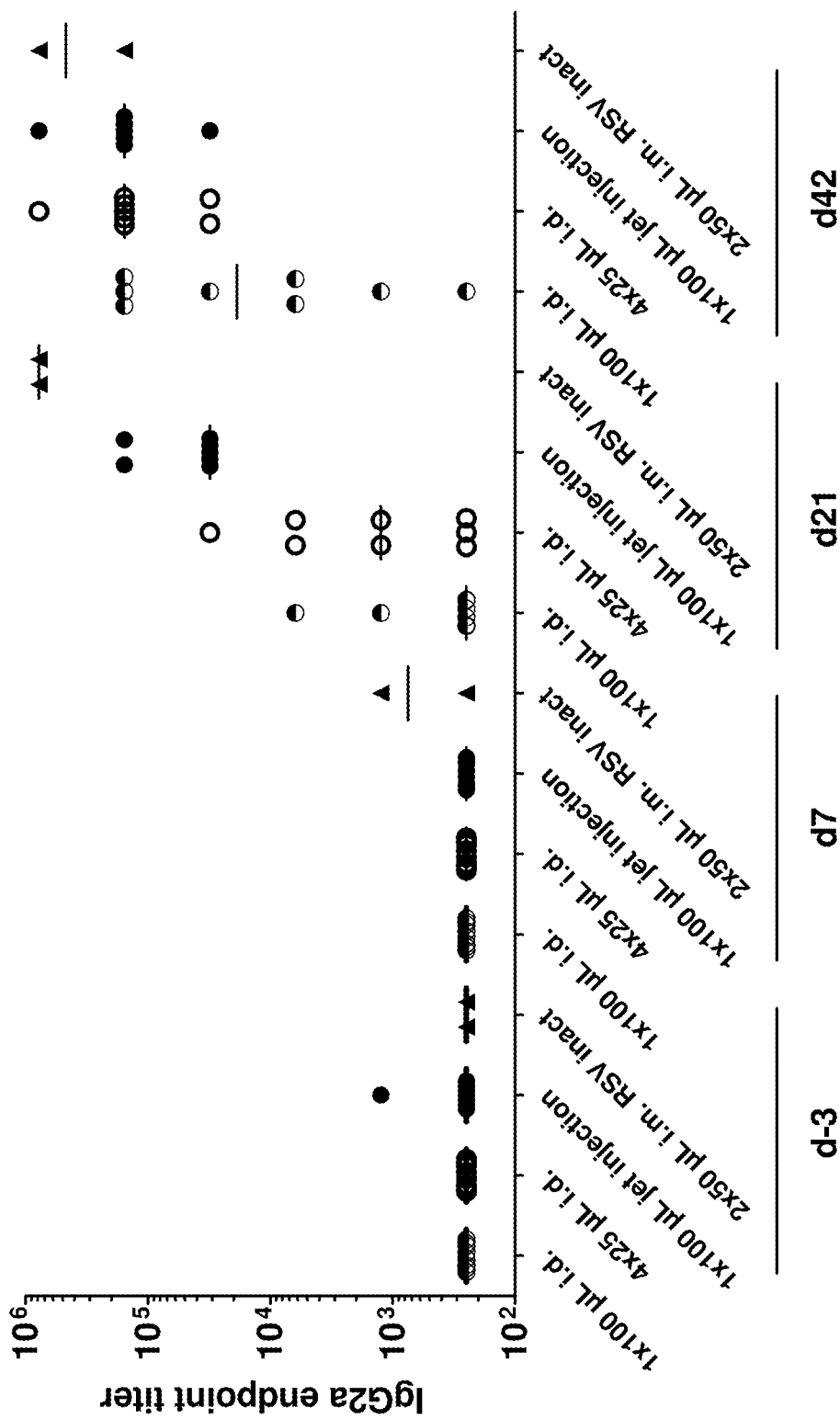

FIG. 15 A: IgG1 endpoint titers determined by ELISA.

FIG. 15 B: IgG2a endpoint titers as determined by ELISA.

As can be seen, the RSV-F mRNA vaccine already induced anti-F protein antibodies of the IgG subclass (A) and the IgG2a subclass (B) on day 21 (one week after the first boost vaccination on day 14) when the vaccine was administered by jet injection (1×100 al). Comparable antibody titers were only reached on day 42 (two weeks after the second boost vaccination on day 28) when the vaccine was administered by conventional needle injection (4×25 al).

Figure 16:
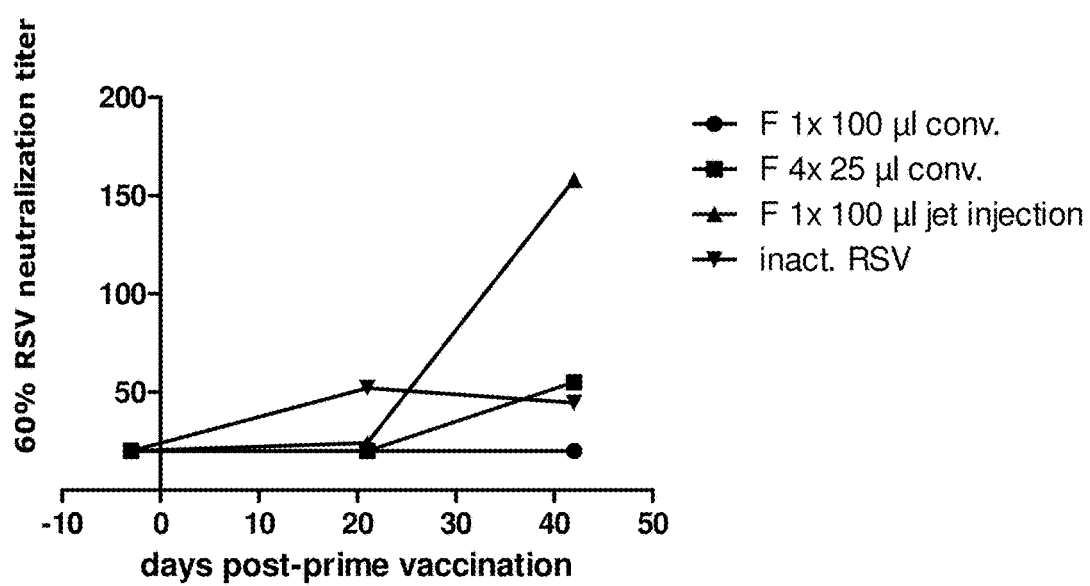

FIG. 16: Comparison of conventional syringe-needle injection and jet injection of an RSV mRNA vaccine (virus neutralization titers).

The experiment was performed as described in Example 4. Virus neutralizing titers (VNTs) were determined by plaque reduction assay on days −3, 21 and 42. Median VNTs are plotted over time. VNTs are indicated as reciprocal neutralizing antibody titers at 60% reduction end-point of the virus control. As can be seen, significant RSV neutralization titers were measured on day 42 only when the vaccine was administered by jet injection (1×100 al).

For the sake of clarity and readability the following definitions are provided. Any technical feature mentioned for these definitions may be read on each and every embodiment of the invention. Additional definitions and explanations may be specifically provided in the context of these embodiments. Where nucleic acid sequences are reported in the context of the present invention, these sequences generally comprise both, the specific RNA or DNA sequence as well as its corresponding DNA or RNA counterpart, respectively. For example, where a DNA sequence is provided, the skilled person knows that the corresponding RNA sequence is obtained by exchange of thymine by uracil residues and vice versa.

Gene Therapy:

Gene therapy may typically be understood to mean a treatment of a patient's body or isolated elements of a patient's body, for example isolated tissues/cells, by nucleic acids encoding a peptide or protein. It typically may comprise at least one of the steps of a) administration of a nucleic acid, preferably an RNA molecule as defined herein, directly to the patient—by whatever administration route—or in vitro to isolated cells/tissues of the patient, which results in transfection of the patient's cells either in vivo/ex vivo or in vitro; b) transcription and/or translation of the introduced nucleic acid molecule; and optionally c) re-administration of isolated, transfected cells to the patient, if the nucleic acid has not been administered directly to the patient.

Genetic Vaccination:

Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an RNA molecule as defined herein, to a subject, preferably a patient, or to isolated cells of a subject, preferably a patient, which usually results in transfection of the subject's cells either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Immune System:

The immune system may protect organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so-called humoral and cellular components.

Adaptive Immune System:

The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Innate Immune System:

The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. The pharmaceutical composition according to the present invention may comprise one or more such substances. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Immune Response:

An immune response may typically be a specific reaction of the adaptive immune system to a particular antigen (so-called specific or adaptive immune response) or an unspecific reaction of the innate immune system (so-called unspecific or innate immune response), or a combination thereof.

Adaptive Immune Response:

The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs, through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T-cells. Therein, presenting the antigen on MHC molecules leads to activation of T cells which induces their proliferation and differentiation into armed effector T cells. The most important function of effector T cells is the killing of infected cells by CD8+ cytotoxic T cells and the activation of macrophages by Th1 cells which together make up cell-mediated immunity, and the activation of B cells by both Th2 and Th1 cells to produce different classes of antibody, thus driving the humoral immune response. T cells recognize an antigen by their T cell receptors which do not recognize and bind the antigen directly, but instead recognize short peptide fragments e.g. of pathogen-derived protein antigens, e.g. so-called epitopes, which are bound to MHC molecules on the surfaces of other cells.

Cellular Immunity/Cellular Immune Response:

Cellular immunity relates typically to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens and stimulation of cells to secrete a variety of cytokines that influence the function of other cells involved in adaptive immune responses and innate immune responses.

Immunogen:

In the context of the present invention an immunogen may be typically understood to be a compound that is able to stimulate an immune response. Preferably, an immunogen is a peptide, polypeptide, or protein. In a particularly preferred embodiment, an immunogen in the sense of the present invention is the product of translation of a provided nucleic acid molecule, preferably an artificial nucleic acid molecule as defined herein. Typically, an immunogen elicits at least an adaptive immune response.

Antigen:

In the context of the present invention "antigen" refers typically to a substance, which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein which may be presented by the MHC to T-cells.

Epitope:

Epitopes (also called 'antigen determinant') can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence.

These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context, antigenic determinants can be conformational or discontinuous epitopes, which are composed of segments of the proteins or peptides as defined herein that are discontinuous in the amino acid sequence of the proteins or peptides as defined herein, but are brought together in the three-dimensional structure or continuous or linear epitopes, which are composed of a single polypeptide chain.

Adjuvant/Adjuvant Component:

An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Protein:

A protein typically comprises one or more peptides or polypeptides. A protein is typically folded into 3-dimensional form, which may be required for the protein to exert its biological function.

Peptide:

A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Fragment or Part of a Protein:

Fragments or parts of a protein in the context of the present invention are typically understood to be peptides corresponding to a continuous part of the amino acid sequence of a protein, preferably having a length of about 6 to about 20 or even more amino acids, e.g. parts as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. Fragments or parts of the proteins as defined herein may also comprise epitopes or functional sites of those proteins. Preferably, fragments or parts of a proteins in the context of the invention are antigens, particularly immunogens, e.g. antigen determinants (also called 'epitopes'), or do have antigenic characteristics, eliciting an adaptive immune response. Therefore, fragments of proteins or peptides may comprise at least one epitope of those proteins or peptides. Furthermore, also domains of a protein, like the extracellular domain, the intracellular domain or the transmembrane domain, and shortened or truncated versions of a protein may be understood to comprise a fragment of a protein.

Pharmaceutically Effective Amount:

A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Sequence Identity:

Two or more sequences are identical if they exhibit the same length and order of nucleotides or amino acids. The percentage of identity typically describes the extent, to which two sequences are identical, i.e. it typically describes the percentage of nucleotides that correspond in their sequence position with identical nucleotides of a reference sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Fragment of a Sequence:

A fragment of a sequence may typically be a shorter portion of a full-length sequence of e.g. a nucleic acid molecule or an amino acid sequence. Accordingly, a fragment, typically, consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 30%, more preferably at least 40%, more preferably at least 50%, even more preferably at least 60%, even more preferably at least 70%, and most preferably at least 80% of the total (i.e. full-length) molecule, from which the fragment is derived.

Sequence of a Nucleic Acid Molecule:

The sequence of a nucleic acid molecule is typically understood to be the particular and individual order, i.e. the succession, of its nucleotides. The sequence of a protein or peptide is typically understood to be the order, i.e. the succession, of its amino acids.

Stabilized Nucleic Acid Molecule:

A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Heterologous Sequence:

Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Nucleic Acid Molecule:

A nucleic acid molecule is a molecule comprising, preferably consisting of, nucleic acid components. The term nucleic acid molecule preferably refers to DNA or RNA molecules. It is preferably used synonymously with the term "polynucleotide". Preferably, a nucleic acid molecule is a polymer comprising or consisting of nucleotide monomers, which are covalently linked to each other by phosphodiester bonds of a sugar/phosphate-backbone.

Open Reading Frame:

An open reading frame (ORF) in the context of the invention may typically be a sequence of several nucleotide triplets, which may be translated into a peptide or protein. An open reading frame preferably contains a start codon, i.e. a combination of three subsequent nucleotides coding usually for the amino acid methionine (ATG or AUG), at its 5'-end and a subsequent region, which usually exhibits a length, which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG or AUG) and which preferably terminates with a stop codon (e.g., TAA, TGA, or TAG or UAA, UAG, UGA, respectively). The open reading frame may be isolated or it may be incorporated in a longer nucleic acid sequence, for example in a vector or an mRNA. An open reading frame may also be termed 'protein coding region'.

DNA:

DNA is the usual abbreviation for deoxy-ribonucleic-acid. It is a nucleic acid molecule, i.e. a polymer consisting of nucleotides. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA-sequence. DNA may be single stranded or double stranded. In the double stranded form, the nucleotides of the first strand typically hybridize with the nucleotides of the second strand, e.g. by A/T-base-pairing and G/C-base-pairing.

RNA, mRNA:

RNA is the usual abbreviation for ribonucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers, which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino acid sequence of a particular peptide or protein. Typically, a mature mRNA comprises a 5'-cap, optionally a 5'UTR, an open reading frame, optionally a 3'UTR and a poly(A) sequence. Aside from messenger RNA, several non-coding types of RNA exist which may be involved in regulation of transcription and/or translation. The term "RNA" further encompass other coding RNA molecules, such as viral RNA, retroviral RNA and replicon RNA.

Bicistronic RNA, Multicistronic RNA:

A bicistronic or multicistronic RNA is typically an RNA, preferably an mRNA, that typically may have two (bicistronic) or more (multicistronic) open reading frames (ORF). An open reading frame in this context is a sequence of codons that is translatable into a peptide or protein.

G/C Modified:

A G/C-modified nucleic acid may typically be a nucleic acid, preferably an RNA molecule as defined herein, based on a modified wild-type sequence comprising a preferably increased number of guanosine and/or cytosine nucleotides as compared to the wild-type sequence. Such an increased number may be generated by substitution of codons containing adenosine or thymidine nucleotides by codons containing guanosine or cytosine nucleotides. If the enriched G/C content occurs in a coding region of DNA or RNA, it makes use of the degeneracy of the genetic code. Accordingly, the codon substitutions preferably do not alter the encoded amino acid residues, but exclusively increase the G/C content of the nucleic acid molecule.

5'-cap:

A 5'-cap is an entity, typically a modified nucleotide entity, which generally 'caps' the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. The naturally occurring 5'-CAP is m7GpppN.

Immunostimulatory RNA:

An immunostimulatory RNA (isRNA) in the context of the invention may typically be an RNA that is able to induce an innate immune response. It usually does not have an open reading frame and thus does not provide a peptide-antigen or immunogen but elicits an immune response, e.g. by binding to a specific kind of Toll-like-receptor (TLR) or other suitable receptors. However, of course also mRNAs having an open reading frame and coding for a peptide/protein may induce an innate immune response and, thus, may be immunostimulatory RNAs.

Poly(A) Sequence:

A poly(A) sequence, also called poly(A) tail or 3'-poly(A) tail, is typically understood to be a sequence of adenine nucleotides, e.g., of up to about 400 adenine nucleotides, e.g. from about 20 to about 400, preferably from about 50 to about 400, more preferably from about 50 to about 300, even more preferably from about 50 to about 250, most preferably from about 60 to about 250 adenine nucleotides. A poly(A) sequence is typically located at the 3' end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

Polyadenylation:

Polyadenylation is typically understood to be the addition of a poly(A) sequence to a nucleic acid molecule, such as an RNA molecule, e.g. to a premature mRNA. Polyadenylation may be induced by a so-called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called pre-mature-mRNA). Typically, RNA maturation (from pre-mRNA to mature mRNA) comprises the step of polyadenylation.

3'-Untranslated Region (3'UTR):

A 3'UTR is typically the part of an mRNA which is located between the protein coding region (i.e. the open reading frame) and the poly(A) sequence of the mRNA. A 3'UTR of the mRNA is not translated into an amino acid sequence. The 3'UTR sequence is generally encoded by the gene, which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'capping, splicing the pre-mature mRNA to excise optional introns and modifications of the 3'-end, such as polyadenylation of the 3'-end of the pre-mature mRNA and optional endo-/or exonuclease cleavages etc. In the context of the present invention, a 3'UTR corresponds to the sequence of a mature mRNA, which is located 3' to the stop codon of the protein coding region, preferably immediately 3' to the stop codon of the protein coding region, and which extends to the 5'-side of the poly(A) sequence, preferably to the nucleotide immediately 5' to the poly(A) sequence. The term "corresponds to" means that the 3'UTR sequence may be an RNA sequence, such as in the mRNA sequence used for defining the 3'UTR sequence, or a DNA sequence, which corresponds to such RNA sequence. In the context of the present invention, the term "a 3'UTR of a gene", such as "3'UTR of alpha or beta globine", is the sequence, which corresponds to the 3'UTR of the mature mRNA derived from this gene, i.e. the mRNA obtained by transcription of the gene and maturation of the pre-mature mRNA. The term "3'UTR of a gene" encompasses the DNA sequence and the RNA sequence of the 3'UTR.

5'-Untranslated Region (5'UTR):

A 5'-UTR is typically understood to be a particular section of messenger RNA (mRNA). It is located 5' of the open reading frame of the mRNA. Typically, the 5'UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites or a 5'-Terminal Oligopyrimidine Tract. The 5'UTR may be posttranscriptionally modified, for example by addition of a 5'-cap. In the context of the present invention, a 5'UTR corresponds to the sequence of a mature mRNA which is located between the 5'cap and the start codon. Preferably, the 5'UTR corresponds to the sequence, which extends from a nucleotide located 3' to the 5'-cap, preferably from the nucleotide located immediately 3' to the 5'cap, to a nucleotide located 5' to the start codon of the protein coding region, preferably to the nucleotide located immediately 5' to the start codon of the protein coding region. The nucleotide located immediately 3' to the 5'cap of a mature mRNA typically corresponds to the transcriptional start site. The term "corresponds to" means that the 5'UTR sequence may be an RNA sequence, such as in the mRNA sequence used for defining the 5'UTR sequence, or a DNA sequence which corresponds to such RNA sequence. In the context of the present invention, the term "a 5'UTR of a gene", is the sequence, which corresponds to the 5'UTR of the mature mRNA derived from this gene, i.e. the mRNA obtained by transcription of the gene and maturation of the pre-mature mRNA. The term "5'UTR of a gene" encompasses the DNA sequence and the RNA sequence of the 5'UTR.

5'Terminal Oligopyrimidine Tract (TOP): The 5'terminal oligopyrimidine tract (TOP) is typically a stretch of pyrimidine nucleotides located at the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence, which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'end with a cytosine nucleotide. In TOP genes and TOP mRNAs, the TOP-motif preferably starts at its 5'end with the transcriptional start site and ends one nucleotide 5' to the first purin residue in said gene or mRNA. A TOP motif in the sense of the present invention is preferably located at the 5'end of a sequence, which represents a 5'UTR, or at the 5'end of a sequence, which codes for a 5'UTR. Thus, preferably, a stretch of 3 or more pyrimidine nucleotides is called "TOP motif" in the sense of the present invention if this stretch is located at the 5'end of a respective sequence, such as the modified RNA according to the invention, the 5'UTR element of the modified RNA according to the invention, or the nucleic acid sequence, which is derived from the 5'UTR of a TOP gene as described herein. In other words, a stretch of 3 or more pyrimidine nucleotides, which is not located at the 5'-end of a 5'UTR or a 5'UTR element, but anywhere within a 5'UTR or a 5'UTR element is preferably not referred to as "TOP motif".

Top Gene:
TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'-CAP to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363, SEQ ID NO. 1395, SEQ ID NO. 1421 and SEQ ID NO. 14221-1363 of the patent application PCT/EP2012/002448WO2013/143700 or homologs or variants thereof, whose disclosure is incorporated herewith by reference. In this context, a particularly preferred fragment of a 5'UTR of a TOP gene is a 5'UTR of a TOP gene lacking the 5'TOP motif. The term '5'UTR of a TOP gene' preferably refers to the 5'UTR of a naturally occurring TOP gene.

Unmodified Reference RNA:
RNA corresponding to the wild type RNA sequence as it is present in nature. For example, an unmodified reference mRNA corresponds to an mRNA sequence comprising naturally occuring nucleotides, including nucleotides comprising naturally occuring modifications, and/or naturally occuring untranslated regions, such as the naturally occuring 5'-CAP structure m7GpppN, optionally the naturally occuring 5'-UTR, if present in the naturally occuring mRNA sequence, the wild type open reading frame, optionally the naturally occuring 3'-UTR if present in the naturally occurring mRNA sequence and a poly A sequence with approximately 30 adenosines.

Transfection:
The term 'transfection' refers to the introduction of nucleic acid molecules, such as DNA or RNA (e.g. mRNA) molecules, into cells, preferably into eukaryotic cells. In the context of the present invention, the term 'transfection' encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Carrier/Polymeric Carrier:
A carrier in the context of the invention may typically be a compound that facilitates transport and/or complexation of another compound (cargo). A polymeric carrier is typically a carrier that is formed of a polymer. A carrier may be associated to its cargo by covalent or non-covalent interaction. A carrier may transport nucleic acids, e.g. RNA or DNA, to the target cells. The carrier may—for some embodiments—be a cationic component.

Cationic Component:
The term "cationic component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic component may be any positively charged compound or polymer, preferably a cationic peptide or protein which is positively charged under physiological conditions, particularly under physiological conditions in vivo. A 'cationic peptide or protein' may contain at least one positively charged amino acid, or more than one positively charged amino acid, e.g. selected from Arg, His, Lys or Orn. Accordingly, 'polycationic' components are also within the scope exhibiting more than one positive charge under the conditions given.

Vaccine:
A vaccine is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response.

Vehicle:

A vehicle is typically understood to be a material that is suitable for storing, transporting, and/or administering a compound, such as a pharmaceutically active compound. For example, it may be a physiologically acceptable liquid which is suitable for storing, transporting, and/or administering a pharmaceutically active compound.

DETAILED DESCRIPTION OF THE INVENTION

In a first aspect, the present invention provides a modified ribonucleic acid (RNA) comprising at least one open reading frame (ORF) coding for at least one peptide or protein, wherein the RNA comprises at least one modification, which increases the expression of its encoded protein or peptide. The expression of said encoded protein or peptide is further increased by administration of the modified RNA by jet injection. In this context the increase in protein production due to the at least one modification of the RNA is referred to herein as "modification-associated increase of protein expression".

The increase in protein production due to jet injection of the RNA is referred to herein as "injection-associated increase of protein expression", independently if modified RNA or an unmodified reference RNA is used.

The term 'modification-associated increase of protein expression' either refers to a situation, where the total amount of protein that is produced from the modified RNA measured for a specific time period is increased in comparison to the total amount of protein produced from an unmodified reference RNA lacking the modification or to a situation, where the protein level that is produced from the modified RNA measured for a specific time point is increased in comparison to the protein level produced from an unmodified reference RNA lacking the modification.

The term 'injection-associated increase of protein expression' refers to a situation, where the total amount of protein that is produced from an RNA administered via jet injection measured for a specific time period is increased in comparison to the total amount of protein produced from the same RNA administered by conventional needle injection or to a situation, where the protein level that is produced from an RNA administered via jet injection measured for a specific time point is increased in comparison to the protein level produced from the same RNA administered by conventional needle injection.

According to the invention, the at least one modification of the modified RNA and the administration by jet injection have a synergistic effect on the expression of the protein or peptide encoded by the modified RNA. In other terms, the expression increase that is obtained by using jet injection in order to administer the modified RNA to a subject/tissue compared to the expression that is obtained by using conventional needle injection in order to administer an unmodified reference RNA to a subject/tissue is larger than the sum of the expression increase obtained by using modified RNA as compared to an unmodified reference RNA, wherein both are administered in the same manner ("modification-associated increase of protein expression") and the expression increase obtained for an (unmodified) RNA administered by jet injection as compared to the same (unmodified) RNA administered by means other than jet injection, particularly by conventional needle injection ("injection-associated increase of protein expression").

In this context the inventors surprisingly found out that administration of a modified RNA, which comprises at least one modification which increases the protein expression of the encoded protein, by jet injection increased the expression of the encoded protein much more than expected. It was expected that administration by jet injection would have the same effect on protein expression for a modified RNA and for an unmodified reference RNA.

In the context of the present invention, the "modification-associated protein expression" may be increased at a specific time point after initiation of expression or total protein production over a certain time period after initiation of expression may be increased when compared to an unmodified reference RNA. Thus, the protein level observed at a certain time point after initiation of expression (or after injection, respectively, of the modified RNA), for example, 6, 12, 24, 48, or 72 hours post injection, or the total amount of protein produced in a time span of, e.g. 6, 12, 24, 48 or 72 hours, is preferably higher than the protein level observed at the same time point after initiation of expression (or after injection) or the total protein amount produced within the same time span for an unmodified reference RNA.

Preferably, the modification of RNA alone (i.e. without administration of the modified RNA by jet injection, but using, for instance, conventional needle injection) leads to an expression of the encoded protein, which is at least 1.5-fold, more preferably at least 2-fold, more preferably at least 5-fold, even more preferably at least 10-fold, most preferably at least 50-fold of the protein production observed for a corresponding, unmodified reference RNA.

The "injection-associated protein expression" may be increased at a specific time point after initiation of expression (after injection of the RNA) or total protein production over a certain time period after initiation of expression may be increased when compared to the conventional needle injection of the RNA. Thus, the protein level observed at a certain time point after initiation of expression (or after injection, respectively of the RNA), for example, 6, 12, 24, 48, or 72 hours post injection, or the total amount of protein produced in a time span of, e.g. 6, 12, 24, 48 or 72 hours, is preferably higher than the protein level observed at the same time point after initiation of expression (or after injection) or the total protein amount produced within the same time span for the same RNA injected by a conventional method as for example by needle injection.

Preferably, jet injection increases the protein production from an unmodified reference RNA only to a minor extent e.g. 1.5-fold or 2-fold.

According to the invention, the expression of a protein encoded by an RNA comprising at least one modification and comprising at least one open reading frame is further increased (in a synergistic manner) by jet injection. Thus, protein expression is further increased in comparison to a reference, such as an RNA having the same modification that is administered by conventional needle injection. Preferably, the protein production obtained by jet injection of the modified RNA according to the invention is increased at least 5-fold, more preferably 10-fold, even more preferably 50-fold and even more preferably 100-fold as compared to an unmodified reference RNA that is administered by conventional means, in particular conventional needle injection. Therefore, the increase in protein production obtained by jet injection of the modified RNA according to the invention is at least 1.5-fold, more preferably at least 2-fold, more preferably at least 3-fold, more preferably at least 4-fold, even more preferably at least 5-fold and most preferably at least 10-fold as compared to the increase in protein expression obtained by jet injection of an unmodified reference RNA. Preferably, this holds true for the protein production at a given time point post initiation of expression or for total protein production in a given time period, for example in a time period of 6, 12, 24, 48 or 72 hours post initiation of expression or post injection of the RNA.

The term "jet injection", as used herein, refers to a needle-free injection method, wherein a fluid containing at least one modified RNA and, optionally, further suitable excipients is forced through an orifice, thus generating an ultra-fine liquid stream of high pressure that is capable of penetrating mammalian skin and, depending on the injection settings, subcutaneous tissue or muscle tissue. In principle, the liquid stream forms a hole in the skin, through which the liquid stream is pushed into the target tissue. Preferably, jet injection is used for intradermal, subcutaneous or intramuscular injection of the modified RNA according to the invention.

The target tissue or rather the layer of tissue, to which the fluid is delivered by jet injection, depends on several parameters such as the specific characteristics of the liquid stream that is employed as well as the physical parameters defining the particular type of skin (and underlying tissue), to which the fluid is administered. For instance, the density of collagen fibers and the overall elasticity of the tissue to be treated may have an influence on the penetration achieved by the liquid jet. Several physical parameters have an influence on the result obtained by jet injection. Distinct layers of tissue, which are separated by mechanical barriers (such as the superficial fascia), can be specifically addressed by selecting a liquid stream that is suitable for penetrating deep enough into the skin or underlying tissue without penetrating said mechanical barrier, which is positioned underneath the addressed layer. E.g., intradermal administration is achieved by application of a liquid stream that penetrates into the dermis without disrupting the superficial fascia. The administered fluid distributes in the dermis horizontally.

Several parameters defining the liquid jet may have an impact on the efficiency of the injection and, in particular, on the depth of penetration, which translates into targeting a certain tissue layer, respectively. One such parameter is the pressure, with which the liquid stream hits the skin surface. That pressure is dependent, amongst other factors, on the jet exit velocity (i.e. the velocity, at which the jet leaves the nozzle of the injection apparatus) as well as on the distance between the nozzle and the skin and the medium (air, liquid) that constitutes the space between nozzle and skin. Typically, the velocity of the jet (and the pressure exerted by the jet) is reduced as the jet exits from the nozzle and crosses said space. The penetration of the skin further depends on the jet diameter, which is primarily determined by the dimensions of the nozzle, which is employed. Notably, comparable results in terms of tissue penetration and fluid delivery may be obtained by different combinations of parameters.

In order to penetrate the skin, the jet exit velocity of the liquid stream comprising the RNA is preferably at least 60 m/s, more preferably at least 80 m/s, even more preferably at least 100 m/s and most preferably at least 150 m/s.

The liquid stream comprising the RNA that is used in jet injection is typically very fine and is selected such that penetration of the skin is feasible. Preferably, the liquid jet diameter is selected in accordance with the desired target tissue. The liquid jet diameter is preferably regulated by the nozzle orifice, i.e. the liquid jet diameter increases with increasing diameter of the nozzle orifice. Preferably, the liquid jet diameter corresponds to the orifice diameter so that the liquid jet diameter is equal or slightly larger than the diameter of the nozzle orifice. Typically, at constant jet exit velocity, the penetration depth achieved in the tissue will be higher for greater liquid jet diameters.

In one embodiment of the invention, the diameter of the orifice is between 20 µm and 600 µm, preferably between 100 µm and 300 µm, more preferably between 120 µm and 250 m.

In a further preferred embodiment, the diameter of the orifice is between 20 µm and 150 am, preferably between 30 µm and 130 µm, more preferably between 40 µm and 110 µm, even more preferably between 50 µm and 100 m.

In another embodiment, the diameter of the orifice is between 70 µm and 300 µm, preferably between 80 µm and 200 µm, more preferably between 90 µm and 180 µm, even more preferably between 100 µm and 150 µm.

Preferably, the injection time (i.e. the time between the first contact of the jet with the target skin and the time point of jet cessation) is less than 1.0 seconds, more preferably less than 0.7 seconds and even more preferably less than 0.3 seconds. Most preferably the injection time is less than 0.1 second.

In a preferred embodiment, the process of jet injection comprises at least two phases characterized by different jet velocities. Preferably, jet injection begins with a first phase, wherein a first jet velocity is selected so as to ensure tissue penetration. Said first jet velocity is dependent to a large extent on the exit jet velocity, i.e. the velocity, at which the liquid jet leaves the device's nozzle. Said first velocity is further adapted to the desired injection depth. Subsequently, a second jet velocity is employed in a second phase, which is appropriate to deliver the fluid into the target tissue. Said second jet velocity is typically lower than the first velocity and is chosen as to not exceed the absorption capacity of the tissue.

In a preferred embodiment, the jet injection of the modified RNA according to the invention comprises three phases:

The initial penetration phase is characterized by the highest pressure with respect to the pressure profile of the whole jet injection process (therefore also referred to as peak pressure phase). The penetration phase preferably lasts less than 50 ms, more preferably less than 10 ms, even more preferably less than 5 ms. Most preferably the penetration phase lasts less than 1 ms.

After the peak pressure phase, the pressure is reduced in the delivery phase, while maintaining a level sufficient for injecting the liquid stream into the target tissue. It is preferred that the pressure level is constant or decreases only slowly during the delivery phase. Preferably, the delivery phase lasts less than 0.8 seconds, more preferably less than 0.5 seconds, even more preferably the delivery phase lasts from 0.01 to 0.3 seconds, most preferably from 0.01 to 0.1 seconds.

The final stage of the jet injection process according to this embodiment of the invention is characterized by a drop of the pressure acting on the liquid comprising the modified RNA to levels around the atmospheric pressure level (drop-off phase). Typically, the pressure drops abruptly after the delivery phase. The drop-off phase preferably lasts less than 0.3 seconds, more preferably less than 0.2 seconds, even more preferably less than 50 milliseconds, most preferably less than 10 milliseconds.

Depending on the subject to be treated, the target tissue and the specific application, the volume of the liquid comprising the modified RNA is selected accordingly. In a preferred embodiment of the invention, the volume of the administered liquid is between 0.05 µl and 1000 µl, preferably between 0.1 µl and 500 µl, more preferably between 0.2 µl and 200 µl. Most preferably the volume of the liquid comprising the modified RNA is 100 µl.

In this context, a volume of the liquid comprising the modified RNA is preferably between 0.2 and 200 µl, and is most preferably 100 µl if the modified RNA is injected intradermally by jet injection.

Furthermore, the volume of the liquid comprising the modified RNA is preferably between 100 and 2000 µl and is most preferably 500 µl, if the modified RNA is injected intramuscularly by jet injection.

If the liquid comprising the modified RNA is injected subcutaneously by jet injection, the volume of the liquid comprising the modified RNA is preferably between 100 and 2000 µl and is most preferably 500 µl.

In the meaning of the present invention, any device may be used for jet injection as long as it is capable of generating a liquid jet that is suitable for delivery as defined herein. There is no limitation as to the means, by which the liquid is accelerated. For instance, systems using springs to expell the liquid may be employed as well as systems using gas or other propellants. Furthermore, a constant liquid jet may be used, preferably with at least two distinct velocities in at least two phases as described herein. Alternatively, a pulsed microjet may be used. Preferably, jet injection systems are used that are commercially available, such as Stratis, Tropis (both from Pharmajet), Vitajet, Biojector 2000 or Bioject Zetajet (all three from Bioject Medical Technologies Inc.), Glide (from Glide Pharma), MediJector Vision (from Antares), Sumavel DosePro (from Zogenix), SQ Pen (from Bespak), and Injex (from Equidyne). The modified RNA is injected by using a system, which preferably allows precise and reproducible delivery of a preselected dosage. Preferably, the device ensures suitable tensioning of the skin in order for the liquid jet to be injected into the skin. In a preferred embodiment, a device as disclosed in the international patent application WO 2013/090315, the disclosure of which is included herein in its entirety. Preferably, the modified RNA is injected by using a device that comprises at least one of the individual components of the needle-free injection device as shown in any of FIGS. 1 to 17C of WO 2013/090315, preferably a component selected from the group consisting of a compressible main spring, an actuation button, a skin tensioning spring, a plunger body, a seal and a hammer. More preferably, the modified RNA is injected using a device as disclosed in any of FIGS. 1 to 10 of WO 2013/090315, wherein the main spring can preferably be caused to move laterally away from a syringe end of the injection device when pressure is applied to the needle-free syringe nozzle prior to an injection. In a particularly preferred embodiment, the modified RNA is injected by using a Tropis device (Pharmajet).

According to the invention, an RNA comprising at least one modification and comprising at least one open reading frame is administered by jet injection intradermally, intramuscularly or subcutaneously. In a further preferred embodiment, the modified RNA is administered intradermally, wherein jet injection is performed by using a nozzle that has a diameter of between 20 µm and 150 µm, preferably of between 30 µm and 130 µm, more preferably of between 40 µm and 110 am, even more preferably of between 50 µm and 100 µm and the jet exit velocity is preferably at least 80 m/s, more preferably at least 100 m/s, even more preferably at least 150 m/s and most preferably at least 190 m/s.

In a preferred embodiment, the modified RNA is administered intradermally by using the TROPIS device (Pharmajet).

Typically, the successful delivery of a liquid to the dermis of a mammalian can be assessed by the formation of a wheal (also referred to as bleb) at the site of injection. Preferably, the wheal diameter is at least 5 mm, more preferably at least 7 mm, even more preferably at least 9 and most preferably at least 10 mm.

In the meaning of the present invention, the term "modified RNA" comprises any type of ribonucleic acid molecule that is modified such that the amount of protein or peptide produced from said modified RNA measured at a specific time point or over a specific time period is increased in comparison with RNA lacking the modification ("unmodified reference RNA").

This increase in expression is termed herein as "modification-associated increase of protein expression" as defined above.

According to the invention, a modified RNA molecule is provided, which is characterized by increased expression of the encoded protein in comparison to a respective RNA lacking the modification ("unmodified reference RNA"). In order to assess the in vivo protein production by a modified RNA, the expression of the encoded protein is determined following injection of the modified RNA into target cells/tissue and compared to the protein expression of the unmodified reference RNA. Quantitative methods for determining protein expression are known in the art (e.g. Western-Blot, ELISA, mass spectometry). Particularly useful in this context is the determination of the expression of reporter proteins like luciferase or secreted alkaline phosphatase (SEAP). Thus, modified RNA or unmodified reference RNA is injected into the target tissue, e.g. via conventional needle injection or via jet injection, preferably intradermally, intramuscularly or subcutanously. Several hours or several days (e.g. 6, 12, 24, 48 or 72 hours) post initiation of expression or post injection of the RNA, tissue from the injection site is collected and lysed. Afterwards the lysates can be used to detect and quantify the expressed protein (and thus determine the efficiency of protein expression) using several methods, e.g. Western-Blot, ELISA, mass spectrometry or by fluorescence or luminescence measurement.

Therefore, if the protein expression from a modified RNA is compared to the protein expression from an unmodified reference RNA at a specific time point (e.g. 6, 12, 24, 48 or 72 hours post initiation of expression or post injection of the RNA), both RNAs are injected separately into test animals, tissue from the injection sites is collected after a specific time point, protein lysates are prepared according to the particular protocol adjusted to the particular detection method (e.g. Western Blot, ELISA, etc. as known in the art) and the protein is detected by the chosen detection method and quantified.

If the total amount of protein for a specific time period is to be measured, tissue can be collected after several time points after injection of the RNA (e.g. 6, 12, 24, 48 and 72 hours post initiation of expression or post injection of the RNA; usually from different test animals), and the protein amount per time point can be determined as explained above. In order to calculate the cumulative protein amount, a mathematical method of determining the total amount of protein can be used, e.g. the area under the curve (AUC) can be determined according to the following formula:

$$AUC = \int_a^b f(x)\,d(x)$$

In order to calculate the area under the curve for the total amount of protein, the integral of the equation of the expression curve from each end point (a and b) is calculated.

According to the invention, an RNA molecule is structurally modified in order to enhance the expression of the encoded protein ("modification-associated increase of protein expression"). Therein, the modification is not limited to any particular structure as long as the expression of the encoded protein is increased as compared to an unmodified reference RNA as defined herein. Several RNA modifications are known in the art, which can be applied to a given RNA in the context of the present invention.

Chemical Modifications:

The term "RNA modification" as used herein may refer to chemical modifications comprising backbone modifications as well as sugar modifications or base modifications.

In this context, the modified RNA molecule as defined herein may contain nucleotide analogues/modifications, e.g. backbone modifications, sugar modifications or base modifications. A backbone modification in connection with the present invention is a modification, in which phosphates of the backbone of the nucleotides contained in a nucleic acid molecule as defined herein are chemically modified. A sugar modification in connection with the present invention is a chemical modification of the sugar of the nucleotides of the nucleic acid molecule as defined herein. Furthermore, a base modification in connection with the present invention is a chemical modification of the base moiety of the nucleotides of the nucleic acid molecule of the nucleic acid molecule. In this context nucleotide analogues or modifications are preferably selected from nucleotide analogues which are applicable for transcription and/or translation.

Sugar Modifications:

The modified nucleosides and nucleotides, which may be incorporated into the modified RNA as described herein, can be modified in the sugar moiety. For example, the 2' hydroxyl group (OH) can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), -0(CH2CH2o)nCH2CH2OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified RNA can include nucleotides containing, for instance, arabinose as the sugar.

Backbone Modifications:

The phosphate backbone may further be modified in the modified nucleosides and nucleotides, which may be incorporated into the modified RNA, as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into the modified RNA, as described herein, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyluridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladeno sine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(l-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(l-Thiophosphate)-Pseudouridine.

In further specific embodiments the modified RNA may comprise nucleoside modifications selected from 6-aza-cytidine, 2-thio-cytidine, α-thio-cytidine, Pseudo-iso-cytidine, 5-aminoallyl-uridine, 5-iodo-uridine, N1-methyl-pseudouridine, 5,6-dihydrouridine, α-thio-uridine, 4-thio-uridine, 6-aza-uridine, 5-hydroxy-uridine, deoxy-thymidine, 5-methyl-uridine, Pyrrolo-cytidine, inosine, α-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, α-thio-adenosine, 8-azido-adenosine, 7-deaza-adenosine.

Lipid Modification:

According to a further embodiment, the modified RNA as defined herein can contain a lipid modification. Such a lipid-modified RNA typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an RNA molecule as defined herein, at least one linker covalently linked with that RNA molecule, and at least one lipid covalently linked with the respective linker, and also at least one (bifunctional) lipid covalently linked (without a linker) with that RNA molecule. In this context, it is particularly preferred that the lipid modification is present at the terminal ends of a linear RNA sequence.

Modification of the 5'-End of the Modified RNA:

According to another preferred embodiment of the invention, the modified RNA molecule as defined herein, can be modified by the addition of a so-called "5' CAP" structure. A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in the modified RNA according to the invention. This means the modified RNA according to the present invention may comprise a m7GpppN as 5'-CAP, but additionally the modified RNA comprises at least one further modification as defined herein.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures are regarded as at least one modification comprised in the modified RNA according to the present invention.

Particularly preferred modified 5'-CAP structures are CAP1 (methylation of the ribose of the adjacent nucleotide of m7G), CAP2 (methylation of the ribose of the $2^{nd}$ nucleotide downstream of the m7G), CAP3 (methylation of the ribose of the $3^{rd}$ nucleotide downstream of the m7G), CAP4 (methylation of the ribose of the $4^{th}$ nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

Sequence Modification of the Open Reading Frame:

Modification of the G/C Content:

In a particularly preferred embodiment of the present invention, the G/C content of the coding region, encoding at least one peptide or protein of the modified RNA as defined herein, is modified, particularly increased, compared to the G/C content of its particular wild type coding region, i.e. the unmodified coding region. The encoded amino acid sequence of the coding region is preferably not modified compared to the coded amino acid sequence of the particular wild type coding region.

The modification of the G/C-content of the coding region of the modified RNA as defined herein is based on the fact that the sequence of any mRNA region to be translated is important for efficient translation of that mRNA. Thus, the composition and the sequence of various nucleotides are important. In particular, mRNA sequences having an increased G (guanosine)/C (cytosine) content are more stable than mRNA sequences having an increased A (adenosine)/U (uracil) content. According to the invention, the codons of the coding region are therefore varied compared to its wild type coding region, while retaining the translated amino acid sequence, such that they include an increased amount of G/C nucleotides. In respect to the fact that several codons code for one and the same amino acid (so-called degeneration of the genetic code), the most favourable codons for the stability can be determined (so-called alternative codon usage).

Depending on the amino acid to be encoded by the coding region of the modified RNA as defined herein, there are various possibilities for modification of the RNA sequence, e.g. the coding region, compared to its wild type coding region. In the case of amino acids, which are encoded by codons, which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U is present.

In contrast, codons which contain A and/or U nucleotides can be modified by substitution of other codons which code for the same amino acids but contain no A and/or U. Examples of these are:
the codons for Pro can be modified from CCU or CCA to CCC or CCG;
the codons for Arg can be modified from CGU or CGA or AGA or AGG to CGC or CGG;
the codons for Ala can be modified from GCU or GCA to GCC or GCG;
the codons for Gly can be modified from GGU or GGA to GGC or GGG.

In other cases, although A or U nucleotides cannot be eliminated from the codons, it is however possible to decrease the A and U content by using codons, which contain a lower content of A and/or U nucleotides. Examples of these are:
the codons for Phe can be modified from UUU to UUC;
the codons for Leu can be modified from UUA, UUG, CUU or CUA to CUC or CUG;
the codons for Ser can be modified from UCU or UCA or AGU to UCC, UCG or AGC;
the codon for Tyr can be modified from UAU to UAC;
the codon for Cys can be modified from UGU to UGC;
the codon for His can be modified from CAU to CAC;
the codon for Gln can be modified from CAA to CAG;
the codons for Ile can be modified from AUU or AUA to AUC;
the codons for Thr can be modified from ACU or ACA to ACC or ACG;
the codon for Asn can be modified from AAU to AAC;
the codon for Lys can be modified from AAA to AAG;
the codons for Val can be modified from GUU or GUA to GUC or GUG;
the codon for Asp can be modified from GAU to GAC;
the codon for Glu can be modified from GAA to GAG;
the stop codon UAA can be modified to UAG or UGA.

In the case of the codons for Met (AUG) and Trp (UGG), on the other hand, there is no possibility of sequence modification.

The substitutions listed above can be used either individually or in any possible combination to increase the G/C content of the coding region of the modified RNA as defined herein, compared to its particular wild type coding region (i.e. the original sequence). Thus, for example, all codons for Thr occurring in the wild type sequence can be modified to ACC (or ACG).

Preferably, the G/C content of the coding region of the modified RNA as defined herein is increased by at least 7%, more preferably by at least 15%, particularly preferably by at least 20%, compared to the G/C content of the wild type coding region. According to a specific embodiment at least 5%, 10%, 20%, 30%, 40%, 50%, 60%, more preferably at least 70%, even more preferably at least 80% and most preferably at least 90%, 95% or even 100% of the substitutable codons in the coding region encoding at least one peptide or protein, which comprises a pathogenic antigen or a fragment, variant or derivative thereof, are substituted, thereby increasing the G/C content of said coding region.

In this context, it is particularly preferable to increase the G/C content of the coding region of the modified RNA as defined herein, to the maximum (i.e. 100% of the substitutable codons), compared to the wild type coding region.

Codon Optimization:

According to the invention, a further preferred modification of the coding region encoding at least one peptide or protein of the modified RNA as defined herein, is based on the finding that the translation efficiency is also determined by a different frequency in the occurrence of tRNAs in cells. Thus, if so-called "rare codons" are present in the coding region of the wild type RNA sequence, to an increased extent, the mRNA is translated to a significantly poorer degree than in the case where codons coding for relatively "frequent" tRNAs are present.

In this context, the coding region of the modified RNA is preferably modified compared to the corresponding wild type coding region such that at least one codon of the wild type sequence, which codes for a tRNA which is relatively rare in the cell, is exchanged for a codon, which codes for a tRNA which is relatively frequent in the cell and carries the same amino acid as the relatively rare tRNA. By this modification, the coding region of the modified RNA as defined herein, is modified such that codons, for which frequently occurring tRNAs are available, are inserted. In other words, according to the invention, by this modification all codons of the wild type coding region, which code for a tRNA which is relatively rare in the cell, can in each case be exchanged for a codon, which codes for a tRNA which is relatively frequent in the cell and which, in each case, carries the same amino acid as the relatively rare tRNA.

Which tRNAs occur relatively frequently in the cell and which, in contrast, occur relatively rarely is known to a person skilled in the art; cf. e.g. Akashi, Curr. Opin. Genet. Dev. 2001, 11(6): 660-666. The codons which use for the particular amino acid the tRNA which occurs the most frequently, e.g. the Gly codon, which uses the tRNA which occurs the most frequently in the (human) cell, are particularly preferred.

According to the invention, it is particularly preferable to link the sequential G/C content, which is increased, in particular maximized, in the coding region of the modified RNA as defined herein, with the "frequent" codons without modifying the amino acid sequence of the peptide or protein encoded by the coding region of the RNA sequence. This preferred embodiment allows provision of a particularly efficiently translated and stabilized (modified) RNA sequence as defined herein.

Modification of the 3'-End of the Modified RNA:

Furthermore, in the modified RNA comprising at least one open reading frame that is to be administered by jet injection, the region 3' of the coding region may be modified, e.g. by insertion or addition of stretches of multiple repeats of adenine or cytosine residues. In a preferred embodiment of the invention, the 3' end of an RNA molecule is modified by addition of a series of adenine nucleotides ("poly(A) tail").

The length of the poly(A) tail has a major impact on translation efficiency of the respective construct. To be translated efficiently, the poly(A) tail of exogenously delivered mRNAs should consist of at least 20 A residues. Moreover, it has been described that mRNA expression positively correlates with poly(A) tail length (reviewed in Tavernier et al., J Control Release. 2011 Mar. 30; 150(3): 238-47. PMID: 20970469). In this context Holtkamp et al. showed that a poly(A) tail measuring 120 nucleotides compared with a shorter one, enhanced mRNA stability and translational efficiency (Holtkamp et al., Blood. 2006 Dec. 15; 108(13):4009-17. PMID: 16940422). In one embodiment of the invention, modified RNA is used for jet injection, which comprises (optionally in combination with other modifications) a poly(A) tail, wherein the poly(A) tail comprises at least 30, preferably more than 50, more preferably more than 100, even more preferably more than 200 adenine nucleotides. Most preferably the RNA comprises a poly(A) tail consisting of 64 adenine nucleotides.

In specific embodiments a poly(A) tail is only considered as at least one modification comprised in the modified RNA according to the present invention if the poly(A) tail is longer than 30 adenosines, preferably longer than 50 adenosines, more preferably longer than 100 adenosines and even more preferably longer than 200 adenosines.

In further specific embodiments, the modification with a poly(A) tail is not considered as at least one modification of the modified RNA according to the present invention. This means that the modified RNA according to the invention may comprise a poly(A) tail as defined above but it additionally comprises at least one further modification as defined herein.

In a preferred embodiment, the modified RNA comprising at least one open reading frame which is used for jet injection, comprises (optionally in combination with other modifications) a poly(C) sequence in the region 3' of the coding region of the RNA. A poly(C) sequence is typically a stretch of multiple cytosine nucleotides, typically about 10 to about 200 cytidine nucleotides, preferably about 10 to about 100 cytidine nucleotides, more preferably about 10 to about 70 cytidine nucleotides or even more preferably about 20 to about 50 or even about 20 to about 30 cytidine nucleotides. A poly(C) sequence may preferably be located 3' of the coding region comprised by a nucleic acid. In a specific preferred embodiment of the present invention, the poly(C) sequence is located 3' of a poly(A) sequence.

In a further preferred embodiment, the modified RNA according to the invention comprises or codes for a histone stem-loop at its 3' terminus as at least one modification. In the context of the present invention, a histone stem-loop sequence is preferably selected from at least one of the following formulae (I) or (II):

formula (I) (stem-loop sequence without stem bordering elements):

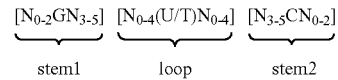

formula (II) (stem-loop sequence with stem bordering elements):

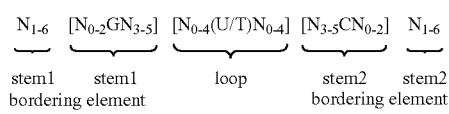

wherein:

| | |
|---|---|
| stem1 or stem2 bordering elements $N_{1-6}$ | is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof; |
| stem1 $[N_{0-2}GN_{3-5}]$ | is reverse complementary or partially reverse complementary with element stem2, and is a consecutive sequence between of 5 to 7 nucleotides; wherein $N_{0-2}$ is a consecutive sequence of 0 to 2, preferably of 0 to 1, more preferably of 1 N, wherein each N is independently from another selected from a nucleotide selected from A, U, T, G and C or anucleotide analogue thereof; wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and wherein G is guanosine or an analogue thereof, and may be optionally replaced by a cytidine or an analogue thereof, provided that its complementary nucleotide cytidine in stem2 is replaced by guanosine; |
| loop sequence $[N_{0-4}(U/T)N_{0-4}]$ | is located between elements stem1 and stem2, and is a consecutive sequence of 3 to 5 nucleotides, more preferably of 4 nucleotides; wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and wherein U/T represents uridine, or optionally thymidine; |
| stem2 $[N_{3-5}CN_{0-2}]$ | is reverse complementary or partially reverse complementary with element stem1, and is a consecutive sequence between of 5 to 7 nucleotides; wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof; wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and wherein C is cytidine or an analogue thereof, and may be optionally replaced by a guanosine or an analogue thereof provided that its complementary nucleoside guanosine in stem1 is replaced by cytidine; | wherein
stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one or more bases in one stem do not have a complementary base in the reverse complementary sequence of the other stem.

According to a further preferred embodiment, the modified RNA according to the present invention may comprise or code for at least one histone stem-loop sequence according to at least one of the following specific formulae (Ia) or (IIa):

formula (Ia) (stem-loop sequence without stem bordering elements):

$$\underbrace{[N_{0-1}GN_{3-5}]}_{\text{stem1}} \underbrace{[N_{1-3}(U/T)N_{0-2}]}_{\text{loop}} \underbrace{[N_{3-5}CN_{0-1}]}_{\text{stem2}}$$

formula (IIa) (stem-loop sequence with stem bordering elements):

$$\underbrace{N_{2-5}}_{\substack{\text{stem1}\\\text{bordering element}}} \underbrace{[N_{0-1}GN_{3-5}]}_{\text{stem1}} \underbrace{[N_{1-3}(U/T)N_{0-2}]}_{\text{loop}} \underbrace{[N_{3-5}CN_{0-1}]}_{\text{stem2}} \underbrace{N_{2-5}}_{\substack{\text{stem2}\\\text{bordering element}}}$$

wherein:
N, C, G, T and U are as defined above.

According to a further more particularly preferred embodiment, the modified RNA may comprise or code for at least one histone stem-loop sequence according to at least one of the following specific formulae (Ib) or (IIb):

formula (Ib) (stem-loop sequence without stem bordering elements):

$$\underbrace{[N_1GN_4]}_{\text{stem1}} \underbrace{[N_2(U/T)N_1]}_{\text{loop}} \underbrace{[N_4CN_1]}_{\text{stem2}}$$

formula (IIb) (stem-loop sequence with stem bordering elements):

$$\underbrace{N_{4-5}}_{\substack{\text{stem1}\\\text{bordering element}}} \underbrace{[N_1GN_4]}_{\text{stem1}} \underbrace{[N_2(U/T)N_1]}_{\text{loop}} \underbrace{[N_4CN_1]}_{\text{stem2}} \underbrace{N_{4-5}}_{\substack{\text{stem2}\\\text{bordering element}}}$$

wherein: N, C, G, T and U are as defined above.

According to an even more preferred embodiment, the modified RNA according to the present invention may comprise or code for at least one histone stem-loop sequence according to at least one of the following specific formulae (Ic) to (Ih) or (IIc) to (IIh), shown alternatively in its stem-loop structure and as a linear sequence representing histone stem-loop sequences as generated according to Example 1 formula (Ic): (metazoan and protozoan histone stem-loop consensus sequence without stem bordering elements):

```
                              (SEQ ID NO: 1)
      N U
     N   N
     N-N
     N-N
     N-N
     N-N
     G-C
     N-N  (stem-loop structure)
 NGNNNNNNNUNNNNNCN
   (linear sequence)
``` formula (IIc): (metazoan and protozoan histone stem-loop consensus sequence with stem bordering elements):

```
                              (SEQ ID NO: 2)
      N U
     N   N
     N-N
     N-N
     N-N
     N-N
     G-C
 N*N*NNNN-NNNN*N*N*  (stem-loop structure)
 N*N*NNNNGNNNNNNUNNNNNCNNNN*N*N*
   (linear sequence)
``` formula (Id): (without stem bordering elements)

```
                              (SEQ ID NO: 3)
      N U
     N   N
     N-N
     N-N
     N-N
     N-N
     C-G
     N-N  (stem-loop structure)
  NCNNNNNNNUNNNNNGN
   (linear sequence)
``` formula (KKd): (with stem bordering elements)

```
                              (SEQ ID NO: 4)
      N U
     N   N
     N-N
     N-N
     N-N
     N-N
     C-G
 N*N*NNNN-NNNN*N*N*  (stem-loop structure)
 N*N*NNNNCNNNNNNUNNNNNGNNNN*N*N*
   (linear sequence)
``` formula (Ie): (protozoan histone stem-loop consensus sequence without stem bordering elements)

```
                              (SEQ ID NO: 5)
      N U
     N   N
     N-N
     N-N
     N-N
     N-N
```

-continued
```
            G-C
            D-H  (stem-loop structure)
    DGNNNNNNUNNNNNCH
    (linear sequence)
``` formula (IIe): (protozoan histone stem-loop consensus sequence with stem bordering elements)

```
                                            (SEQ ID NO: 6)
            N U
           N   N
            N-N
            N-N
            N-N
            N-N
            G-C
    N*N*NNND-HNNN*N*N*  (stem-loop structure)
    N*N*NNNDGNNNNNNUNNNNNCHNNN*N*N*
    (linear sequence)
``` formula (If): (metazoan histone stem-loop consensus sequence without stem bordering elements)

```
                                            (SEQ ID NO: 7)
            N U
           N   N
            Y-V
            Y-N
            B-D
            N-N
            G-C
            N-N  (stem-loop structure)
    NGNBYYNNUNVNDNCN
    (linear sequence)
``` formula (IIf): (metazoan histone stem-loop consensus sequence with stem bordering elements)

```
                                            (SEQ ID NO: 8)
            N U
           N   N
            Y-V
            Y-N
            B-D
            N-N
            G-C
    N*N*NNNN-NNNN*N*N*  (stem-loop structure)
    N*N*NNNNGNBYYNNUNVNDNCNNNN*N*N*
    (linear sequence)
``` formula (Ig): (vertebrate histone stem-loop consensus sequence without stem bordering elements)

```
                                            (SEQ ID NO: 9)
            N U
            D H
            Y-A
            Y-B
            Y-R
            H-D
            G-C
            N-N  (stem-loop structure)
    NGHYYYDNUHABRDCN
    (linear sequence)
``` formula (IIg): (vertebrate histone stem-loop consensus sequence with stem bordering elements)

```
                                            (SEQ ID NO: 10)
            N U
            D H
            Y-A
```

```
            Y-B
            Y-R
            H-D
            G-C
    N*N*HNNN-NNNN*N*H*  (stem-loop structure)
    N*N*HNNNGHYYYDNUHABRDCNNNN*N*H*
    (linear sequence)
``` formula (Ih): (human histone stem-loop consensus sequence (*Homo sapiens*) without stem bordering elements)

```
                                            (SEQ ID NO: 11)
            Y U
            D H
            U-A
            C-S
            Y-R
            H-R
            G-C
            D-C  (stem-loop structure)
    DGHYCUDYUHASRRCC
    (linear sequence)
``` formula (IIh): (human histone stem-loop consensus sequence (*Homo sapiens*) with stem bordering elements)

```
                                            (SEQ ID NO: 12)
            Y U
            D H
            U-A
            C-S
            Y-R
            H-R
            G-C
    N*H*AAHD-CVHB*N*H*  (stem loop structure)
    N*H*AAHDGHYCUDYUHASRRCCVHB*N*H*
    (linear sequence)
``` wherein in each of above formulae (Ic) to (Ih) or (IIc) to (IIh): N, C, G, A, T and U are as defined above; each U may be replaced by T; each (highly) conserved G or C in the stem elements 1 and 2 may be replaced by its complementary nucleotide base C or G, provided that its complementary nucleotide in the corresponding stem is replaced by its complementary nucleotide in parallel; and/or G, A, T, U, C, R, Y, M, K, S, W, H, B, V, D, and N are nucleotide bases as defined in the following Table:

| abbreviation | Nucleotide bases | remark |
|---|---|---|
| G | G | Guanine |
| A | A | Adenine |
| T | T | Thymine |
| U | U | Uracile |
| C | C | Cytosine |
| R | G or A | Purine |
| Y | T/U or C | Pyrimidine |
| M | A or C | Amino |
| K | G or T/U | Keto |
| S | G or C | Strong (3H bonds) |
| W | A or T/U | Weak (2H bonds) |
| H | A or C or T/U | Not G |
| B | G or T/U or C | Not A |
| V | G or C or A | Not T/U |
| D | G or A or T/U | Not C |
| N | G or C or T/U or A | Any base |
| * | Present or not | Base may be present or not |

In this context, it is particularly preferred that the histone stem-loop sequence according to at least one of the formulae (I) or (Ia) to (Ih) or (II) or (IIa) to (IIh) of the present invention is selected from a naturally occurring histone stem loop sequence, more particularly preferred from protozoan or metazoan histone stem-loop sequences, and even more particularly preferred from vertebrate and mostly preferred from mammalian histone stem-loop sequences especially from human histone stem-loop sequences.

According to a particularly preferred embodiment, the histone stem-loop sequence according to at least one of the specific formulae (I) or (Ia) to (Ih) or (II) or (IIa) to (IIh) of the present invention is a histone stem-loop sequence comprising at each nucleotide position the most frequently occurring nucleotide, or either the most frequently or the second-most frequently occurring nucleotide of naturally occurring histone stem-loop sequences in metazoa and protozoa, protozoa, metazoa, vertebrates and humans. In this context it is particularly preferred that at least 80%, preferably at least 85%, or most preferably at least 90% of all nucleotides correspond to the most frequently occurring nucleotide of naturally occurring histone stem-loop sequences.

In a further particular embodiment, the histone stem-loop sequence according to at least one of the specific formulae (I) or (Ia) to (Ih) of the present invention is selected from following histone stem-loop sequences (without stem-bordering elements):

```
(SEQ ID NO: 13 according to formula (Ic))
    VGYYYYHHTHRVVRCB
(SEQ ID NO: 14 according to formula (Ic))
    SGYYYTTYTMARRRCS
(SEQ ID NO: 15 according to formula (Ic))
    SGYYCTTTTMAGRRCS
(SEQ ID NO: 16 according to formula (Ie))
    DGNNNBNNTHVNNNCH
(SEQ ID NO: 17 according to formula (Ie))
    RGNNNYHBTHRDNNCY
(SEQ ID NO: 18 according to formula (Ie))
    RGNDBYHYTHRDHNCY
(SEQ ID NO: 19 according to formula (If))
    VGYYYTYHTHRVRRCB
(SEQ ID NO: 20 according to formula (If))
    SGYYCTTYTMAGRRCS
(SEQ ID NO: 21 according to formula (If))
    SGYYCTTTTMAGRRCS
(SEQ ID NO: 22 according to formula (Ig))
    GGYYCTTYTHAGRRCC
(SEQ ID NO: 23 according to formula (Ig))
    GGCYCTTYTMAGRGCC
(SEQ ID NO: 24 according to formula (Ig))
    GGCTCTTTTMAGRGCC
(SEQ ID NO: 25 according to formula (Ih))
    DGHYCTDYTHASRRCC
(SEQ ID NO: 26 according to formula (Ih))
    GGCYCTTTTHAGRGCC
(SEQ ID NO: 27 according to formula (Ih))
    GGCYCTTTTMAGRGCC
```

Furthermore in this context, following histone stem-loop sequences (with stem bordering elements) according to one of specific formulae (II) or (IIa) to (IIh) are particularly preferred:

```
(SEQ ID NO: 28 according to formula (IIc))
    H*H*HHVVGYYYYHHTHRVVRCBVHH*N*N*
(SEQ ID NO: 29 according to formula (IIc))
    M*H*MHMSGYYYTTYTMARRRCSMCH*H*H*
(SEQ ID NO: 30 according to formula (IIc))
    M*M*MMMSGYYCTTTTMAGRRCSACH*M*H*
(SEQ ID NO: 31 according to formula (IIe))
    N*N*NNNDGNNNBNNTHVNNNCHNHN*N*N*
(SEQ ID NO: 32 according to formula (IIe))
    N*N*HHNRGNNNYHBTHRDNNCYDHH*N*N*
(SEQ ID NO: 33 according to formula (IIe))
    N*H*HHVRGNDBYHYTHRDHNCYRHH*H*H*
(SEQ ID NO: 34 according to formula (IIf))
    H*H*MHMVGYYYTYHTHRVRRCBVMH*H*N*
(SEQ ID NO: 35 according to formula (IIf))
    M*M*MMMSGYYCTTYTMAGRRCSMCH*H*H*
(SEQ ID NO: 36 according to formula (IIf))
    M*M*MMMSGYYCTTTTMAGRRCSACH*M*H*
(SEQ ID NO: 37 according to formula (IIg))
    H*H*MAMGGYYCTTYTHAGRRCCVHN*N*M*
(SEQ ID NO: 38 according to formula (IIg))
    H*H*AAMGGCYCTTYTMAGRGCCVCH*H*M*
(SEQ ID NO: 39 according to formula (IIg))
    M*M*AAMGGCTCTTTTMAGRGCCMCY*M*M*
(SEQ ID NO: 40 according to formula (IIh))
    N*H*AAHDGHYCTDYTHASRRCCVHB*N*H*
(SEQ ID NO: 41 according to formula (IIh))
    H*H*AAMGGCYCTTTTHAGRGCCVMY*N*M*
(SEQ ID NO: 42 according to formula (IIh))
    H*M*AAAGGCYCTTTTMAGRGCCRMY*H*M*
```

According to a further preferred embodiment, the modified RNA comprises or codes for at least one histone stem-loop sequence showing at least about 80%, preferably at least about 85%, more preferably at least about 90%, or even more preferably at least about 95%, sequence identity with the not to 100% conserved nucleotides in the histone stem-loop sequences according to at least one of specific formulae (I) or (Ia) to (Ih) or (II) or (IIa) to (IIh) or with a naturally occurring histone stem-loop sequence.

A particular preferred example for a histone stem-loop sequence is the sequence according to SEQ ID NO: 43 (CAAAGGCTCTTTTCAGAGCCACCA) or the corresponding RNA sequence according to SEQ ID NO.: 44 (CAAAGGCUCUUUUCAGAGCCACCA).

Utr Modification:

Preferably, the modified RNA according to the invention has at least one modified 5' and/or 3' UTR sequence (UTR modification). These modifications in the 5' and/or 3' untranslated regions (UTR) may have the effect of increasing the half-life of the RNA in the cytosol or may increase the translational efficiency and may thus enhance the expression of the encoded protein or peptide. These UTR sequences can have 100% sequence identity to naturally occurring sequences which occur in viruses, bacteria and eukaryotes, but can also be partly or completely synthetic. The untranslated sequences (UTR) of the (alpha-) or beta globin gene, e.g. from *Homo sapiens* or *Xenopus laevis* may be mentioned as an example of stabilizing sequences which can be used for a stabilized RNA. Another example of a stabilizing sequence has the general formula (C/U)CCANxCCC(U/A)PyxUC(C/U)CC which is contained in the 3'UTR of the very stable RNA which codes for (alpha-)globin, type(I)-collagen, 15-lipoxygenase or for tyrosine hydroxylase (cf. Holcik et al., Proc. Natl. Acad. Sci. USA 1997, 94: 2410 to 2414). Particularly preferred in the context of the present invention is the mutated UTR of (alpha-) globin comprising the following sequence GCCCGaTGGG CCTCCCAACG GGCCCTCCTC CCCTCCTTGC ACCG (SEQ ID NO. 45) (the underlined nucleotide shows the mutation compared to the wild type sequence), which is also termed herein as "muag". Such introduced UTR sequences can, of course, be used individually or in combination with one another and also in combination with other sequence modifications known to a person skilled in the art.

Preferably, decay signals are removed from the 3' untranslated regions (3' UTRs) of an RNA according to the invention. Specifically, Adenylate Uridylate Rich Elements (AREs) are replaced by the 3'UTR of a stable mRNA (e.g. α- or β-globin mRNA) (reviewed in Tavernier et al., J Control Release. 2011 Mar. 30; 150(3):238-47. PMID: 20970469).

In this context, it was shown that the 3'UTR of α-globin mRNA may be an important factor for the well-known stability of α-globin mRNA (Rodgers et al., Regulated α-globin mRNA decay is a cytoplasmic event proceeding through 3'-to-5' exosome-dependent decapping, RNA, 8, pp. 1526-1537, 2002). The 3'UTR of α-globin mRNA is apparently involved in the formation of a specific ribonucleoprotein-complex, the α-complex, whose presence correlates with mRNA stability in vitro (Wang et al., An mRNA stability complex functions with poly(A)-binding protein to stabilize mRNA in vitro, Molecular and Cellular biology, Vol 19, No. 7, July 1999, p. 4552-4560).

In this context, it is particularly preferred that the naturally occuring 5'- and/or 3'-UTRs of the gene comprising the open reading frame contained in the modified RNA according to the invention is removed in the modified RNA. Thus, the modified RNA according to the invention preferably comprises UTRs which are heterologous to the open reading frame if present in the modified RNA.

In a preferred embodiment, a combination of two or more of the modifications described above are present in one modified RNA that is administered by jet injection and which comprises at least one open reading frame. In a particularly preferred embodiment, an RNA comprising at least one open reading frame is modified by introducing a (heterologous) 3' UTR, a poly(A) tail, a poly(C) sequence and a histone stem-loop. Preferably, the 3' UTR therein is the mutated UTR of (alpha-) globin comprising the sequence GCCCGaTGGG CCTCCCAACG GGCCCTCCTC CCCTCCTTGC ACCG (SEQ ID NO. 45; muag; the underlined nucleotide shows the mutation compared to the wild type sequence), the poly(A) tail consists of 64 adenine nucleotides, the poly(C) sequence consists of 30 cytosine nucleotides and the histone stem-loop has a structure selected from one of formulae (I) or (II), preferably the RNA sequence according to SEQ ID NO. 44 (CAAAGGCUCUUUUCAGAGCCACCA). Most preferably, the RNA of that specific embodiment comprises the sequence modifications as shown in FIG. 4 (SEQ ID NO. 46; see also Example 1).

By a further embodiment, the modified RNA according to the invention preferably comprises at least one of the following structural elements: a 5'- and/or 3'-untranslated region element (UTR element), particularly a 5'-UTR element, which comprises or consists of a nucleic acid sequence, which is derived from the 5'-UTR of a TOP gene or from a fragment, homolog or a variant thereof, or a 5'- and/or 3'-UTR element, which may be derivable from a gene that provides a stable mRNA or from a homolog, fragment or variant thereof; a histone-stem-loop structure, preferably a histone-stem-loop in its 3' untranslated region; a 5'-CAP structure; a poly-A tail; or a poly(C) sequence.

In a preferred embodiment of the first aspect of the present invention, the modified RNA according to the invention comprises at least one 5'- or 3'-UTR element. In this context an UTR element comprises or consists of a nucleic acid sequence, which is derived from the 5'- or 3'-UTR of any naturally occurring gene, or which is derived from a fragment, a homolog or a variant of the 5'- or 3'-UTR of a gene. Preferably, the 5'- or 3'-UTR element used according to the present invention is heterologous to the coding region of the modified RNA according to the invention. Even if 5'- or 3'-UTR elements derived from naturally occurring genes are preferred, also synthetically engineered UTR elements may be used in the context of the present invention.

In a particularly preferred embodiment of the first aspect of the present invention, the sequence of the modified RNA according to the invention comprises at least one 5'-untranslated region element (5'UTR element), which comprises or consists of a nucleic acid sequence, which is derived from the 5'UTR of a TOP gene, or which is derived from a fragment, homolog or variant of the 5'UTR of a TOP gene.

It is particularly preferred that the 5'UTR element does not comprise a TOP-motif or a 5'TOP, as defined above.

In some embodiments, the nucleic acid sequence of the 5'UTR element, which is derived from a 5'UTR of a TOP gene terminates at its 3'-end with a nucleotide located at position 1, 2, 3, 4, 5, 6, 7, 8, 9 or 10 upstream of the start codon (e.g. A(U/T)G) of the gene or mRNA it is derived from. Thus, the 5'UTR element does not comprise any part of the protein coding region. Thus, preferably, the only protein coding part of the modified RNA according to the invention is provided by the coding region.

The nucleic acid sequence, which is derived from the 5'UTR of a TOP gene, is derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element is prefereably selected from 5'-UTR elements comprising or consisting of a nucleic acid sequence, which is derived from a nucleic acid sequence selected from the group consisting of SEQ ID Nos. 1-1363, SEQ ID NO. 1395, SEQ ID NO. 1421 and SEQ ID NO. 1422 of the patent application WO2013/143700, whose disclosure is incorporated herein by reference, from the homologs of SEQ ID Nos. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID Nos. 1-1363, SEQ ID NO. 1395, SEQ ID NO. 1421 and SEQ ID NO. 1422 of the patent application WO2013/143700" refers to sequences of other species than *Homo sapiens*, which are homologous to the sequences according to SEQ ID Nos. 1-1363, SEQ ID NO. 1395, SEQ ID NO. 1421 and SEQ ID NO. 1422 of the patent application WO2013/143700.

In a preferred embodiment, the 5'UTR element comprises or consists of a nucleic acid sequence, which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID Nos. 1-1363, SEQ ID NO. 1395, SEQ ID NO. 1421 and SEQ ID NO. 1422 of the patent application WO2013/143700, from the homologs of SEQ ID Nos. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'UTR element comprises or consists of a nucleic acid sequence, which is derived from a 5'UTR of a TOP gene encoding a ribosomal protein or from a variant of a 5'UTR of a TOP gene encoding a ribosomal protein. For example, the 5'UTR element comprises or consists of a nucleic acid sequence which is derived from a 5'UTR of a nucleic acid sequence according to any of SEQ ID NOs: 67, 170, 193, 244, 259, 554, 650, 675, 700, 721, 913, 1016, 1063, 1120, 1138, and 1284-1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3'end of the sequences) corresponds to the 5'UTR of said sequences.

Preferably, the 5'UTR element comprises or consists of a nucleic acid sequence, which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence, which is derived from a 5'UTR of a nucleic acid sequence according to any of SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'UTR element comprises or consists of a nucleic acid sequence, which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'UTR element does not comprise the 5'TOP of said gene.

Accordingly, in a particularly preferred embodiment, the 5'UTR element comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 55 (5'-UTR of human ribosomal protein Large 32 lacking the 5' terminal oligopyrimidine tract: GGCGCTGCCTACGGAGGTGGCAGCCATCTCCT-TCTCGGCATC; corresponding to SEQ ID No. 1368 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 55 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the modified RNA according to the invention comprises a 5'UTR element, which comprises or consists of a nucleic acid sequence, which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB, or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5'terminal oligopyrimidine tract (TOP), and wherein further optionally the 5'UTR element, which is derived from a 5'UTR of a TOP gene, terminates at its 3'-end with a nucleotide located at position 1, 2, 3, 4, 5, 6, 7, 8, 9 or 10 upstream of the start codon (A(U/T)G) of the gene it is derived from.

In further particularly preferred embodiments, the 5'UTR element comprises or consists of a nucleic acid sequence, which is derived from the 5'UTR of a ribosomal protein Large 32 gene (RPL32), a ribosomal protein Large 35 gene (RPL35), a ribosomal protein Large 21 gene (RPL21), an ATP synthase, H+ transporting, mitochondrial F1 complex, alpha subunit 1, cardiac muscle (ATP5A1) gene, an hydroxysteroid (17-beta) dehydrogenase 4 gene (HSD17B4), an androgen-induced 1 gene (AIG1), cytochrome c oxidase subunit VIc gene (COX6C), or a N-acylsphingosine amidohydrolase (acid ceramidase) 1 gene (ASAH1) or from a variant thereof, preferably from a vertebrate ribosomal protein Large 32 gene (RPL32), a vertebrate ribosomal protein Large 35 gene (RPL35), a vertebrate ribosomal protein Large 21 gene (RPL21), a vertebrate ATP synthase, H+ transporting, mitochondrial F1 complex, alpha subunit 1, cardiac muscle (ATP5A1) gene, a vertebrate hydroxysteroid (17-beta) dehydrogenase 4 gene (HSD17B4), a vertebrate androgen-induced 1 gene (AIG1), a vertebrate cytochrome c oxidase subunit VIc gene (COX6C), or a vertebrate N-acylsphingosine amidohydrolase (acid ceramidase) 1 gene (ASAH1) or from a variant thereof, more preferably from a mammalian ribosomal protein Large 32 gene (RPL32), a ribosomal protein Large 35 gene (RPL35), a ribosomal protein Large 21 gene (RPL21), a mammalian ATP synthase, H+ transporting, mitochondrial F1 complex, alpha subunit 1, cardiac muscle (ATP5A1) gene, a mammalian hydroxysteroid (17-beta) dehydrogenase 4 gene (HSD17B4), a mammalian androgen-induced 1 gene (AIG1), a mammalian cyto-chrome c oxidase subunit VIc gene (COX6C), or a mammalian N-acylsphingosine ami-dohydrolase (acid ceramidase) 1 gene (ASAH1) or from a variant thereof, most preferably from a human ribosomal protein Large 32 gene (RPL32), a human ribosomal protein Large 35 gene (RPL35), a human ribosomal protein Large 21 gene (RPL21), a human ATP syn-thase, H+ transporting, mitochondrial F1 complex, alpha subunit 1, cardiac muscle (ATP5A1) gene, a human hydroxysteroid (17-beta) dehydrogenase 4 gene (HSD17B4), a human androgen-induced 1 gene (AIG1), a human cytochrome c oxidase subunit VIc gene (COX6C), or a human N-acylsphingosine amidohydrolase (acid ceramidase) 1 gene (ASAH1) or from a variant thereof, wherein preferably the 5'UTR element does not comprise the 5'TOP of said gene.

In a particularly preferred embodiment, the 5'UTR element comprises or consists of a nucleic acid sequence, which is derived from the 5'UTR of an hydroxysteroid (17-beta) dehydrogenase 4 gene (HSD17B4), preferably from a vertebrate hydroxysteroid (17-beta) dehydrogenase 4 gene (HSD17B4), more preferably from a mammalian hydroxysteroid (17-beta) dehydrogenase 4 gene (HSD17B4), most preferably from a human hydroxysteroid (17-beta) dehydrogenase 4 gene (HSD17B4). In a preferred embodiment, the 5'UTR element comprises or consists of a nucleic acid sequence that has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the 5'UTR comprised in the nucleic acid sequence according to SEQ ID NO: 54. Preferably, the 5'UTR comprises or consists of the 5'UTR as comprised in the nucleic acid sequence according to SEQ ID NO: 54.

Accordingly, in a particularly preferred embodiment, the 5'UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, or a corresponding RNA sequence, or wherein the at least one 5'UTR element comprises or consists of a fragment of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 1368, or SEQ ID NOs 1412-1420 of the patent application WO2013/143700, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

Accordingly, in a particularly preferred embodiment, the 5'UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 56 (5'-UTR of ATP5A1 lacking the 5' terminal oligopyrimidine tract: GCGGCTCGGCCATTTT-GTCCCAGTCAGTCCGGAGGCTGCGGCTGCAGAAG-TACCGCC TGCG-GAGTAACTGCAAAG; corresponding to SEQ ID No. 1414 of the patent application WO2013/143700) or preferably to a corresponding RNA sequence, or wherein the at least one 5'UTR element comprises or consists of a fragment of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 26 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In a further preferred embodiment, the modified RNA according to the invention further comprises at least one 3'UTR element, which comprises or consists of a nucleic acid sequence derived from the 3'UTR of a chordate gene, preferably a vertebrate gene, more preferably a mammalian gene, most preferably a human gene, or from a variant of the 3'UTR of a chordate gene, preferably a vertebrate gene, more preferably a mammalian gene, most preferably a human gene.

The term '3'UTR element' refers to a nucleic acid sequence, which comprises or consists of a nucleic acid sequence that is derived from a 3'UTR or from a variant of a 3'UTR. A 3'UTR element in the sense of the present invention may represent the 3'UTR of an mRNA. Thus, in the sense of the present invention, preferably, a 3'UTR element may be the 3'UTR of an mRNA, preferably of an artificial mRNA, or it may be the transcription template for a 3'UTR of an mRNA. Thus, a 3'UTR element preferably is a nucleic acid sequence, which corresponds to the 3'UTR of an mRNA, preferably to the 3'UTR of an artificial mRNA, such as an mRNA obtained by transcription of a genetically engineered vector construct. Preferably, the 3'UTR element fulfils the function of a 3'UTR or encodes a sequence, which fulfils the function of a 3'UTR.

Preferably, the inventive mRNA comprises a 3'UTR element, which may be derivable from a gene that relates to an mRNA with an enhanced half-life (that provides a stable mRNA), for example a 3'UTR element as defined and described below.

In a particularly preferred embodiment, the 3'UTR element comprises or consists of a nucleic acid sequence, which is derived from a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene, or from a variant of a 3'UTR of a gene selected from the group consisting of an albumin gene, an α-globin gene, a β-globin gene, a tyrosine hydroxylase gene, a lipoxygenase gene, and a collagen alpha gene, such as a collagen alpha 1(I) gene according to SEQ ID No. 1369-1390 of the patent application WO2013/143700, whose disclosure is incorporated herein by reference. In a particularly preferred embodiment, the 3'UTR element comprises or consists of a nucleic acid sequence, which is derived from a 3'UTR of an albumin gene, preferably a vertebrate albumin gene, more preferably a mammalian albumin gene, most preferably a human albumin gene according to SEQ ID No. 57.

Human albumin 3'UTR SEQ ID No. 57:

CATCACATTT AAAAGCATCT CAGCCTACCA TGAGAATAAG

AGAAAGAAAA TGAAGATCAA AAGCTTATTC ATCTGTTTTT

CTTTTTCGTT GGTGTAAAGC CAACACCCTG TCTAAAAAAC

ATAAATTTCT TTAATCATTT TGCCTCTTTT CTCTGTGCTT

CAATTAATAA AAAATGGAAA GAATCT (corresponding to SEQ

ID No: 1369 of the patent application

WO2013/143700).

In this context, it is particularly preferred that the modified RNA according to the invention comprises a 3'-UTR element comprising a corresponding RNA sequence derived from the nucleic acids according to SEQ ID No. 1369-1390 of the patent application WO2013/143700 or a fragment, homolog or variant thereof.

Most preferably the 3'-UTR element comprises the nucleic acid sequence derived from a fragment of the human albumin gene according to SEQ ID No. 58:

albumin7 3'UTR
CATCACATTTAAAAGCATCTCAGCCTACCATGAGAATAAGAGAAAGAAA

ATGAAGATCAATAGCTTATTCATCTCTTTTTCTTTTTCGTTGGTGTAAA

GCCAACACCCTGTCTAAAAAACATAAATTTCTTTAATCATTTTGCCTC

TTTTCTCTGTGCTTCAATTAATAAAAAATGGAAAGAACCT. (SEQ ID

No. 58 corresponding to SEQ ID No: 1376 of the patent application WO2013/143700)

In this context, it is particularly preferred that the 3'-UTR element of the inventive mRNA comprises or consists of a corresponding RNA sequence of the nucleic acid sequence according to SEQ ID No. 58.

In another particularly preferred embodiment, the 3'UTR element comprises or consists of a nucleic acid sequence, which is derived from a 3'UTR of an α-globin gene, preferably a vertebrate α- or β-globin gene, more preferably a mammalian α- or β-globin gene, most preferably a human α- or β-globin gene according to SEQ ID No. 59-61:

3'-UTR of Homo sapiens hemoglobin, alpha 1 (HBA1)
GCTGGAGCCTCGGTGGCCATGCTTCTTGCCCCTTGGGCCTCCCCCCA

GCCCCTCCTCCCCTTCCTGCACCCGTACCCCCGTGGTCTTTGAATAAA

GTCTGAGTGGGCGGC (SEQ ID No: 59 corresponding to

SEQ ID No. 1370 of the patent application

WO2013/143700)

3'-UTR of Homo sapiens hemoglobin, alpha 2 (HBA2)
GCTGGAGCCTCGGTAGCCGTTCCTCCTGCCCGCTGGGCCTCCCAACG

GGCCCTCCTCCCCTCCTTGCACCGGCCCTTCCTGGTCTTTGAATAAAG

TCTGAGTGGGCAG (SEQ ID No: 60 corresponding to SEQ

ID No. 1371 of the patent application

WO013/143700)

3'-UTR of Homo sapiens hemoglobin, beta (HBB)
GCTCGCTTTCTTGCTGTCCAATTTCTATTAAAGGTTCCTTTGTTCCCTAA

GTCCAACTACTAAACTGGGGGATATTATGAAGGGCCTTGAGCATCTG

GATTCTGCCTAATAAAAAACATTTATTTTCATTGC (SEQ ID No: 61 corresponding to SEQ ID No. 1372 of the patent application WO2013/143700)

For example, the 3'UTR element may comprise or consist of the center, α-complex-binding portion of the 3'UTR of an α-globin gene, such as of a human α-globin gene, preferably according to SEQ ID No. 62:

Center, α-complex-binding portion of the 3'UTR of an α-globin gene (also named herein as "muag") GCCCGATGGGCCTCCCAACGGGCCCTCCTCCCCTC-CTTGCACCG (SEQ ID NO. 62 corresponding to SEQ ID No. 1393 of the patent application WO2013/143700).

In this context, it is particularly preferred that the 3'-UTR element of the modified RNA according to the invention comprises or consists of a corresponding RNA sequence of the nucleic acid sequence according to SEQ ID No. 62 or a homolog, a fragment or variant thereof.

The term 'a nucleic acid sequence, which is derived from the 3'UTR of a [ . . . ] gene' preferably refers to a nucleic acid sequence, which is based on the 3'UTR sequence of a [ . . . ] gene or on a part thereof, such as on the 3'UTR of an albumin gene, an α-globin gene, a 3-globin gene, a tyrosine hydroxylase gene, a lipoxygenase gene, or a collagen alpha gene, such as a collagen alpha 1(I) gene, preferably of an albumin gene or on a part thereof. This term includes sequences corresponding to the entire 3'UTR sequence, i.e. the full length 3'UTR sequence of a gene, and sequences corresponding to a fragment of the 3'UTR sequence of a gene, such as an albumin gene, α-globin gene, β-globin gene, tyrosine hydroxylase gene, lipoxygenase gene, or collagen alpha gene, such as a collagen alpha 1(I) gene, preferably of an albumin gene.

The term 'a nucleic acid sequence, which is derived from a variant of the 3'UTR of a [ . . . ] gene' preferably refers to a nucleic acid sequence, which is based on a variant of the 3'UTR sequence of a gene, such as on a variant of the 3'UTR of an albumin gene, an α-globin gene, a β-globin gene, a tyrosine hydroxylase gene, a lipoxygenase gene, or a collagen alpha gene, such as a collagen alpha 1(I) gene, or on a part thereof as described above. This term includes sequences corresponding to the entire sequence of the variant of the 3'UTR of a gene, i.e. the full length variant 3'UTR sequence of a gene, and sequences corresponding to a fragment of the variant 3'UTR sequence of a gene. A fragment in this context preferably consists of a continuous stretch of nucleotides corresponding to a continuous stretch of nucleotides in the full-length variant 3'UTR, which represents at least 20%, preferably at least 30%, more preferably at least 40%, more preferably at least 50%, even more preferably at least 60%, even more preferably at least 70%, even more preferably at least 80%, and most preferably at least 90% of the full-length variant 3'UTR. Such a fragment of a variant, in the sense of the present invention, is preferably a functional fragment of a variant as described herein.

Preferably, the at least one 5'UTR element and the at least one 3'UTR element act synergistically to increase protein production from the modified RNA according to the invention as described above. More preferably, the at least one 5'UTR element and/or the at least one 3'UTR element act synergistically together with jet injection of the modified RNA in order to increase protein production.

In further specific embodiments, the modified RNA according to the invention may—in addition to the at least one modification—further comprise an internal ribosome entry site (IRES) sequence or IRES-motif, which may separate several open reading frames, for example if the modified RNA encodes for two or more peptides or proteins. An IRES-sequence may be particularly helpful if the mRNA is a bi- or multicistronic RNA.

As used in the context of the present invention, the term "RNA" is not limiting and refers to any ribonucleic acid. Thus, the term RNA equally applies to ribonucleic acids that function as coding RNAs for example, as viral RNA, replicon or as mRNA or to artificial RNA constructs of any type.

In a preferred embodiment, the modified RNA is not a small interfering RNA (siRNA) or a short hairpin RNA (shRNA). Preferably, the modified RNA is not an siRNA or shRNA against a resistance gene, preferably a multidrug resistance gene, such as MDR1/P-gp.

According to the invention, the RNA comprises at least one modification, which increases the expression of the peptide or protein encoded by the coding region of the RNA. In a preferred embodiment, the RNA according to the invention comprises at least one type of modification as defined herein. In another preferred embodiment, the RNA according to the invention comprises at least two distinct types of modifications that increase the expression of the peptide or protein encoded by the coding region of the RNA. Preferably, the RNA according to the invention comprises at least two, three, four, five, six, seven, eight, nine, ten, eleven or twelve distinct types of modifications. Alternatively, or in combination with other other types of modifications, a specific modification as defined herein, such as a 3'UTR, a histone stem-loop or a poly C sequence, may also be present in more than one copy in the modified RNA according to the invention. This holds true in particular for bi- or multicistronic RNAs. A modified RNA according to the invention may comprise combinations of several distinct modifications, such as GC-enrichment in combination with any of, for instance, a 5'UTR, a poly C sequence, a poly A sequence, a 3'UTR or a histone stem-loop, wherein each distinct modification may be present in the form of a single copy per RNA or in the form of multiple copies per RNA.

Preferred embodiments of the RNA according to the invention may therefore comprise, for example,
5'-coding region-histone stem-loop-3';
5'-coding region-histone stem-loop-poly(A)/(C) sequence-3'; or
5'-coding region-poly(A)/(C) sequence-histone stem-loop-3'; or
5'-coding region-histone stem-loop-polyadenylation signal-3'; or
5'-coding region-polyadenylation signal-histone stem-loop-3'; or
5'-coding region-histone stem-loop-histone stem-loop-poly(A)/(C) sequence-3'; or
5'-coding region-histone stem-loop-histone stem-loop-polyadenylation signal-3'; or
5'-coding region-poly(A)/(C) sequence-poly(A)/(C) sequence-histone stem-loop-3'; etc.,
wherein the coding region preferably comprises or consists of a GC enriched sequence as defined herein, and
wherein, a 5'UTR element is preferably present on the 5' side of the coding region and/or a 3'UTR element is preferably present between the 3' end of the coding region and the 3' terminus of the RNA.

A specific embodiment of the modified RNA may comprise, for instance, any one of the combinations of structural features and modifications as listed below:
5'-coding region-poly(A) sequence-3';
5'-coding region-poly(A) sequence-poly(C) sequence-3';
5'-coding region-poly(A) sequence-poly(C) sequence-histone stem-loop-3';
5'-coding region-3'UTR-poly(A) sequence-3';
5'-coding region-3'UTR-poly(A) sequence-poly(C) sequence-3';
5'-coding region-3'UTR-poly(A) sequence-poly(C) sequence-histone stem-loop-3';
5'-5'UTR-coding region-poly(A) sequence-3';
5'-5'UTR-coding region-poly(A) sequence-poly(C) sequence-3';
5'-5'UTR-coding region-poly(A) sequence-poly(C) sequence-histone stem-loop-3';
5'-coding region-3'UTR-poly(A) sequence-3';
5'-5'UTR-coding region-3'UTR-poly(A) sequence-poly(C) sequence-3';
5'-5'UTR-coding region-3'UTR-poly(A) sequence-poly(C) sequence-histone stem-loop-3';
wherein the coding region preferably comprises or consists of a GC enriched sequence as defined herein.

Encoded Proteins:

In a preferred embodiment, the modified RNA comprises at least one open reading frame, which encodes a therapeutic protein or peptide. In another embodiment, an antigen is encoded by the at least one open reading frame, such as a pathogenic antigen, a tumour antigen, an allergenic antigen or an autoimmune antigen. Therein, the administration of the modified RNA encoding the antigen is used in a genetic vaccination approach against a disease involving said antigen.

In an alternative embodiment, an antibody is encoded by the at least one open reading frame of the modified RNA according to the invention.

In a preferred embodiment, the modified RNA according to the invention does not comprise a reporter gene or a marker gene. Preferably, the modified RNA according to the invention does not encode, for instance, luciferase; green fluorescent protein (GFP) and its variants (such as eGFP, RFP or BFP); α-globin; hypoxanthine-guanine phosphoribosyltransferase (HGPRT); β-galactosidase; galactokinase; alkaline phosphatase; secreted embryonic alkaline phosphatase (SEAP)) or a resistance gene (such as a resistance gene against neomycin, puromycin, hygromycin and zeocin). In a preferred embodiment, the modified RNA according to the invention does not encode luciferase. In another embodiment, the modified RNA according to the invention does not encode GFP or a variant thereof.

Antigens:

Pathogenic Antigens:

The modified RNA according to the present invention may encode a protein or a peptide, which comprises a pathogenic antigen or a fragment, variant or derivative thereof. Such pathogenic antigens are derived from pathogenic organisms, in particular bacterial, viral or protozoological (multicellular) pathogenic organisms, which evoke an immunological reaction in a subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease, which are preferably selected from antigens derived from the pathogens *Acinetobacter baumannii*, *Anaplasma genus*, *Anaplasma phagocytophilum*, *Ancylostoma braziliense*, *Ancylostoma duodenale*, *Arcanobacterium haemolyticum*, *Ascaris lumbricoides*, *Aspergillus genus*, Astroviridae, *Babesia genus*, *Bacillus anthracis*, *Bacillus cereus*, *Bartonella henselae*, BK virus, *Blastocystis hominis*, *Blastomyces dermatitidis*, *Bordetella pertussis*, *Borrelia burgdorferi*, *Borrelia genus*, *Borrelia spp*, *Brucella genus*, *Brugia malayi*, Bunyaviridae family, *Burkholderia cepacia* and other *Burkholderia* species, *Burkholderia mallei*, *Burkholderia pseudomallei*, Caliciviridae family, *Campylobacter genus*, *Candida albicans*, *Candida spp*, *Chlamydia trachomatis*, *Chlamydophila pneumoniae*, *Chlamydophila psittaci*, CJD prion, *Clonorchis sinensis*, *Clostridium botulinum*, *Clostridium difficile*, *Clostridium perfringens*, *Clostridium perfringens*, *Clostridium spp*, *Clostridium tetani*, *Coccidioides spp*, coronaviruses, *Corynebacterium diphtheriae*, *Coxiella burnetii*, Crimean-Congo hemorrhagic fever virus, *Cryptococcus neoformans*, *Cryptosporidium genus*, Cytomegalovirus (CMV), *Dengue* viruses (DEN-1, DEN-2, DEN-3 and DEN-4), *Dientamoeba fragilis*, Ebolavirus (EBOV), *Echinococcus genus*, *Ehrlichia chaffeensis*, *Ehrlichia ewingii*, *Ehrlichia genus*, *Entamoeba histolytica*, *Enterococcus genus*, *Enterovirus genus*, Enteroviruses, mainly Coxsackie A virus and *Enterovirus* 71 (EV71), *Epidermophyton spp*, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis*, *Fusobacterium genus*, *Geotrichum candidum*, *Giardia intestinalis*, *Gnathostoma spp*, GSS prion, Guanarito virus, *Haemophilus ducreyi*, *Haemophilus influenzae*, *Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, Kingella kingae, *Klebsiella granulomatis*, Kuru prion, Lassa virus, *Legionella pneumophila*, *Leishmania genus*, *Leptospira genus*, *Listeria monocytogenes*, Lymphocytic choriomeningitis virus (LCMV), Machupo virus, *Malassezia spp*, Marburg virus, Measles virus, *Metagonimus yokagawai*, Microsporidia phylum, Molluscum contagiosum virus (MCV), Mumps virus, *Mycobacterium leprae* and *Mycobacterium lepromatosis*, *Mycobacterium tuberculosis*, *Mycobacterium ulcerans*, *Mycoplasma pneumoniae*, *Naegleria fowleri*, *Necator americanus*, *Neisseria gonorrhoeae*, *Neisseria meningitidis*, *Nocardia asteroides*, *Nocardia spp*, *Onchocerca volvulus*, *Orientia tsutsugamushi*, Orthomyxoviridae family (Influenza), *Paracoccidioides brasiliensis*, *Paragonimus spp*, *Paragonimus westermani*, Parvovirus B19, *Pasteurella genus*, *Plasmodium genus*, *Pneumocystis jirovecii*, Poliovirus, Rabies virus, Respiratory syncytial virus (RSV), Rhinovirus, rhinoviruses, *Rickettsia akari*, *Rickettsia genus*, *Rickettsia prowazekii*, *Rickettsia rickettsii*, *Rickettsia typhi*, Rift Valley fever virus, Rotavirus, Rubella virus, Sabia virus, *Salmonella genus*, *Sarcoptes scabiei*, SARS coronavirus, *Schistosoma genus*, *Shigella genus*, Sin Nombre virus, Hantavirus, *Sporothrix schenckii*, *Staphylococcus genus*, *Staphylococcus genus*, *Streptococcus agalactiae*, *Streptococcus pneumoniae*, *Streptococcus pyogenes*, *Strongyloides stercoralis*, *Taenia genus*, *Taenia solium*, Tick-borne encephalitis virus (TBEV), *Toxocara canis* or *Toxocara cati*, *Toxoplasma gondii*, *Treponema pallidum*, *Trichinella spiralis*, *Trichomonas vaginalis*, *Trichophyton spp*, *Trichuris trichiura*, *Trypanosoma brucei*, *Trypanosoma cruzi*, *Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica*, *Yersinia pestis*, and *Yersinia pseudotuberculosis*.

In this context particularly preferred are antigens from the pathogens selected from Influenza virus, respiratory syncytial virus (RSV), Herpes simplex virus (HSV), human Papilloma virus (HPV), Human immunodeficiency virus (HIV), Plasmodium, Staphylococcus aureus, Dengue virus, *Chlamydia trachomatis*, Cytomegalovirus (CMV), Hepatitis B virus (HBV), *Mycobacterium tuberculosis*, Rabies virus, and Yellow Fever Virus.

In a preferred embodiment, the modified RNA according to the invention encodes a Rabies virus protein or peptide or an antigenic fragment thereof. Preferably, the modified RNA according to the invention encodes an antigenic protein or peptide selected from the group consisting of glycoprotein G (RAV-G), nucleoprotein N (RAV-N), phosphoprotein P (RAV-P), matrix protein M (RAV-M) or RNA polymerase L (RAV-L) of Rabies virus, or a fragment, variant or derivative thereof.

In another preferred embodiment, the modified RNA according to the invention encodes a respiratory syncytial virus (RSV) protein or peptide or an antigenic fragment thereof. Preferably, the modified RNA according to the invention encodes an antigenic protein or peptide selected from the group consisting of the fusion protein F, the glycoprotein G, the short hydrophobic protein SH, the matrix protein M, the nucleoprotein N, the large polymerase L, the M2-1 protein, the M2-2 protein, the phosphoprotein P, the non-structural protein NS1 or the non-structural protein NS2 of respiratory syncytial virus (RSV), or a fragment, variant or derivative thereof.

Tumour Antigens:

In a further embodiment, the modified RNA according to the present invention may encode a protein or a peptide, which comprises a peptide or protein comprising a tumour antigen, a fragment, variant or derivative of said tumour antigen, preferably, wherein the tumour antigen is a melanocyte-specific antigen, a cancer-testis antigen or a tumour-specific antigen, preferably a CT-X antigen, a non-X CT-antigen, a binding partner for a CT-X antigen or a binding partner for a non-X CT-antigen or a tumour-specific antigen, more preferably a CT-X antigen, a binding partner for a non-X CT-antigen or a tumour-specific antigen or a fragment, variant or derivative of said tumour antigen; and wherein each of the nucleic acid sequences encodes a different peptide or protein; and wherein at least one of the nucleic acid sequences encodes for 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP-2/6b, TRP/INT2, TRP-p8, tyrosinase, UPA, VEGFR1, VEGFR-2/FLK-1, WT1 and a immunoglobulin idiotype of a lymphoid blood cell or a T cell receptor idiotype of a lymphoid blood cell, or a fragment, variant or derivative of said tumour antigen; preferably survivin or a homologue thereof, an antigen from the MAGE-family or a binding partner thereof or a fragment, variant or derivative of said tumour antigen.

Particularly preferred in this context are the tumour antigens NY-ESO-1, 5T4, MAGE-C1, MAGE-C2, Survivin, Muc-1, PSA, PSMA, PSCA, STEAP and PAP.

In this context, it is particularly preferred that at least one modified RNA administered by jet injection according to the invention encodes one of the following combinations of antigens:

Muc-1, PSA, PSMA, PSCA, and STEAP
Muc-1, PSA, PSMA, PSCA, and PAP
Muc-1, PSA, PSMA, STEAP and PAP
Muc-1, PSA, PSCA, STEAP and PAP
Muc-1, PSMA, PSCA, STEAP and PAP
PSA, PSMA, PSCA, STEAP and PAP
Muc-1, PSA, PSMA, PSCA, STEAP and PAP In another embodiment, it is particularly preferred that at least one modified RNA administered by jet injection according to the invention encodes one of the following combinations of antigens:

NY-ESO-1, 5T4, MAGE-C1, MAGE-C2, and Survivin
NY-ESO-1, 5T4, MAGE-C1, MAGE-C2, and Muc-1
NY-ESO-1, 5T4, MAGE-C1, Survivin and Muc-1
NY-ESO-1, 5T4, MAGE-C2, Survivin and Muc-1
NY-ESO-1, MAGE-C1, MAGE-C2, Survivin and Muc-1
5T4, MAGE-C1, MAGE-C2, Survivin and Muc-1
NY-ESO-1, 5T4, MAGE-C1, MAGE-C2, Survivin and Muc-1

In a preferred embodiment, the modified RNA administered by jet injection encodes a protein or a peptide, which comprises a therapeutic protein or a fragment, variant or derivative thereof.

Therapeutic proteins as defined herein are peptides or proteins, which are beneficial for the treatment of any inherited or acquired disease, or which improves the condition of an individual. Particularly, therapeutic proteins play a big role in the creation of therapeutic agents that could modify and repair genetic errors, destroy cancer cells or pathogen infected cells, treat immune system disorders, treat metabolic or endocrine disorders, among other functions. For instance, Erythropoietin (EPO), a protein hormone can be utilized in treating patients with erythrocyte deficiency, which is a common cause of kidney complications. Furthermore adjuvant proteins, therapeutic antibodies are encompassed by therapeutic proteins and also hormone replacement therapy, which is e.g. used in the therapy of women in menopause. In more recent approaches, somatic cells of a patient are used to reprogram them into pluripotent stem cells, which replace the disputed stem cell therapy. Also these proteins used for reprogramming of somatic cells or used for differentiating of stem cells are defined herein as therapeutic proteins. Furthermore, therapeutic proteins may be used for other purposes, e.g. wound healing, tissue regeneration, angiogenesis, etc.

Therefore therapeutic proteins can be used for various purposes including treatment of various diseases like e.g. infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired.

In this context, particularly preferred therapeutic proteins which can be used inter alia in the treatment of metabolic or endocrine disorders are selected from: Acid sphingomyelinase (Niemann-Pick disease), Adipotide (obesity), Agalsidase-beta (human galactosidase A) (Fabry disease; prevents accumulation of lipids that could lead to renal and cardiovascular complications), Alglucosidase (Pompe disease (glycogen storage disease type II)), alpha-galactosidase A (alpha-GAL A, Agalsidase alpha) (Fabry disease), alpha-glucosidase (Glycogen storage disease (GSD), Morbus Pompe), alpha-L-iduronidase (mucopolysaccharidoses (MPS), Hurler syndrome, Scheie syndrome), alpha-N-acetylglucosaminidase (Sanfilippo syndrome), Amphiregulin (cancer, metabolic disorder), Angiopoietin ((Ang1, Ang2, Ang3, Ang4, ANGPTL2, ANGPTL3, ANGPTL4, ANGPTL5, ANGPTL6, ANGPTL7) (angiogenesis, stabilize vessels), Betacellulin (metabolic disorder), Beta-glucuronidase (Sly syndrome), Bone morphogenetic protein BMPs (BMP1, BMP2, BMP3, BMP4, BMP5, BMP6, BMP7, BMP8a, BMP8b, BMP10, BMP15) (regenerative effect, bone-related conditions, chronic kidney disease (CKD)), CLN6 protein (CLN6 disease—Atypical Late Infantile, Late Onset variant, Early Juvenile, Neuronal Ceroid Lipofuscinoses (NCL)), Epidermal growth factor (EGF) (wound healing, regulation of cell growth, proliferation, and differentiation), Epigen (metabolic disorder), Epiregulin (metabolic disorder), Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23) (wound healing, angiogenesis, endocrine disorders, tissue regeneration), Galsulphase (Mucopolysaccharidosis VI), Ghrelin (irritable bowel syndrome (IBS), obesity, Prader-Willi syndrome, type II diabetes mellitus), Glucocerebrosidase (Gaucher's disease), GM-CSF (regenerative effect, production of white blood cells, cancer), Heparin-binding EGF-like growth factor (HB-EGF) (wound healing, cardiac hypertrophy and heart development and function), Hepatocyte growth factor HGF (regenerative effect, wound healing), Hepcidin (iron metabolism disorders, Beta-thalassemia), Human albumin (Decreased production of albumin (hypoproteinaemia), increased loss of albumin (nephrotic syndrome), hypovolaemia, hyperbilirubinaemia), Idursulphase (Iduronate-2-sulphatase) (Mucopolysaccharidosis II (Hunter syndrome)), Integrins αVβ, αVβ5 and α5β1 (Bind matrix macromolecules and proteinases, angiogenesis), luduronate sulfatase (Hunter syndrome), Laronidase (Hurler and Hurler-Scheie forms of mucopolysaccharidosis I), N-acetylgalactosamine-4-sulfatase (rhASB; galsulfase, Arylsulfatase A (ARSA), Arylsulfatase B (ARSB)) (arylsulfatase B deficiency, Maroteaux-Lamy syndrome, mucopolysaccharidosis VI), N-acetylglucosamine-6-sulfatase (Sanfilippo syndrome), Nerve growth factor (NGF, Brain-Derived Neurotrophic Factor (BDNF), Neurotrophin-3 (NT-3), and Neurotrophin 4/5 (NT-4/5) (regenerative effect, cardiovascular diseases, coronary atherosclerosis, obesity, type 2 diabetes, metabolic syndrome, acute coronary syndromes, dementia, depression, schizophrenia, autism, Rett syndrome, anorexia nervosa, bulimia nervosa, wound healing, skin ulcers, corneal ulcers, Alzheimer's disease), Neuregulin (NRG1, NRG2, NRG3, NRG4) (metabolic disorder, schizophrenia), Neuropilin (NRP-1, NRP-2) (angiogenesis, axon guidance, cell survival, migration), Obestatin (irritable bowel syndrome (IBS), obesity, Prader-Willi syndrome, type II diabetes mellitus), Platelet Derived Growth factor (PDGF (PDFF-A, PDGF-B, PDGF-C, PDGF-D) (regenerative effect, wound healing, disorder in angiogenesis, Arteriosclerosis, Fibrosis, cancer), TGF beta receptors (endoglin, TGF-beta 1 receptor, TGF-beta 2 receptor, TGF-beta 3 receptor) (renal fibrosis, kidney disease, diabetes, ultimately end-stage renal disease (ESRD), angiogenesis), Thrombopoietin (THPO) (Megakaryocyte growth and development factor (MGDF)) (platelets disorders, platelets for donation, recovery of platelet counts after myelosuppressive chemotherapy), Transforming Growth factor (TGF (TGF-a, TGF-beta (TGFbeta1, TGFbeta2, and TGFbeta3))) (regenerative effect, wound healing, immunity, cancer, heart disease, diabetes, Marfan syndrome, Loeys-Dietz syndrome), VEGF (VEGF-A, VEGF-B, VEGF-C, VEGF-D, VEGF-E, VEGF-F und PIGF) (regenerative effect, angiogenesis, wound healing, cancer, permeability), Nesiritide (Acute decompensated congestive heart failure), Trypsin (Decubitus ulcer, varicose ulcer, debridement of eschar, dehiscent wound, sunburn, meconium ileus), adrenocorticotrophic hormone (ACTH) ("Addison's disease, Small cell carcinoma, Adrenoleukodystrophy, Congenital adrenal hyperplasia, Cushing's syndrome, Nelson's syndrome, Infantile spasms), Atrial-natriuretic peptide (ANP) (endocrine disorders), Cholecystokinin (diverse), Gastrin (hypogastrinemia), Leptin (Diabetes, hypertriglyceridemia, obesity), Oxytocin (stimulate breastfeeding, non-progression of parturition), Somatostatin (symptomatic treatment of carcinoid syndrome, acute variceal bleeding, and acromegaly, polycystic diseases of the liver and kidney, acromegaly and symptoms caused by neuroendocrine tumors), Vasopressin (antidiuretic hormone) (diabetes insipidus), Calcitonin (Postmenopausal osteoporosis, Hypercalcaemia, Paget's disease, Bone metastases, Phantom limb pain, Spinal Stenosis), Exenatide (Type 2 diabetes resistant to treatment with metformin and a sulphonylurea), Growth hormone (GH), somatotropin (Growth failure due to GH deficiency or chronic renal insufficiency, Prader-Willi syndrome, Turner syndrome, AIDS wasting or cachexia with antiviral therapy), Insulin (Diabetes mellitus, diabetic ketoacidosis, hyperkalaemia), Insulin-like growth factor 1 IGF-1 (Growth failure in children with GH gene deletion or severe primary IGF1 deficiency, neurodegenerative disease, cardiovascular diseases, heart failure), Mecasermin rinfabate, IGF-1 analog (Growth failure in children with GH gene deletion or severe primary IGF1 deficiency, neurodegenerative disease, cardiovascular diseases, heart failure), Mecasermin, IGF-1 analog (Growth failure in children with GH gene deletion or severe primary IGF1 deficiency, neurodegenerative disease, cardiovascular diseases, heart failure), Pegvisomant (Acromegaly), Pramlintide (Diabetes mellitus, in combination with insulin), Teriparatide (human parathyroid hormone residues 1-34) (Severe osteoporosis), Becaplermin (Debridement adjunct for diabetic ulcers), Dibotermin-alpha (Bone morphogenetic protein 2) (Spinal fusion surgery, bone injury repair), Histrelin acetate (gonadotropin releasing hormone; GnRH) (Precocious puberty), Octreotide (Acromegaly, symptomatic relief of VIP-secreting adenoma and metastatic carcinoid tumours), and Palifermin (keratinocyte growth factor; KGF) (Severe oral mucositis in patients undergoing chemotherapy, wound healing). (in brackets is the particular disease for which the therapeutic protein is used in the treatment). These and other proteins are understood to be therapeutic, as they are meant to treat the subject by replacing its defective endogenous production of a functional protein in sufficient amounts. Accordingly, such therapeutic proteins are typically mammalian, in particular human proteins.

For the treatment of blood disorders, diseases of the circulatory system, diseases of the respiratory system, cancer or tumour diseases, infectious diseases or immunedeficiencies following therapeutic proteins may be used: Alteplase (tissue plasminogen activator; tPA) (Pulmonary embolism, myocardial infarction, acute ischaemic stroke, occlusion of central venous access devices), Anistreplase (Thrombolysis), Antithrombin III (AT-III) (Hereditary AT-III deficiency, Thromboembolism), Bivalirudin (Reduce blood-clotting risk in coronary angioplasty and heparin-induced thrombocytopaenia), Darbepoetin-alpha (Treatment of anaemia in patients with chronic renal insufficiency and chronic renal failure (+/− dialysis)), Drotrecogin-alpha (activated protein C) (Severe sepsis with a high risk of death), Erythropoietin, Epoetin-alpha, erythropoietin, erthropoyetin (Anaemia of chronic disease, myleodysplasia, anaemia due to renal failure or chemotherapy, preoperative preparation), Factor IX (Haemophilia B), Factor VIIa (Haemorrhage in patients with haemophilia A or B and inhibitors to factor VIII or factor IX), Factor VIII (Haemophilia A), Lepirudin (Heparin-induced thrombocytopaenia), Protein C concentrate (Venous thrombosis, Purpura fulminans), Reteplase (deletion mutein of tPA) (Management of acute myocardial infarction, improvement of ventricular function), Streptokinase (Acute evolving transmural myocardial infarction, pulmonary embolism, deep vein thrombosis, arterial thrombosis or embolism, occlusion of arteriovenous cannula), Tenecteplase (Acute myocardial infarction), Urokinase (Pulmonary embolism), Angiostatin (Cancer), Anti-CD22 immunotoxin (Relapsed CD33+ acute myeloid leukaemia), Denileukin diftitox (Cutaneous T-cell lymphoma (CTCL)), Immunocyanin (bladder and prostate cancer), MPS (Metallopanstimulin) (Cancer), Aflibercept (Non-small cell lung cancer (NSCLC), metastatic colorectal cancer (mCRC), hormone-refractory metastatic prostate cancer, wet macular degeneration), Endostatin (Cancer, inflammatory diseases like rheumatoid arthritis as well as Crohn's disease, diabetic retinopathy, psoriasis, and endometriosis), Collagenase (Debridement of chronic dermal ulcers and severely burned areas, Dupuytren's contracture, Peyronie's disease), Human deoxy-ribonuclease I, dornase (Cystic fibrosis; decreases respiratory tract infections in selected patients with FVC greater than 40% of predicted), Hyaluronidase (Used as an adjuvant to increase the absorption and dispersion of injected drugs, particularly anaesthetics in ophthalmic surgery and certain imaging agents), Papain (Debridement of necrotic tissue or liquefication of slough in acute and chronic lesions, such as pressure ulcers, varicose and diabetic ulcers, burns, postoperative wounds, pilonidal cyst wounds, carbuncles, and other wounds), L-Asparaginase (Acute lymphocytic leukaemia, which requires exogenous asparagine for proliferation), Peg-asparaginase (Acute lymphocytic leukaemia, which requires exogenous asparagine for proliferation), Rasburicase (Paediatric patients with leukaemia, lymphoma, and solid tumours who are undergoing anticancer therapy that may cause tumour lysis syndrome), Human chorionic gonadotropin (HCG) (Assisted reproduction), Human follicle-stimulating hormone (FSH) (Assisted reproduction), Lutropin-alpha (Infertility with luteinizing hormone deficiency), Prolactin (Hypoprolactinemia, serum prolactin deficiency, ovarian dysfunction in women, anxiety, arteriogenic erectile dysfunction, premature ejaculation, oligozoospermia, asthenospermia, hypofunction of seminal vesicles, hypoandrogenism in men), alpha-1-Proteinase inhibitor (Congenital antitrypsin deficiency), Lactase (Gas, bloating, cramps and diarrhoea due to inability to digest lactose), Pancreatic enzymes (lipase, amylase, protease) (Cystic fibrosis, chronic pancreatitis, pancreatic insufficiency, post-Billroth II gastric bypass surgery, pancreatic duct obstruction, steatorrhoea, poor digestion, gas, bloating), Adenosine deaminase (pegademase bovine, PEG-ADA) (Severe combined immunodeficiency disease due to adenosine deaminase deficiency), Abatacept (Rheumatoid arthritis (especially when refractory to TNFa inhibition)), Alefacept (Plaque Psoriasis), Anakinra (Rheumatoid arthritis), Etanercept (Rheumatoid arthritis, polyarticular-course juvenile rheumatoid arthritis, psoriatic arthritis, ankylosing spondylitis, plaque psoriasis, ankylosing spondylitis), Interleukin-1 (IL-1) receptor antagonist, Anakinra (inflammation and cartilage degradation associated with rheumatoid arthritis), Thymulin (neurodegenerative diseases, rheumatism, anorexia nervosa), TNF-alpha antagonist (autoimmune disorders such as rheumatoid arthritis, ankylosing spondylitis, Crohn's disease, psoriasis, hidradenitis suppurativa, refractory asthma), Enfuvirtide (HIV-1 infection), and Thymosin α1 (Hepatitis B and C).

(in brackets is the particular disease, for which the therapeutic protein is used in the treatment)

Furthermore, adjuvant or immunostimulating proteins are also encompassed in the term therapeutic proteins. Adjuvant or immunostimulating proteins may be used in this context to induce, alter or improve an immune response in an individual to treat a particular disease or to ameliorate the condition of the individual.

In this context, adjuvant proteins may be selected from mammalian, in particular human adjuvant proteins, which typically comprise any human protein or peptide, which is capable of eliciting an innate immune response (in a mammal), e.g. as a reaction of the binding of an exogenous TLR ligand to a TLR. More preferably, human adjuvant proteins are selected from the group consisting of proteins, which are components and ligands of the signalling networks of the pattern recognition receptors including TLR, NLR and RLH, including TLR1, TLR2, TLR3, TLR4, TLR5, TLR6, TLR7, TLR8, TLR9, TLR10, TLR11; NOD1, NOD2, NOD3, NOD4, NOD5, NALP1, NALP2, NALP3, NALP4, NALP5, NALP6, NALP6, NALP7, NALP7, NALP8, NALP9, NALP10, NALP11, NALP12, NALP13, NALP14,1 IPAF, NAIP, CIITA, RIG-I, MDA5 and LGP2, the signal transducers of TLR signaling including adaptor proteins including e.g. Trif and Cardif; components of the Small-GTPases signalling (RhoA, Ras, Rac1, Cdc42, Rab etc.), components of the PIP signalling (PI3K, Src-Kinases, etc.), components of the MyD88-dependent signalling (MyD88, IRAK1, IRAK2, IRAK4, TIRAP, TRAF6 etc.), components of the MyD88-independent signalling (TICAM1, TICAM2, TRAF6, TBK1, IRF3, TAK1, IRAK1 etc.); the activated kinases including e.g. Akt, MEKK1, MKK1, MKK3, MKK4, MKK6, MKK7, ERK1, ERK2, GSK3, PKC kinases, PKD kinases, GSK3 kinases, JNK, p38MAPK, TAK1, IKK, and TAK1; the activated transcription factors including e.g. NF-κB, c-Fos, c-Jun, c-Myc, CREB, AP-1, Elk-1, ATF2, IRF-3, IRF-7.

Mammalian, in particular human adjuvant proteins may furthermore be selected from the group consisting of heat shock proteins, such as HSP10, HSP60, HSP65, HSP70, HSP75 and HSP90, gp96, Fibrinogen, TypIII repeat extra domain A of fibronectin; or components of the complement system including Clq, MBL, Clr, Cls, C2b, Bb, D, MASP-1, MASP-2, C4b, C3b, C5a, C3a, C4a, C5b, C6, C7, C8, C9, CR1, CR2, CR3, CR4, C1qR, CIINH, C4 bp, MCP, DAF, H, I, P and CD59, or induced target genes including e.g.

Beta-Defensin, cell surface proteins; or human adjuvant proteins including trif, flt-3 ligand, Gp96 or fibronectin, etc., or any species homolog of any of the above human adjuvant proteins.

Mammalian, in particular human adjuvant proteins may furthermore comprise cytokines which induce or enhance an innate immune response, including IL-1 alpha, IL1 beta, IL-2, IL-6, IL-7, IL-8, IL-9, IL-12, IL-13, IL-15, IL-16, IL-17, IL-18, IL-21, IL-23, TNFalpha, IFNalpha, IFNbeta, IFNgamma, GM-CSF, G-CSF, M-CSF; chemokines including IL-8, IP-10, MCP-1, MIP-lalpha, RANTES, Eotaxin, CCL21; cytokines which are released from macrophages, including IL-1, IL-6, IL-8, IL-12 and TNF-alpha; as well as IL-IR1 and IL-1 alpha.

Therapeutic proteins for the treatment of blood disorders, diseases of the circulatory system, diseases of the respiratory system, cancer or tumour diseases, infectious diseases or immunedeficiencies or adjuvant proteins are typically proteins of mammalian origin, preferably of human origin, depending on which animal shall be treated. A human subject, for example, is preferably treated by a therapeutic protein of human origin.

Pathogenic adjuvant proteins, typically comprise a pathogenic adjuvant protein, which is capable of eliciting an innate immune response (in a mammal), more preferably selected from pathogenic adjuvant proteins derived from bacteria, protozoa, viruses, or fungi, etc., e.g., bacterial (adjuvant) proteins, protozoan (adjuvant) proteins (e.g. profilin—like protein of *Toxoplasma gondii*), viral (adjuvant) proteins, or fungal (adjuvant) proteins, etc.

Particularly, bacterial (adjuvant) proteins may be selected from the group consisting of bacterial heat shock proteins or chaperons, including Hsp60, Hsp70, Hsp90, Hsp100; OmpA (Outer membrane protein) from gram-negative bacteria; bacterial porins, including OmpF; bacterial toxins, including pertussis toxin (PT) from *Bordetella pertussis*, pertussis adenylate cyclase toxin CyaA and CyaC from *Bordetella pertussis*, PT-9K/129G mutant from pertussis toxin, pertussis adenylate cyclase toxin CyaA and CyaC from *Bordetella pertussis*, tetanus toxin, cholera toxin (CT), cholera toxin B-subunit, CTK63 mutant from cholera toxin, CTE112K mutant from CT, *Escherichia coli* heat-labile enterotoxin (LT), B subunit from heat-labile enterotoxin (LTB) *Escherichia coli* heat-labile enterotoxin mutants with reduced toxicity, including LTK63, LTR72; phenol-soluble modulin; neutrophil-activating protein (HP-NAP) from *Helicobacter pylori*; Surfactant protein D; Outer surface protein A lipoprotein from *Borrelia burgdorferi*, Ag38 (38 kDa antigen) from *Mycobacterium tuberculosis*; proteins from bacterial fimbriae; Enterotoxin CT of *Vibrio cholerae*, Pilin from pili from gram negative bacteria, and Surfactant protein A; etc., or any species homolog of any of the above bacterial (adjuvant) proteins.

Bacterial (adjuvant) proteins may also comprise bacterial flagellins. In the context of the present invention, bacterial flagellins may be selected from flagellins from organisms including, without being limited thereto, *Agrobacterium, Aquifex, Azospirillum, Bacillus, Bartonella, Bordetella, Borrelia, Burkholderia, Campylobacter, Caulobacte, Clostridium, Escherichia, Helicobacter, Lachnospiraceae, Legionella, Listeria, Proteus, Pseudomonas, Rhizobium, Rhodobacter, Roseburia, Salmonella, Serpulina, Serratia, Shigella, Treponema, Vibrio, Wolinella, Yersinia*, more preferably from flagellins from the species including, without being limited thereto, *Agrobacterium tumefaciens, Aquifex pyrophilus, Azospirillum brasilense, Bacillus subtilis, Bacillus thuringiensis, Bartonella bacilliformis, Bordetella bronchiseptica, Borrelia burgdorferi, Burkholderia cepacia, Campylobacter jejuni, Caulobacter crescentus, Clostridium botulinum* strain Bennett clone 1, *Escherichia coli, Helicobacter pylori, Lachnospiraceae bacterium, Legionella pneumophila, Listeria monocytogenes, Proteus mirabilis, Pseudomonas aeroguinosa, Pseudomonas syringae, Rhizobium meliloti, Rhodobacter sphaeroides, Roseburia cecicola, Roseburis hominis, Salmonella typhimurium, Salmonella bongori, Salmonella typhi, Salmonella enteritidis, Serpulina hyodysenteriae, Serratia marcescens, Shigella boydii, Treponema phagedenis, Vibrio alginolyticus, Vibrio cholerae, Vibrio parahaemolyticus, Wolinella succinogenes* and *Yersinia enterocolitica*.

Protozoan (adjuvant) proteins are a further example of pathogenic adjuvant proteins. Protozoan (adjuvant) proteins may be selected in this context from any protozoan protein showing adjuvant properties, more preferably, from the group consisting of, without being limited thereto, Tc52 from *Trypanosoma cruzi*, PFTG from *Trypanosoma gondii*, Protozoan heat shock proteins, LeIF from *Leishmania* spp., profiling-like protein from *Toxoplasma gondii*, etc.

Viral (adjuvant) proteins are another example of pathogenic adjuvant proteins. In this context, viral (adjuvant) proteins may be selected from any viral protein showing adjuvant properties, more preferably, from the group consisting of, without being limited thereto, Respiratory Syncytial Virus fusion glycoprotein (F-protein), envelope protein from MMT virus, mouse leukemia virus protein, Hemagglutinin protein of wild-type measles virus, etc.

Fungal (adjuvant) proteins are even a further example of pathogenic adjuvant proteins. In the context of the present invention, fungal (adjuvant) proteins may be selected from any fungal protein showing adjuvant properties, more preferably, from the group consisting of, fungal immunomodulatory protein (FIP; LZ-8), etc.

Finally, adjuvant proteins may furthermore be selected from the group consisting of, Keyhole limpet hemocyanin (KLH), OspA, etc.

In a further embodiment, therapeutic proteins may be used for hormone replacement therapy, particularly for the therapy of women in the menopause. These therapeutic proteins are preferably selected from oestrogens, progesterone or progestins, and sometimes testosterone.

Furthermore, therapeutic proteins may be used for reprogramming of somatic cells into pluri- or omnipotent stem cells. For this purpose, several factors are described, particularly Oct-3/4, Sox gene family (Sox1, Sox2, Sox3, and Sox15), Klf family (Klf1, Klf2, Klf4, and Klf5), Myc family (c-myc, L-myc, and N-myc), Nanog, and LIN28.

As mentioned above, also therapeutic antibodies are defined herein as therapeutic proteins. These therapeutic antibodies are preferably selected from antibodies, which are used inter alia for the treatment of cancer or tumour diseases, e.g. 131I-tositumomab (Follicular lymphoma, B cell lymphomas, leukemias), 3F8 (Neuroblastoma), 8H9, Abagovomab (Ovarian cancer), Adecatumumab (Prostate and breast cancer), Afutuzumab (Lymphoma), Alacizumab pegol, Alemtuzumab (B-cell chronic lymphocytic leukaemia, T-cell-Lymphoma), Amatuximab, AME-133v (Follicular lymphoma, cancer), AMG 102 (Advanced Renal Cell Carcinoma), Anatumomab mafenatox (Non-small cell lung carcinoma), Apolizumab (Solid Tumors, Leukemia, Non-Hodgkin-Lymphoma, Lymphoma), Bavituximab (Cancer, viral infections), Bectumomab (Non-Hodgkin's lymphoma), Belimumab (Non-Hodgkin lymphoma), Bevacizumab (Colon Cancer, Breast Cancer, Brain and Central Nervous System Tumors, Lung Cancer, Hepatocellular Carcinoma, Kidney Cancer, Breast Cancer, Pancreatic Cancer, Bladder Cancer, Sarcoma, Melanoma, Esophageal Cancer; Stomach Cancer, Metastatic Renal Cell Carcinoma; Kidney Cancer, Glioblastoma, Liver Cancer, Proliferative Diabetic Retinopathy, Macular Degeneration), Bivatuzumab mertansine (Squamous cell carcinoma), Blinatumomab, Brentuximab vedotin (Hematologic cancers), Cantuzumab (Colon Cancer, Gastric Cancer, Pancreatic Cancer, NSCLC), Cantuzumab mertansine (Colorectal cancer), Cantuzumab ravtansine (Cancers), Capromab pendetide (Prostate cancer), Carlumab, Catumaxomab (Ovarian Cancer, Fallopian Tube Neoplasms, Peritoneal Neoplasms), Cetuximab (Metastatic colorectal cancer and head and neck cancer), Citatuzumab bogatox (Ovarian cancer and other solid tumors), Cixutumumab (Solid tumors), Clivatuzumab tetraxetan (Pancreatic cancer), CNTO 328 (B-Cell Non-Hodgkin's Lymphoma, Multiple Myeloma, Castleman's Disease, ovarian cancer), CNTO 95 (Melanoma), Conatumumab, Dacetuzumab (Hematologic cancers), Dalotuzumab, Denosumab (Myeloma, Giant Cell Tumor of Bone, Breast Cancer, Prostate Cancer, Osteoporosis), Detumomab (Lymphoma), Drozitumab, Ecromeximab (Malignant melanoma), Edrecolomab (Colorectal carcinoma), Elotuzumab (Multiple myeloma), Elsilimomab, Enavatuzumab, Ensituximab, Epratuzumab (Autoimmune diseases, Systemic Lupus Erythematosus, Non-Hodgkin-Lymphoma, Leukemia), Ertumaxomab (Breast cancer), Ertumaxomab (Breast Cancer), Etaracizumab (Melanoma, prostate cancer, ovarian cancer), Farletuzumab (Ovarian cancer), FBTA05 (Chronic lymphocytic leukaemia), Ficlatuzumab (Cancer), Figitumumab (Adrenocortical carcinoma, non-small cell lung carcinoma), Flanvotumab (Melanoma), Galiximab (B-cell lymphoma), Galiximab (Non-Hodgkin-Lymphoma), Ganitumab, GC1008 (Advanced Renal Cell Carcinoma; Malignant Melanoma, Pulmonary Fibrosis), Gemtuzumab (Leukemia), Gemtuzumab ozogamicin (Acute myelogenous leukemia), Girentuximab (Clear cell renal cell carcinoma), Glembatumumab vedotin (Melanoma, breast cancer), GS6624 (Idiopathic pulmonary fibrosis and solid tumors), HuC242-DM4 (Colon Cancer, Gastric Cancer, Pancreatic Cancer), HuHMFG1 (Breast Cancer), HuN901-DM1 (Myeloma), Ibritumomab (Relapsed or refractory low-grade, follicular, or transformed B-cell non-Hodgkin's lymphoma (NHL)), Icrucumab, ID09C3 (Non-Hodgkin-Lymphoma), Indatuximab ravtansine, Inotuzumab ozogamicin, Intetumomab (Solid tumors (Prostate cancer, melanoma)), Ipilimumab (Sarcoma, Melanoma, Lung cancer, Ovarian Cancer leucemia, Lymphoma, Brain and Central Nervous System Tumors, Testicular Cancer, Prostate Cancer, Pancreatic Cancer, Breast Cancer), Iratumumab (Hodgkin's lymphoma), Labetuzumab (Colorectal cancer), Lexatumumab, Lintuzumab, Lorvotuzumab mertansine, Lucatumumab (Multiple myeloma, non-Hodgkin's lymphoma, Hodgkin's lymphoma), Lumiliximab (Chronic lymphocytic leukemia), Mapatumumab (Colon Cancer, Myeloma), Matuzumab (Lung Cancer, Cervical Cancer, Esophageal Cancer), MDX-060 (Hodgkin-Lymphoma, Lymphoma), MEDI 522 (Solid Tumors, Leukemia, Lymphoma, Small Intestine Cancer, Melanoma), Mitumomab (Small cell lung carcinoma), Mogamulizumab, MORab-003 (Ovarian Cancer, Fallopian Tube Cancer, Peritoneal Cancer), MORab-009 (Pancreatic Cancer, Mesothelioma, Ovarian Cancer, Non-Small Cell Lung Cancer, Fallopian Tube Cancer, Peritoneal Cavity Cancer), Moxetumomab pasudotox, MT103 (Non-Hodgkin-Lymphoma), Nacolomab tafenatox (Colorectal cancer), Naptumomab estafenatox (Non-small cell lung carcinoma, renal cell carcinoma), Narnatumab, Necitumumab (Non-small cell lung carcinoma), Nimotuzumab (Squamous cell carcinoma, head and neck cancer, nasopharyngeal cancer, glioma), Nimotuzumab (Squamous cell carcinomas, Glioma, Solid Tumors, Lung Cancer), Olaratumab, Onartuzumab (Cancer), Oportuzumab monatox, Oregovomab (Ovarian cancer), Oregovomab (Ovarian Cancer, Fallopian Tube Cancer, Peritoneal Cavity Cancer), PAM4 (Pancreatic Cancer), Panitumumab (Colon Cancer, Lung Cancer, Breast Cancer; Bladder Cancer; Ovarian Cancer), Patritumab, Pemtumomab, Pertuzumab (Breast Cancer, Ovarian Cancer, Lung Cancer, Prostate Cancer), Pritumumab (Brain cancer), Racotumomab, Radretumab, Ramucirumab (Solid tumors), Rilotumumab (Solid tumors), Rituximab (Urticaria, Rheumatoid Arthritis, Ulcerative Colitis, Chronic Focal Encephalitis, Non-Hodgkin-Lymphoma, Lymphoma, Chronic Lymphocytic Leukemia), Robatumumab, Samalizumab, SGN-30 (Hodgkin-Lymphoma, Lymphoma), SGN-40 (Non-Hodgkin-Lymphoma, Myeloma, Leukemia, Chronic Lymphocytic Leukemia), Sibrotuzumab, Siltuximab, Tabalumab (B-cell cancers), Tacatuzumab tetraxetan, Taplitumomab paptox, Tenatumomab, Teprotumumab (Hematologic tumors), TGN1412 (Chronic lymphocytic leukemia, rheumatoid arthritis), Ticilimumab (=tremelimumab), Tigatuzumab, TNX-650 (Hodgkin's lymphoma), Tositumomab (Follicular lymphoma, B cell lymphomas, Leukemias, Myeloma), Trastuzumab (Breast Cancer, Endometrial Cancer, Solid Tumors), TRBS07 (Melanoma), Tremelimumab, TRU-016 (Chronic lymphocytic leukemia), TRU-016 (Non-Hodgkin lymphoma), Tucotuzumab celmoleukin, Ublituximab, Urelumab, Veltuzumab (Non-Hodgkin's lymphoma), Veltuzumab (IMMU-106) (Non-Hodgkin's lymphoma), Volociximab (Renal Cell Carcinoma, Pancreatic Cancer, Melanoma), Votumumab (Colorectal tumors), WX-G250 (Renal Cell Carcinoma), Zalutumumab (Head and Neck Cancer, Squamous Cell Cancer), and Zanolimumab (T-Cell-Lymphoma);

antibodies, which are used inter alia for the treatment of immune disorders, e.g. Efalizumab (Psoriasis), Epratuzumab (Autoimmune diseases, Systemic Lupus Erythematosus, Non-Hodgkin-Lymphoma, Leukemia), Etrolizumab (inflammatory bowel disease), Fontolizumab (Crohn's disease), Ixekizumab (autoimmune diseases), Mepolizumab (Hypereosinophilie-Syndrom, Asthma, Eosinophilic Gastroenteritis, Churg-Strauss Syndrome, Eosinophilic Esophagitis), Milatuzumab (multiple myeloma and other hematological malignancies), Pooled immunoglobulins (Primary immunodeficiencies), Priliximab (Crohn's disease, multiple sclerosis), Rituximab (Urticaria, Rheumatoid Arthritis, Ulcerative Colitis, Chronic Focal Encephalitis, Non-Hodgkin-Lymphoma, Lymphoma, Chronic Lymphocytic Leukemia), Rontalizumab (systemic lupus erythematosus), Ruplizumab (rheumatic diseases), Sarilumab (rheumatoid arthritis, ankylosing spondylitis), Vedolizumab (Crohn's disease, ulcerative colitis), Visilizumab (Crohn's disease, ulcerative colitis), Reslizumab (inflammations of the airways, skin and gastrointestinal tract), Adalimumab (Rheumatoid arthritis, Crohn's disease, Ankylosing spondylitis, Psoriatic arthritis), Aselizumab (severely injured patients), Atinumab (treatment of neurologic systems), Atlizumab (rheumatoid arthritis, systemic juvenile idiopathic arthritis), Bertilimumab (severe allergic disorders), Besilesomab (inflammatory lesions and metastases), BMS-945429, ALD518 (cancer and rheumatoid arthritis), Briakinumab (psoriasis, rheumatoid arthritis, inflammatory bowel diseases, multiple sclerosis), Brodalumab (inflammatory diseases), Canakinumab (rheumatoid arthritis), Canakinumab (cryopyrin-associated periodic syndromes (CAPS), rheumatoid arthritis, chronic obstructive pulmonary disease), Certolizumab pegol (Crohn's disease), Erlizumab (heart attack, stroke, traumatic shock), Fezakinumab (rheumatoid arthritis, psoriasis), Golimumab (rheumatoid arthritis, psoriatic arthritis, ankylosing spondylitis), Gomiliximab (allergic asthma), Infliximab (Rheumatoid arthritis, Crohn's disease, ankylosing spondylitis, psoriatic arthritis, plaque psoriasis, Morbus Bechterew, Colitis ulcerosa), Mavrilimumab (rheumatoid arthritis), Natalizumab (Multiple sclerosis), Ocrelizumab (multiple sclerosis, rheumatoid arthritis, lupus erythematosus, hematological cancer), Odulimomab (prevention of organ transplant rejections, immunological diseases), Ofatumumab (Chronic lymphocytic leukemia, follicular non-Hodgkin's lymphoma, B cell lymphoma, rheumatoid arthritis, relapsing remitting multiple sclerosis, Lymphoma, B-Cell Chronic Lymphocytic Leukemia), Ozoralizumab (inflammation), Pexelizumab (reduction of side effects of cardiac surgery), Rovelizumab (haemorrhagic shock), SBI-087 (Rheumatoid arthritis), SBI-087 (Systemic lupus erythematosus), Secukinumab (uveitis, rheumatoid arthritis psoriasis), Sirukumab (rheumatoid arthritis), Talizumab (allergic reaction), Tocilizumab (rheumatoid arthritis, systemic juvenile idiopathic arthritis, Castleman's disease), Toralizumab (rheumatoid arthritis, lupus nephritis), TRU-015 (Rheumatoid arthritis), TRU-016 (Autoimmune disease and inflammation), Ustekinumab (multiple sclerosis, psoriasis, psoriatic arthritis), Ustekinumab (IL-12/IL-23 blocker) (Plaque-Psoriasis, psoriatic arthritis, multiple sclerosis, sarcoidosis, the latter versus), Vepalimomab (inflammation), Zolimomab aritox (systemic lupus erythematosus, graft-versus-host disease), Sifalimumab (SLE, dermatomyositis, polymyositis), Lumiliximab (Allergies), and Rho(D) Immune Globulin (Rhesus disease); or are selected from antibodies used for the treatment of infectious diseases, e.g. Afelimomab (sepsis), CR6261 (infectious disease/influenza A), Edobacomab (sepsis caused by gram-negative bacteria), Efungumab (invasive *Candida* infection), Exbivirumab (hepatitis B), Felvizumab (respiratory syncytial virus infection), Foravirumab (rabies (prophylaxis)), Ibalizumab (HIV infection), Libivirumab (hepatitis B), Motavizumab (respiratory syncytial virus (prevention)), Nebacumab (sepsis), Tuvirumab (chronic hepatitis B), Urtoxazumab (diarrhoea caused by *E. coli*), Bavituximab (diverse viral infections), Pagibaximab (sepsis (e.g. *Staphylococcus*)), Palivizumab (prevention of respiratory syncytial virus infection in high-risk paediatric patients), Panobacumab (*Pseudomonas aeruginosa* infection), PRO 140 (HIV infection), Rafivirumab (rabies (prophylaxis)), Raxibacumab (anthrax (prophylaxis and treatment)), Regavirumab (cytomegalovirus infection), Sevirumab (cytomegalovirus infection), Suvizumab (viral infections), and Tefibazumab (*Staphylococcus aureus* infection);

antibodies, which are used inter alia for the treatment of blood disorders, e.g. Abciximab (percutaneous coronary intervention), Atorolimumab (hemolytic disease of the newborn), Eculizumab (Paroxysmal nocturnal haemoglobinuria), Mepolizumab (Hypereosinophilie-Syndrom, Asthma, Eosinophilic Gastroenteritis, Churg-Strauss Syndrome, Eosinophilic Esophagitis), and Milatuzumab (multiple myeloma and other hematological malignancies);

antibodies, which are used inter alia for immunoregulation, e.g. Antithymocyte globulin (Acute kidney transplant rejection, aplastic anaemia), Basiliximab (Prophylaxis against allograft rejection in renal transplant patients receiving an immunosuppressive regimen including cyclosporine and corticosteroids), Cedelizumab (prevention of organ transplant rejections, treatment of autoimmune diseases), Daclizumab (Prophylaxis against acute allograft rejection in patients receiving renal transplants, Multiple Sclerosis), Gavilimomab (graft versus host disease), Inolimomab (graft versus host disease), Muromonab-CD3 (prevention of organ transplant rejections), Muromonab-CD3 (Acute renal allograft rejection or steroid-resistant cardiac or hepatic allograft rejection), Odulimomab (prevention of organ transplant rejections, immunological diseases), and Siplizumab (psoriasis, graft-versus-host disease (prevention));

antibodies used for the treatment of diabetes, e.g. Gevokizumab (diabetes), Otelixizumab (diabetes mellitus type 1), and Teplizumab (diabetes mellitus type 1);

antibodies, which are used for the treatment of the Alzheimer's disease, e.g. Bapineuzumab, Crenezumab, Gantenerumab, Ponezumab, R1450, and Solanezumab;

antibodies, which are used for the treatment of asthma, e.g. Benralizumab, Enokizumab, Keliximab, Lebrikizumab, Omalizumab, Oxelumab, Pascolizumab, and Tralokinumab; and antibodies, which are used for the treatment of diverse disorders, e.g. Blosozumab (osteoporosis), CaroRx (Tooth decay), Fresolimumab (idiopathic pulmonary fibrosis, focal segmental glomerulosclerosis, cancer), Fulranumab (pain), Romosozumab (osteoporosis), Stamulumab (muscular dystrophy), Tanezumab (pain), and Ranibizumab (Neovascular age-related macular degeneration).

The coding region of the modified RNA according to the present invention may occur as a mono-, di-, or even multicistronic RNA, i.e. an RNA, which carries the coding sequences of one, two or more proteins or peptides. Such coding sequences in di-, or even multicistronic RNA's may be separated by at least one internal ribosome entry site (IRES) sequence, e.g. as described herein or by signal peptides which induce the cleavage of the resulting polypeptide, which comprises several proteins or peptides.

Pharmaceutical Composition:

Additionally, according to another aspect, the present invention also relates to the use of the modified RNA as defined herein or of a composition comprising a plurality of modifed RNA molecules as defined herein for the preparation of a pharmaceutical composition for increasing the expression of an encoded peptide or protein, particularly for use in gene therapy or genetic vaccination, e.g. for treating a disease, preferably as defined herein, e.g. applying or administering the modifed RNA as defined herein or of a composition comprising a plurality of modified RNA molecules as defined herein to a cell (e.g. an expression host cell or a somatic cell), a tissue or an organism, preferably in naked form or complexed form or as a pharmaceutical composition as described herein by jet injection.

Accordingly, in a particular preferred aspect, the present invention also provides a pharmaceutical composition, comprising a modified RNA as defined herein or a composition comprising a plurality of modified RNA's as defined herein and optionally a pharmaceutically acceptable carrier and/or vehicle for administration by jet injection.

As a first ingredient, the pharmaceutical composition comprises at least one modified nucleic acid as defined herein.

As a second ingredient the pharmaceutical composition may optionally comprise at least one additional pharmaceutically active component. A pharmaceutically active component in this connection is a compound that has a therapeutic effect to heal, ameliorate or prevent a particular indication or disease as mentioned herein. Such compounds include, without implying any limitation, peptides or proteins, preferably as defined herein, nucleic acids, preferably as defined herein, (therapeutically active) low molecular weight organic or inorganic compounds (molecular weight less than 5000, preferably less than 1000), sugars, antigens or antibodies, preferably as defined herein, therapeutic agents already known in the prior art, antigenic cells, antigenic cellular fragments, cellular fractions; cell wall components (e.g. polysaccharides), modified, attenuated or de-activated (e.g. chemically or by irradiation) pathogens (virus, bacteria etc.), adjuvants, preferably as defined herein, etc.

Furthermore, the pharmaceutical composition may comprise a pharmaceutically acceptable carrier and/or vehicle. In the context of the present invention, a pharmaceutically acceptable carrier typically includes the liquid or non-liquid basis of the inventive pharmaceutical composition. The carrier will typically be pyrogen-free water, isotonic saline or buffered (aqueous) solutions, e.g. phosphate, citrate etc. buffered solutions. The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the pharmaceutical composition, which are suitable for administration to a patient to be treated. The term "compatible" as used here means that these constituents of the pharmaceutical composition are capable of being mixed with the modified RNA as defined herein in such a manner that no interaction occurs which would substantially reduce the pharmaceutical effectiveness of the pharmaceutical composition under typical use conditions.

Complexation:

Furthermore, the pharmaceutical composition may comprise a carrier for the modified RNA. Such a carrier may be suitable for mediating dissolution in physiological acceptable liquids, transport and cellular uptake of the pharmaceutically active modified RNA molecule. Accordingly, such a carrier may be a component, which may be suitable for depot and delivery of a modified RNA according to the invention. Such components may be, for example, cationic or polycationic carriers or compounds, which may serve as transfection or complexation agent.

Particularly preferred transfection or complexation agents in this context are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones.

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (III):

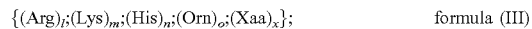
$\{(Arg)_l;(Lys)_m;(His)_n;(Orn)_o;(Xaa)_x\};$  formula (III)

wherein l+m+n+o+x=3-100, and 1, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Ornm and Xaa may be positioned at any place of the peptide. In this context cationic peptides or proteins in the range of 7-30 amino acids are particular preferred.

Further, the cationic or polycationic peptide or protein, when defined according to formula $\{(Arg)_l; (Lys)_m;(His)_n; (Orn)_o;(Xaa)_x\}$ (formula (III)) as shown above and which comprise or are additionally modified to comprise at least one —SH moeity, may be, without being restricted thereto, selected from subformula (Ia):

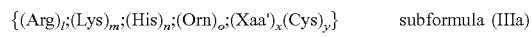
$\{(Arg)_l;(Lys)_m;(His)_n;(Orn)_o;(Xaa')_x(Cys)_y\}$  subformula (IIIa)

wherein $(Arg)_l;(Lys)_m;(His)_n;(Orn)_o;$ and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (IIIb):

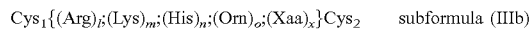
$Cys_1\{(Arg)_l;(Lys)_m;(His)_n;(Orn)_o;(Xaa)_x\}Cys_2$  subformula (IIIb)

wherein empirical formula $\{(Arg)_l;(Lys)_m;(His)_n;(Orn)_o;(Xaa)_x\}$ (formula (IV)) is as defined herein and forms a core of an amino acid sequence according to (semiempirical) formula (IV) and wherein $Cys_1$ and $Cys_2$ are Cysteines proximal to, or terminal to $(Arg)_l;(Lys)_m;(His)_n;(Orn)_o;(Xaa)_x$.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecyl-amidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl] trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g. polyethyleneglycole); etc.

In this context, it is particularly preferred that the modified RNA molecule is complexed at least partially with a cationic or polycationic compound, preferably cationic proteins or peptides. Partially means that only a part of the modified RNA molecule is complexed with a cationic or polycationic compound and that the rest of the modified RNA molecule is in uncomplexed form ("free"). Preferably the ratio of complexed modified RNA to free modified RNA is selected from a range of about 5:1 (w/w) to about 1:10 (w/w), more preferably from a range of about 4:1 (w/w) to about 1:8 (w/w), even more preferably from a range of about 3:1 (w/w) to about 1:5 (w/w) or 1:3 (w/w), and most preferably the ratio of complexed nucleic acid to free nucleic acid is selected from a ratio of about 1:1 (w/w).

According to a specific embodiment, the pharmaceutical composition may comprise an adjuvant. In this context, an adjuvant may be understood as any compound, which is suitable to initiate or increase an immune response of the innate immune system, i.e. a non-specific immune response. With other words, when administered, the inventive pharmaceutical composition preferably elicits an innate immune response due to the adjuvant, optionally contained therein. Preferably, such an adjuvant may be selected from an adjuvant known to a skilled person and suitable for the present case, i.e. supporting the induction of an innate immune response in a mammal, e.g. an adjuvant protein as defined above or an adjuvant as defined in the following.

Particularly preferred as adjuvants suitable for depot and delivery are cationic or polycationic compounds as defined above for the modified RNA as vehicle, transfection or complexation agent.

Further additives which may be included in the inventive pharmaceutical composition are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The pharmaceutical composition can also additionally contain any further compound, which is known to be immunostimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

The pharmaceutical composition may preferably be administered subcutaneously, intramuscularly or intradermally by jet injection. Sterile injectable forms of the pharmaceutical compositions may be aqueous or oleaginous suspension. These suspensions may be formulated according to techniques known in the art using suitable dispersing or wetting agents and suspending agents.

The pharmaceutical composition typically comprises a "safe and effective amount" of the components of the pharmaceutical composition, particularly of the modified RNA as defined herein. As used herein, a "safe and effective amount" means an amount of the modified RNA as defined herein as such that is sufficient to significantly induce a positive modification of a disease or disorder as defined herein. At the same time, however, a "safe and effective amount" is small enough to avoid serious side-effects and to permit a sensible relationship between advantage and risk. The determination of these limits typically lies within the scope of sensible medical judgment.

The present invention furthermore provides several applications and uses of the modified RNA as defined herein, of the composition comprising a plurality of modified RNA molecules as defined herein, of the pharmaceutical composition, comprising the modified RNA as defined herein or of kits comprising same.

According to one specific aspect, the present invention is directed to the first medical use of the inventive modified RNA as defined herein or of the inventive composition comprising a plurality of inventive RNA molecules as defined herein as a medicament, particularly in gene therapy or genetic vaccination, preferably for the treatment of diseases as defined herein.

According to another aspect, the present invention is directed to the second medical use of the inventive modified RNA as defined herein or of the inventive composition comprising a plurality of inventive modified RNA molecules as defined herein, for the treatment of diseases as defined herein, preferably to the use of the inventive modified RNA as defined herein, of the inventive composition comprising a plurality of inventive modified RNA molecules as defined herein, of a pharmaceutical composition comprising same or of kits comprising same for the preparation of a medicament for the prophylaxis, treatment and/or amelioration of diseases as defined herein. Preferably, the pharmaceutical composition is used or to be administered to a patient in need thereof for this purpose.

Preferably, diseases as mentioned herein are preferably selected from infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system.

Diseases:

Infectious Diseases:

Preferably, infectious diseases as mentioned herein are preferably selected from viral, bacterial, protozoological and prion infectious diseases. Such infectious diseases are typically selected from the list consisting of *Acinetobacter* infections, African sleeping sickness (African trypanosomiasis), AIDS (Acquired immunodeficiency syndrome), Amoebiasis, Anaplasmosis, Anthrax, Appendicitis, *Arcanobacterium haemolyticum* infections, Argentine hemorrhagic fever, Ascariasis, Aspergillosis, Astrovirus infections, Athlete's foot, Babesiosis, *Bacillus cereus* infections, Bacterial meningitis, Bacterial pneumonia, Bacterial vaginosis (BV), *Bacteroides* infections, Balantidiasis, *Baylisascaris* infections, Bilharziosis, BK virus infections, Black *piedra*, *Blastocystis hominis* infections, Blastomycosis, Bolivian hemorrhagic fever, *Borrelia* infectionss (Borreliosis), Botulism (and Infant botulism), Bovine tapeworm, Brazilian hemorrhagic fever, Brucellosis, *Burkholderia* infections, Buruli ulcer, Calicivirus infections (Norovirus and Sapovirus), Campylobacteriosis, Candidiasis (Candidosis), Canine tapeworm infections, Cat-scratch disease, Chagas Disease (American trypanosomiasis), Chancroid, Chickenpox, *Chlamydia* infections, *Chlamydia trachomatis* infections, *Chlamydophila pneumoniae* infections, Cholera, Chromoblastomycosis, Climatic bubo, Clonorchiasis, *Clostridium difficile* infections, Coccidioidomycosis, Cold, Colorado tick fever (CTF), Common cold (Acute viral rhinopharyngitis; Acute coryza), Condyloma *acuminata*, Conjunctivitis, Creutzfeldt-Jakob disease (CJD), Crimean-Congo hemorrhagic fever (CCHF), Cryptococcosis, Cryptosporidiosis, Cutaneous larva migrans (CLM), Cutaneous Leishmaniosis, Cyclosporiasis, Cysticercosis, Cytomegalovirus infections, *Dengue* fever, Dermatophytosis, Dientamoebiasis, Diphtheria, Diphyllobothriasis, Donavanosis, Dracunculiasis, Early summer meningoencephalitis (FSME), Ebola hemorrhagic fever, Echinococcosis, Ehrlichiosis, Enterobiasis (Pinworm infections), *Enterococcus* infections, *Enterovirus* infections, Epidemic typhus, Epiglottitis, Epstein-Barr Virus Infectious Mononucleosis, Erythema infectiosum (Fifth disease), Exanthem subitum, Fasciolopsiasis, Fasciolosis, Fatal familial insomnia (FFI), Fifth disease, Filariasis, Fish poisoning (Ciguatera), Fish tapeworm, Flu, Food poisoning by *Clostridium perfringens*, Fox tapeworm, Free-living amebic infections, *Fusobacterium* infections, Gas gangrene, Geotrichosis, Gerstmann-Straussler-Scheinker syndrome (GSS), Giardiasis, Glanders, Gnathostomiasis, Gonorrhea, Granuloma inguinale (Donovanosis), Group A streptococcal infections, Group B streptococcal infections, *Haemophilus influenzae* infections, Hand foot and mouth disease (HFMD), Hantavirus Pulmonary Syndrome (HPS), *Helicobacter pylori* infections, Hemolytic-uremic syndrome (HUS), Hemorrhagic fever with renal syndrome (HFRS), Henipavirus infections, Hepatitis A, Hepatitis B, Hepatitis C, Hepatitis D, Hepatitis E, Herpes simplex, Herpes simplex type I, Herpes simplex type II, Herpes zoster, Histoplasmosis, Hollow warts, Hookworm infections, Human bocavirus infections, Human *ewingii* ehrlichiosis, Human granulocytic anaplasmosis (HGA), Human metapneumovirus infections, Human monocytic ehrlichiosis, Human papillomavirus (HPV) infections, Human parainfluenza virus infections, Hymenolepiasis, Influenza, Isosporiasis, Japanese encephalitis, Kawasaki disease, Keratitis, Kingella kingae infections, Kuru, Lambliasis (Giardiasis), Lassa fever, Legionellosis (Legionnaires' disease, Pontiac fever), Leishmaniasis, Leprosy, Leptospirosis, Lice, Listeriosis, Lyme borreliosis, Lyme disease, Lymphatic filariasis (Elephantiasis), Lymphocytic choriomeningitis, Malaria, Marburg hemorrhagic fever (MHF), Marburg virus, Measles, Melioidosis (Whitmore's disease), Meningitis, Meningococcal disease, Metagonimiasis, Microsporidiosis, Miniature tapeworm, Miscarriage (prostate inflammation), Molluscum contagiosum (MC), Mononucleosis, Mumps, Murine typhus (Endemic typhus), Mycetoma, *Mycoplasma hominis, Mycoplasma* pneumonia, Myiasis, Nappy/diaper dermatitis, Neonatal conjunctivitis (Ophthalmia neonatorum), Neonatal sepsis (Chorioamnionitis), Nocardiosis, Noma, Norwalk virus infections, Onchocerciasis (River blindness), Osteomyelitis, Otitis media, Paracoccidioidomycosis (South American blastomycosis), Paragonimiasis, Paratyphus, Pasteurellosis, Pediculosis capitis (Head lice), Pediculosis corporis (Body lice), Pediculosis pubis (Pubic lice, Crab lice), Pelvic inflammatory disease (PID), Pertussis (Whooping cough), Pfeiffer's glandular fever, Plague, Pneumococcal infections, *Pneumocystis* pneumonia (PCP), Pneumonia, Polio (childhood lameness), Poliomyelitis, Porcine tapeworm, *Prevotella* infections, Primary amoebic meningoencephalitis (PAM), Progressive multifocal leukoencephalopathy, Pseudo-croup, Psittacosis, Q fever, Rabbit fever, Rabies, Rat-bite fever, Reiter's syndrome, Respiratory syncytial virus infections (RSV), Rhinosporidiosis, Rhinovirus infections, Rickettsial infections, Rickettsialpox, Rift Valley fever (RVF), Rocky mountain spotted fever (RMSF), Rotavirus infections, Rubella, *Salmonella* paratyphus, *Salmonella* typhus, *Salmonellosis*, SARS (Severe Acute Respiratory Syndrome), Scabies, Scarlet fever, Schistosomiasis (Bilharziosis), Scrub typhus, Sepsis, Shigellosis (Bacillary dysentery), Shingles, Smallpox (Variola), Soft chancre, Sporotrichosis, Staphylococcal food poisoning, Staphylococcal infections, Strongyloidiasis, Syphilis, Taeniasis, Tetanus, Three-day fever, Tick-borne encephalitis, Tinea barbae (Barber's itch), Tinea capitis (Ringworm of the Scalp), Tinea corporis (Ringworm of the Body), Tinea cruris (Jock itch), Tinea manuum (Ringworm of the Hand), Tinea nigra, Tinea pedis (Athlete's foot), Tinea unguium (Onychomycosis), Tinea *versicolor* (*Pityriasis versicolor*), Toxocariasis (Ocular Larva Migrans (OLM) and Visceral Larva Migrans (VLM)), Toxoplasmosis, Trichinellosis, Trichomoniasis, Trichuriasis (Whipworm infections), Tripper, Trypanosomiasis (sleeping sickness), Tsutsugamushi disease, Tuberculosis, Tularemia, Typhus, Typhus fever, *Ureaplasma urealyticum* infections, Vaginitis (Colpitis), Variant Creutzfeldt-Jakob disease (vCJD, nvCJD), Venezuelan equine encephalitis, Venezuelan hemorrhagic fever, Viral pneumonia, Visceral Leishmaniosis, Warts, West Nile Fever, Western equine encephalitis, White *piedra* (Tinea blanca), Whooping cough, Yeast fungus spots, Yellow fever, *Yersinia pseudotuberculosis* infections, Yersiniosis, and Zygomycosis.

Cancer Diseases:

Preferably, diseases as mentioned herein are selected from cancer or tumour diseases which preferably include e.g. Acute lymphoblastic leukemia, Acute myeloid leukemia, Adrenocortical carcinoma, AIDS-related cancers, AIDS-related lymphoma, Anal cancer, Appendix cancer, Astrocytoma, Basal cell carcinoma, Bile duct cancer, Bladder cancer, Bone cancer, Osteosarcoma/Malignant fibrous histiocytoma, Brainstem glioma, Brain tumor, cerebellar astrocytoma, cerebral astrocytoma/malignant glioma, ependymoma, medulloblastoma, supratentorial primitive neuroectodermal tumors, visual pathway and hypothalamic glioma, Breast cancer, Bronchial adenomas/carcinoids, Burkitt lymphoma, childhood Carcinoid tumor, gastrointestinal Carcinoid tumor, Carcinoma of unknown primary, primary Central nervous system lymphoma, childhood Cerebellar astrocytoma, childhood Cerebral astrocytoma/Malignant glioma, Cervical cancer, Childhood cancers, Chronic lymphocytic leukemia, Chronic myelogenous leukemia, Chronic myeloproliferative disorders, Colon Cancer, Cutaneous T-cell lymphoma, Desmoplastic small round cell tumor, Endometrial cancer, Ependymoma, Esophageal cancer, Ewing's sarcoma in the Ewing family of tumors, Childhood Extracranial germ cell tumor, Extragonadal Germ cell tumor, Extrahepatic bile duct cancer, Intraocular melanoma, Retinoblastoma, Gallbladder cancer, Gastric (Stomach) cancer, Gastrointestinal Carcinoid Tumor, Gastrointestinal stromal tumor (GIST), extracranial, extragonadal, or ovarian Germ cell tumor, Gestational trophoblastic tumor, Glioma of the brain stem, Childhood Cerebral Astrocytoma, Childhood Visual Pathway and Hypothalamic Glioma, Gastric carcinoid, Hairy cell leukemia, Head and neck cancer, Heart cancer, Hepatocellular (liver) cancer, Hodgkin lymphoma, Hypopharyngeal cancer, childhood Hypothalamic and visual pathway glioma, Intraocular Melanoma, Islet Cell Carcinoma (Endocrine Pancreas), Kaposi sarcoma, Kidney cancer (renal cell cancer), Laryngeal Cancer, Leukemias, acute lymphoblastic Leukemia, acute myeloid Leukemia, chronic lymphocytic Leukemia, chronic myelogenous Leukemia, hairy cell Leukemia, Lip and Oral Cavity Cancer, Liposarcoma, Liver Cancer, Non-Small Cell Lung Cancer, Small Cell Lung Cancer, Lymphomas, AIDS-related Lymphoma, Burkitt Lymphoma, cutaneous T-Cell Lymphoma, Hodgkin Lymphoma, Non-Hodgkin Lymphomas, Primary Central Nervous System Lymphoma, Waldenström Macroglobulinemia, Malignant Fibrous Histiocytoma of Bone/Osteosarcoma, Childhood Medulloblastoma, Melanoma, Intraocular (Eye) Melanoma, Merkel Cell Carcinoma, Adult Malignant Mesothelioma, Childhood Mesothelioma, Metastatic Squamous Neck Cancer with Occult Primary, Mouth Cancer, Childhood Multiple Endocrine Neoplasia Syndrome, Multiple Myeloma/Plasma Cell Neoplasm, Mycosis Fungoides, Myelodysplastic Syndromes, Myelodysplastic/Myeloproliferative Diseases, Chronic Myelogenous Leukemia, Adult Acute Myeloid Leukemia, Childhood Acute Myeloid Leukemia, Multiple Myeloma (Cancer of the Bone-Marrow), Chronic Myeloproliferative Disorders, Nasal cavity and paranasal sinus cancer, Nasopharyngeal carcinoma, Neuroblastoma, Oral Cancer, Oropharyngeal cancer, Osteosarcoma/malignant fibrous histiocytoma of bone, Ovarian cancer, Ovarian epithelial cancer (Surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, childhood Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Cancer of the Renal pelvis and ureter, Retinoblastoma, childhood Rhabdomyosarcoma, Salivary gland cancer, Sarcoma of the Ewing family of tumors, Kaposi Sarcoma, soft tissue Sarcoma, uterine Sarcoma, Sdzary syndrome, Skin cancer (nonmelanoma), Skin cancer (melanoma), Merkel cell Skin carcinoma, Small intestine cancer, Squamous cell carcinoma, metastatic Squamous neck cancer with occult primary, childhood Supratentorial primitive neuroectodermal tumor, Testicular cancer, Throat cancer, childhood Thymoma, Thymoma and Thymic carcinoma, Thyroid cancer, childhood Thyroid cancer, Transitional cell cancer of the renal pelvis and ureter, gestational Trophoblastic tumor, Urethral cancer, endometrial Uterine cancer, Uterine sarcoma, Vaginal cancer, childhood Visual pathway and hypothalamic glioma, Vulvar cancer, Waldenstrim macroglobulinemia, and childhood Wilms tumor (kidney cancer).

Allergies:

Preferably, diseases as mentioned herein are selected from allergies which preferably include e.g. pollen allergy (allergy against grass pollen, tree pollen (e.g. pollen of hazel, birch, alder, ash), flower pollen, herb pollen (e.g. pollen of mugwort)), dust mite allergy, mold allergy (e.g. allergy against *Acremonium, Aspergillus, Cladosporium, Fusarium, Mucor, Penicillium, Rhizopus, Stachybotrys, Trichoderma,* or *Alternaria*), pet allergy (allergy against animals; e.g against cats, dogs, horses), food allergy (e.g. allergy against fish (e.g. bass, cod, flounder), seafood (e.g. crab, lobster, shrimps), egg, wheat, nuts (e.g. peanuts, almonds, cashews, walnuts), soya, milk, etc.) or insect bite allergy (allergy against insect venom, e.g. venom of wasps, bees, hornets, ants, mosquitos, or ticks).

In a particularly preferred embodiment, an RNA comprising at least one modification and comprising at least one open reading frame is used in treatment of prostate cancer.

Autoimmune Diseases:

According to another specific embodiment, diseases as defined herein comprise autoimmune diseases as defined in the following. autoimmune diseases are preferably selected from Addison disease (autoimmune adrenalitis, Morbus Addison), alopecia areata, Addison's anemia (Morbus Biermer), autoimmune hemolytic anemia (AIHA), autoimmune hemolytic anemia (AIHA) of the cold type (cold hemagglutinine disease, cold autoimmune hemolytic anemia (AIHA) (cold agglutinin disease), (CHAD)), autoimmune hemolytic anemia (AIHA) of the warm type (warm AIHA, warm autoimmune haemolytic anemia (AIHA)), autoimmune hemolytic Donath-Landsteiner anemia (paroxysmal cold hemoglobinuria), antiphospholipid syndrome (APS), atherosclerosis, autoimmune arthritis, arteriitis temporalis, Takayasu arteriitis (Takayasu's disease, aortic arch disease), temporal arteriitis/giant cell arteriitis, autoimmune chronic gastritis, autoimmune infertility, autoimmune inner ear disease (AIED), Basedow's disease (Morbus Basedow), Bechterew's disease (Morbus Bechterew, ankylosing spondylitis, spondylitis ankylosans), Behcet's syndrome (Morbus Behcet), bowel disease including autoimmune inflammatory bowel disease (including colitis ulcerosa (Morbus Crohn, Crohn's disease), cardiomyopathy, particularly autoimmune cardiomyopathy, idiopathic dilated cardiomyopathy (DCM), celiac sprue dermatitis (gluten mediated enteropathia), chronic fatigue immune dysfunction syndrome (CFIDS), chronic inflammatory demyelinating polyneuropathy (CIDP), chronic polyarthritis, Churg-Strauss syndrome, cicatricial pemphigoid, Cogan syndrome, CREST syndrome (syndrom with Calcinosis cutis, Raynaud phenomenon, motility disorders of the esophagus, sklerodaktylia and teleangiectasia), Crohn's disease (Morbus Crohn, colitis ulcerosa), dermatitis herpetiformis during, dermatologic autoimmune diseases, dermatomyositis, Diabetes, Diabetes mellitus Type 1 (type I diabetes, insuline dependent Diabetes mellitus), Diabetes mellitus Type 2 (type II diabetes), essential mixed cryoglobulinemia, essential mixed cryoglobulinemia, fibromyalgia, fibromyositis, Goodpasture syndrome (anti-GBM mediated glomerulonephritis), graft versus host disease, Guillain-Barr6 syndrome (GBM, Polyradikuloneuritis), haematologic autoimmune diseases, Hashimoto thyroiditis, hemophilia, acquired hemophilia, hepatitis, autoimmune hepatitis, particularly autoimmune forms of chronic hepatitis, idiopathic pulmonary fibrosis (IPF), idiopathic thrombocytopenic purpura, Immuno-thrombocytopenic purpura (Morbus Werlhof; ITP), IgA nephropathy, infertility, autoimmune infertility, juvenile rheumatoid arthritis (Morbus Still, Still syndrome), Lambert-Eaton syndrome, lichen planus, lichen sclerosus, lupus erythematosus, systemic lupus erythematosus (SLE), lupus erythematosus (discoid form), Lyme arthritis (Lyme disease, *borrelia* arthritis), Méniere's disease (Morbus Ménierb); mixed connective tissue disease (MCTD), multiple sclerosis (MS, encephalomyelitis disseminate, Charcot's disease), Myasthenia gravis (myasthenia, MG), myosits, polymyositis, neural autoimmune diseases, neurodermitis, pemphigus vulgaris, bullous pemphigoid, scar forming pemphigoid; polyarteriitis *nodosa* (periarteiitis *nodosa*), polychondritis (panchondritis), polyglandular (autoimmune) syndrome (PGA syndrome, Schmidt's syndrome), Polymyalgia rheumatica, primary agammaglobulinemia, primary biliary cirrhosis PBC, primary autoimmune cholangitis), progressive systemic sclerosis (PSS), Psoriasis, Psoriasis vulgaris, Raynaud's phenomena, Reiter's syndrome (Morbus Reiter, urethral conjunctive synovial syndrome)), rheumatoid arthritis (RA, chronic polyarthritis, rheumatic disease of the joints, rheumatic fever), sarcoidosis (Morbus Boeck, Besnier-Boeck-Schaumann disease), stiff-man syndrome, Sclerodermia, Scleroderma, Sjögren's syndrome, sympathetic ophtalmia; Transient gluten intolerance, transplanted organ rejection, uveitis, autoimmune uveitis, Vasculitis, Vitiligo, (leucoderma, piebold skin), and Wegner's disease (Morbus Wegner, Wegner's granulomatosis) In this context particularly preferred are inherited diseases selected from: 1p36 deletion syndrome; 18p deletion syndrome; 21-hydroxylase deficiency; 45,X (Turner syndrome); 47,XX,+21 (Down syndrome); 47,XXX (triple X syndrome); 47,XXY (Klinefelter syndrome); 47,XY,+21 (Down syndrome); 47,XYY syndrome; 5-ALA dehydratase-deficient *porphyria* (ALA dehydratase deficiency); 5-aminolaevulinic dehydratase deficiency *porphyria* (ALA dehydratase deficiency); 5p deletion syndrome (Cri du chat) 5p-syndrome (Cri du chat); A-T (ataxia-telangiectasia); AAT (alpha-1 antitrypsin deficiency); Absence of vas deferens (congenital bilateral absence of vas deferens); Absent vasa (congenital bilateral absence of vas deferens); aceruloplasminemia; ACG2 (achondrogenesis type II); ACH (achondroplasia); Achondrogenesis type II; achondroplasia; Acid beta-glucosidase deficiency (Gaucher disease type 1); Acrocephalosyndactyly (Apert) (Apert syndrome); acrocephalosyndactyly, type V (Pfeiffer syndrome); Acrocephaly (Apert syndrome); Acute cerebral Gaucher's disease (Gaucher disease type 2); acute intermittent *porphyria*; ACY2 deficiency (Canavan disease); AD (Alzheimer's disease); Adelaide-type craniosynostosis (Muenke syndrome); Adenomatous Polyposis *Coli* (familial adenomatous polyposis); Adenomatous Polyposis of the Colon (familial adenomatous polyposis); ADP (ALA dehydratase deficiency); adenylosuccinate lyase deficiency; Adrenal gland disorders (21-hydroxylase deficiency); Adrenogenital syndrome (21-hydroxylase deficiency); Adrenoleukodystrophy; AIP (acute intermittent *porphyria*); AIS (androgen insensitivity syndrome); AKU (alkaptonuria); ALA dehydratase *porphyria* (ALA dehydratase deficiency); ALA-D *porphyria* (ALA dehydratase deficiency); ALA dehydratase deficiency; Alcaptonuria (alkaptonuria); Alexander disease; alkaptonuria; Alkaptonuric ochronosis (alkaptonuria); alpha-1 antitrypsin deficiency; alpha-1 proteinase inhibitor (alpha-1 antitrypsin deficiency); alpha-1 related emphysema (alpha-1 antitrypsin deficiency); Alpha-galactosidase A deficiency (Fabry disease); ALS (amyotrophic lateral sclerosis); Alstrom syndrome; ALX (Alexander disease); Alzheimer disease; Amelogenesis Imperfecta; Amino levulinic acid dehydratase deficiency (ALA dehydratase deficiency); Aminoacylase 2 deficiency (Canavan disease); amyotrophic lateral sclerosis; Anderson-Fabry disease (Fabry disease); androgen insensitivity syndrome; Anemia; Anemia, hereditary sideroblastic (X-linked sideroblastic anemia); Anemia, sex-linked hypochromic sideroblastic (X-linked sideroblastic anemia); Anemia, splenic, familial (Gaucher disease); Angelman syndrome; Angiokeratoma Corporis *Diffusum* (Fabry's disease); Angiokeratoma diffuse (Fabry's disease); Angiomatosis retinae (von Hippel-Lindau disease); ANH1 (X-linked sideroblastic anemia); APC resistance, Leiden type (factor V Leiden thrombophilia); Apert syndrome; AR deficiency (androgen insensitivity syndrome); AR-CMT2 ee (Charcot-Mare-Tooth disease, type 2); Arachnodactyly (Marfan syndrome); ARNSHL (Nonsyndromic deafness # autosomal recessive); Arthro-ophthalmopathy, hereditary progressive (Stickler syndrome # COL2A 1); Arthrochalasis multiplex congenita (Ehlers-Danlos syndrome # arthrochalasia type); AS (Angelman syndrome); Asp deficiency (Canavan disease); Aspa deficiency (Canavan disease); Aspartoacylase deficiency (Canavan disease); ataxia-telangiectasia; Autism-Dementia-Ataxia-Loss of Purposeful Hand Use syndrome (Rett syndrome); autosomal dominant juvenile ALS (amyotrophic lateral sclerosis, type 4); Autosomal dominant opitz G/BBB syndrome (22q11.2 deletion syndrome); autosomal recessive form of juvenile ALS type 3 (Amyotrophic lateral sclerosis # type 2); Autosomal recessive nonsyndromic hearing loss (Nonsyndromic deafness # autosomal recessive); Autosomal Recessive Sensorineural Hearing Impairment and Goiter (Pendred syndrome); AxD (Alexander disease); Ayerza syndrome (primary pulmonary hypertension); B variant of the Hexosaminidase GM2 gangliosidosis (Sandhoff disease); BANF (neurofibromatosis 2); Beare-Stevenson cutis gyrata syndrome; Benign paroxysmal peritonitis (Mediterranean fever, familial); Benjamin syndrome; beta thalassemia; BH4 Deficiency (tetrahydrobiopterin deficiency); Bilateral Acoustic Neurofibromatosis (neurofibromatosis 2); biotinidase deficiency; bladder cancer; Bleeding disorders (factor V Leiden thrombophilia); Bloch-Sulzberger syndrome (incontinentia pigmenti); Bloom syndrome; Bone diseases; Bone marrow diseases (X-linked sideroblastic anemia); Bonnevie-Ullrich syndrome (Turner syndrome); Bourneville disease (tuberous sclerosis); Bourneville phakomatosis (tuberous sclerosis); Brain diseases (prion disease); breast cancer; Birt-Hogg-Dub6 syndrome; Brittle bone disease (osteogenesis imperfecta); Broad Thumb-Hallux syndrome (Rubinstein-Taybi syndrome); Bronze Diabetes (hemochromatosis); Bronzed cirrhosis (hemochromatosis); Bulbospinal muscular atrophy, X-linked (Kennedy disease); Burger-Grutz syndrome (lipoprotein lipase deficiency, familial); CADASIL; CGD Chronic Granulomatous Disorder; Camptomelic dysplasia; Canavan disease; Cancer; Cancer Family syndrome (hereditary nonpolyposis colorectal cancer); Cancer of breast (breast cancer); Cancer of the bladder (bladder cancer); Carboxylase Deficiency, Multiple, Late-Onset (biotinidase deficiency); Cardiomyopathy (Noonan syndrome); Cat cry syndrome (Cri du chat); CAVD (congenital bilateral absence of vas deferens); Caylor cardiofacial syndrome (22q11.2 deletion syndrome); CBAVD (congenital bilateral absence of vas deferens); Celiac Disease; CEP (congenital erythropoietic *porphyria*); Ceramide trihexosidase deficiency (Fabry disease); Cerebelloretinal Angiomatosis, familial (von Hippel-Lindau disease); Cerebral arteriopathy with subcortical infarcts and leukoencephalopathy (CADASIL); Cerebral autosomal dominant ateriopathy with subcortical infarcts and leukoencephalopathy (CADASIL); Cerebral sclerosis (tuberous sclerosis); Cerebroatrophic Hyperammonemia (Rett syndrome); Cerebroside Lipidosis syndrome (Gaucher disease); CF (cystic fibrosis); CH (congenital hypothyroidism); Charcot disease (amyotrophic lateral sclerosis); Charcot-Marie-Tooth disease; Chondrodystrophia (achondroplasia); Chondrodystrophy syndrome (achondroplasia); Chondrodystrophy with sensorineural deafness (otospondylomegaepiphyseal dysplasia); Chondrogenesis imperfecta (achondrogenesis, type II); Choreoathetosis self-mutilation hyperuricemia syndrome (Lesch-Nyhan syndrome); Classic Galactosemia (galactosemia); Classical Ehlers-Danlos syndrome (Ehlers-Danlos syndrome # classical type); Classical Phenylketonuria (phenylketonuria); Cleft lip and palate (Stickler syndrome); Cloverleaf skull with thanatophoric dwarfism (Thanatophoric dysplasia # type 2); CLS (Coffin-Lowry syndrome); CMT (Charcot-Marie-Tooth disease); Cockayne syndrome; Coffin-Lowry syndrome; collagenopathy, types II and XI; Colon Cancer, familial Nonpolyposis (hereditary nonpolyposis colorectal cancer); Colon cancer, familial (familial adenomatous polyposis); Colorectal Cancer; Complete HPRT deficiency (Lesch-Nyhan syndrome); Complete hypoxanthine-guanine phosphoribosy transferase deficiency (Lesch-Nyhan syndrome); Compression neuropathy (hereditary neuropathy with liability to pressure palsies); Congenital adrenal hyperplasia (21-hydroxylase deficiency); congenital bilateral absence of vas deferens (Congenital absence of the vas deferens); Congenital erythropoietic *porphyria*; Congenital heart disease; Congenital hypomyelination (Charcot-Marie-Tooth disease # Type 1/Charcot-Marie-Tooth disease # Type 4); Congenital hypothyroidism; Congenital methemoglobinemia (Methemoglobinemia # Congenital methaemoglobinaemia); Congenital osteosclerosis (achondroplasia); Congenital sideroblastic anaemia (X-linked sideroblastic anemia); Connective tissue disease; Conotruncal anomaly face syndrome (22q11.2 deletion syndrome); Cooley's Anemia (beta thalassemia); Copper storage disease (Wilson disease); Copper transport disease (Menkes disease); Coproporphyria, hereditary (hereditary coproporphyria); Coproporphyrinogen oxidase deficiency (hereditary coproporphyria); Cowden syndrome; CPO deficiency (hereditary coproporphyria); CPRO deficiency (hereditary coproporphyria); CPX deficiency (hereditary coproporphyria); Craniofacial dysarthrosis (Crouzon syndrome); Craniofacial Dysostosis (Crouzon syndrome); Cretinism (congenital hypothyroidism); Creutzfeldt-Jakob disease (prion disease); Cri du chat (Crohn's disease, fibrostenosing); Crouzon syndrome; Crouzon syndrome with acanthosis *nigricans* (Crouzonodermoskeletal syndrome); Crouzonodermoskeletal syndrome; CS (Cockayne syndrome)(Cowden syndrome); Curschmann-Batten-Steinert syndrome (myotonic dystrophy); cutis gyrata syndrome of Beare-Stevenson (Beare-Stevenson cutis gyrata syndrome); Disorder Mutation Chromosome; D-glycerate dehydrogenase deficiency (hyperoxaluria, primary); Dappled metaphysis syndrome (spondyloepimetaphyseal dysplasia, Strudwick type); DAT—Dementia Alzheimer's type (Alzheimer disease); Genetic hypercalciuria (Dent's disease); DBMD (muscular dystrophy, Duchenne and Becker types); Deafness with goiter (Pendred syndrome); Deafness-retinitis pigmentosa syndrome (Usher syndrome); Deficiency disease, Phenylalanine Hydroxylase (phenylketonuria); Degenerative nerve diseases; de Grouchy syndrome 1 (De Grouchy Syndrome); Dejerine-Sottas syndrome (Charcot-Marie-Tooth disease); Delta-aminolevulinate dehydratase deficiency *porphyria* (ALA dehydratase deficiency); Dementia (CADASIL); demyelinogenic leukodystrophy (Alexander disease); Dermatosparactic type of Ehlers-Danlos syndrome (Ehlers-Danlos syndrome # dermatosparaxis type); Dermatosparaxis (Ehlers-Danlos syndrome # dermatosparaxis type); developmental disabilities; dHMN (Amyotrophic lateral sclerosis # type 4); DHMN-V (distal spinal muscular atrophy, type V); DHTR deficiency (androgen insensitivity syndrome); Diffuse Globoid Body Sclerosis (Krabbe disease); DiGeorge syndrome; Dihydrotestosterone receptor deficiency (androgen insensitivity syndrome); distal spinal muscular atrophy, type V; DM1 (Myotonic dystrophy # type1); DM2 (Myotonic dystrophy # type2); Down syndrome; DSMAV (distal spinal muscular atrophy, type V); DSN (Charcot-Marie-Tooth disease # type 4); DSS (Charcot-Marie-Tooth disease, type 4); Duchenne/Becker muscular dystrophy (muscular dystrophy, Duchenne and Becker types); Dwarf, achondroplastic (achondroplasia); Dwarf, thanatophoric (thanatophoric dysplasia); Dwarfism; Dwarfism-retinal atrophy-deafness syndrome (Cockayne syndrome); dysmyelinogenic leukodystrophy (Alexander disease); Dystrophia myotonica (myotonic dystrophy); dystrophia retinae pigmentosa-dysostosis syndrome (Usher syndrome); Early-Onset familial alzheimer disease (EO-FAD) (Alzheimer disease); EDS (Ehlers-Danlos syndrome); Ehlers-Danlos syndrome; Ekman-Lobstein disease (osteogenesis imperfecta); Entrapment neuropathy (hereditary neuropathy with liability to pressure palsies); Epiloia (tuberous sclerosis); EPP (erythropoietic protoporphyria); Erythroblastic anemia (beta thalassemia); Erythrohepatic protoporphyria (erythropoietic protoporphyria); Erythroid 5-aminolevulinate synthetase deficiency (X-linked sideroblastic anemia); Erythropoietic *porphyria* (congenital erythropoietic *porphyria*); Erythropoietic protoporphyria; Erythropoietic uroporphyria (congenital erythropoietic *porphyria*); Eye cancer (retinoblastoma FA—Friedreich ataxia); Fabry disease; Facial injuries and disorders; Factor V Leiden thrombophilia; FALS (amyotrophic lateral sclerosis); familial acoustic neuroma (neurofibromatosis type II); familial adenomatous polyposis; familial Alzheimer disease (FAD) (Alzheimer disease); familial amyotrophic lateral sclerosis (amyotrophic lateral sclerosis); familial dysautonomia; familial fat-induced hypertriglyceridemia (lipoprotein lipase deficiency, familial); familial hemochromatosis (hemochromatosis); familial LPL deficiency (lipoprotein lipase deficiency, familial); familial nonpolyposis colon cancer (hereditary nonpolyposis colorectal cancer); familial paroxysmal polyserositis (Mediterranean fever, familial); familial PCT (*porphyria* cutanea *tarda*); familial pressure sensitive neuropathy (hereditary neuropathy with liability to pressure palsies); familial primary pulmonary hypertension (FPPH) (primary pulmonary hypertension); Familial Turner syndrome (Noonan syndrome); familial vascular leukoencephalopathy (CADASIL); FAP (familial adenomatous polyposis); FD (familial dysautonomia); Female pseudo-Turner syndrome (Noonan syndrome); Ferrochelatase deficiency (erythropoietic protoporphyria); ferroportin disease (Haemochromatosis # type 4); Fever (Mediterranean fever, familial); FG syndrome; FGFR3-associated coronal synostosis (Muenke syndrome); Fibrinoid degeneration of astrocytes (Alexander disease); Fibrocystic disease of the pancreas (cystic fibrosis); FMF (Mediterranean fever, familial); Folling disease (phenylketonuria); fra(X) syndrome (fragile X syndrome); fragile X syndrome; Fragilitas ossium (osteogenesis imperfecta); FRAXA syndrome (fragile X syndrome); FRDA (Friedreich's ataxia); Friedreich ataxia (Friedreich's ataxia); Friedreich's ataxia; FXS (fragile X syndrome); G6PD deficiency; Galactokinase deficiency disease (galactosemia); Galactose-1-phosphate uridyl-transferase deficiency disease (galactosemia); galactosemia; Galactosylceramidase deficiency disease (Krabbe disease); Galactosylceramide lipidosis (Krabbe disease); galactosylcerebrosidase deficiency (Krabbe disease); galactosylsphingosine lipidosis (Krabbe disease); GALC deficiency (Krabbe disease); GALT deficiency (galactosemia); Gaucher disease; Gaucher-like disease (pseudo-Gaucher disease); GBA deficiency (Gaucher disease type 1); GD (Gaucher's disease); Genetic brain disorders; genetic emphysema (alpha-1 antitrypsin deficiency); genetic hemochromatosis (hemochromatosis); Giant cell hepatitis, neonatal (Neonatal hemochromatosis); GLA deficiency (Fabry disease); Glioblastoma, retinal (retinoblastoma); Glioma, retinal (retinoblastoma); globoid cell leukodystrophy (GCL, GLD) (Krabbe disease); globoid cell leukoencephalopathy (Krabbe disease); Glucocerebrosidase deficiency (Gaucher disease); Glucocerebrosidosis (Gaucher disease); Glucosyl cerebroside lipidosis (Gaucher disease); Glucosylceramidase deficiency (Gaucher disease); Glucosylceramide beta-glucosidase deficiency (Gaucher disease); Glucosylceramide lipidosis (Gaucher disease); Glyceric aciduria (hyperoxaluria, primary); Glycine encephalopathy (Nonketotic hyperglycinemia); Glycolic aciduria (hyperoxaluria, primary); GM2 gangliosidosis, type 1 (Tay-Sachs disease); Goiter-deafness syndrome (Pendred syndrome); Graefe-Usher syndrome (Usher syndrome); Gronblad-Strandberg syndrome (pseudoxanthoma elasticum); Guenther *porphyria* (congenital erythropoietic *porphyria*); Gunther disease (congenital erythropoietic *porphyria*); Haemochromatosis (hemochromatosis); Hallgren syndrome (Usher syndrome); Harlequin Ichthyosis; Hb S disease (sickle cell anemia); HCH (hypochondroplasia); HCP (hereditary coproporphyria); Head and brain malformations; Hearing disorders and deafness; Hearing problems in children; HEF2A (hemochromatosis # type 2); HEF2B (hemochromatosis # type 2); Hematoporphyria (*porphyria*); Heme synthetase deficiency (erythropoietic protoporphyria); Hemochromatoses (hemochromatosis); hemochromatosis; hemoglobin M disease (methemoglobinemia # beta-globin type); Hemoglobin S disease (sickle cell anemia); hemophilia; HEP (hepatoerythropoietic *porphyria*); hepatic AGT deficiency (hyperoxaluria, primary); hepatoerythropoietic *porphyria*; Hepatolenticular degeneration syndrome (Wilson disease); Hereditary arthro-ophthalmopathy (Stickler syndrome); Hereditary coproporphyria; Hereditary dystopic lipidosis (Fabry disease); Hereditary hemochromatosis (HHC) (hemochromatosis); Hereditary Inclusion Body Myopathy (skeletal muscle regeneration); Hereditary iron-loading anemia (X-linked sideroblastic anemia); Hereditary motor and sensory neuropathy (Charcot-Marie-Tooth disease); Hereditary motor neuronopathy (spinal muscular atrophy); Hereditary motor neuronopathy, type V (distal spinal muscular atrophy, type V); Hereditary Multiple Exostoses; Hereditary nonpolyposis colorectal cancer; Hereditary periodic fever syndrome (Mediterranean fever, familial); Hereditary Polyposis *Coli* (familial adenomatous polyposis); Hereditary pulmonary emphysema (alpha-1 antitrypsin deficiency); Hereditary resistance to activated protein C (factor V Leiden thrombophilia); Hereditary sensory and autonomic neuropathy type III (familial dysautonomia); Hereditary spastic paraplegia (infantile-onset ascending hereditary spastic paralysis); Hereditary spinal ataxia (Friedreich ataxia); Hereditary spinal sclerosis (Friedreich ataxia); Herrick's anemia (sickle cell anemia); Heterozygous OSMED (Weissenbacher-Zweymiiller syndrome); Heterozygous otospondylomegaepiphyseal dysplasia (Weissenbacher-Zweymiller syndrome); HexA deficiency (Tay-Sachs disease); Hexosaminidase A deficiency (Tay-Sachs disease); Hexosaminidase alpha-subunit deficiency (variant B) (Tay-Sachs disease); HFE-associated hemochromatosis (hemochromatosis); HGPS (Progeria); Hippel-Lindau disease (von Hippel-Lindau disease); HLAH (hemochromatosis); HMN V (distal spinal muscular atrophy, type V); HMSN (Charcot-Marie-Tooth disease); HNPCC (hereditary nonpolyposis colorectal cancer); HNPP (hereditary neuropathy with liability to pressure palsies); homocystinuria; Homogentisic acid oxidase deficiency (alkaptonuria); Homogentisic aciduria (alkaptonuria); Homozygous *porphyria cutanea tarda* (hepatoerythropoietic *porphyria*); HP1 (hyperoxaluria, primary); HP2 (hyperoxaluria, primary); HPA (hyperphenylalaninemia); HPRT—Hypoxanthine-guanine phosphoribosyltransferase deficiency (Lesch-Nyhan syndrome); HSAN type III (familial dysautonomia); HSAN3 (familial dysautonomia); HSN-III (familial dysautonomia); Human dermatosparaxis (Ehlers-Danlos syndrome # dermatosparaxis type); Huntington's disease; Hutchinson-Gilford progeria syndrome (progeria); Hyperandrogenism, nonclassic type, due to 21-hydroxylase deficiency (21-hydroxylase deficiency); Hyperchylomicronemia, familial (lipoprotein lipase deficiency, familial); hyperglycinemia with ketoacidosis and leukopenia (propionic acidemia); Hyperlipoproteinemia type I (lipoprotein lipase deficiency, familial); hyperoxaluria, primary; hyperphenylalaninaemia (hyperphenylalaninemia); hyperphenylalaninemia; Hypochondrodysplasia (hypochondroplasia); hypochondrogenesis; hypochondroplasia; Hypochromic anemia (X-linked sideroblastic anemia); Hypocupremia, congenital; Menkes syndrome); hypoxanthine phosphoribosyltransferse (HPRT) deficiency (Lesch-Nyhan syndrome); IAHSP (infantile-onset ascending hereditary spastic paralysis); idiopathic hemochromatosis (hemochromatosis, type 3); Idiopathic neonatal hemochromatosis (hemochromatosis, neonatal); Idiopathic pulmonary hypertension (primary pulmonary hypertension); Immune system disorders (X-linked severe combined immunodeficiency); Incontinentia Pigmenti; Infantile cerebral Gaucher's disease (Gaucher disease type 2); Infantile Gaucher disease (Gaucher disease type 2); infantile-onset ascending hereditary spastic paralysis; Infertility; inherited emphysema (alpha-1 antitrypsin deficiency); Inherited human transmissible spongiform encephalopathies (prion disease); inherited tendency to pressure palsies (hereditary neuropathy with liability to pressure palsies); Insley-Astley syndrome (otospondylomegaepiphyseal dysplasia); Intermittent acute *porphyria* syndrome (acute intermittent *porphyria*); Intestinal polyposis-cutaneous pigmentation syndrome (Peutz-Jeghers syndrome); IP (incontinentia pigmenti); Iron storage disorder (hemochromatosis); Isodicentric 15 (idicl5); Isolated deafness (nonsyndromic deafness); Jackson-Weiss syndrome; JH (Haemochromatosis # type 2); Joubert syndrome; JPLS (Juvenile Primary Lateral Sclerosis); juvenile amyotrophic lateral sclerosis (Amyotrophic lateral sclerosis # type 2); Juvenile gout, choreoathetosis, mental retardation syndrome (Lesch-Nyhan syndrome); juvenile hyperuricemia syndrome (Lesch-Nyhan syndrome); JWS (Jackson-Weiss syndrome); KD (X-linked spinal-bulbar muscle atrophy); Kennedy disease (X-linked spinal-bulbar muscle atrophy); Kennedy spinal and bulbar muscular atrophy (X-linked spinal-bulbar muscle atrophy); Kerasin histiocytosis (Gaucher disease); Kerasin lipoidosis (Gaucher disease); Kerasin thesaurismosis (Gaucher disease); ketotic glycinemia (propionic acidemia); ketotic hyperglycinemia (propionic acidemia); Kidney diseases (hyperoxaluria, primary); Klinefelter syndrome; Klinefelter's syndrome; Kniest dysplasia; Krabbe disease; Lacunar dementia (CADASIL); Langer-Saldino achondrogenesis (achondrogenesis, type II); Langer-Saldino dysplasia (achondrogenesis, type II); Late-onset Alzheimer disease (Alzheimer disease # type 2); Late-onset familial Alzheimer disease (AD2) (Alzheimer disease # type 2); late-onset Krabbe disease (LOKD) (Krabbe disease); Learning Disorders (Learning disability); Lentiginosis, perioral (Peutz-Jeghers syndrome); Lesch-Nyhan syndrome; Leukodystrophies; leukodystrophy with Rosenthal fibers (Alexander disease); Leukodystrophy, spongiform (Canavan disease); LFS (Li-Fraumeni syndrome); Li-Fraumeni syndrome; Lipase D deficiency (lipoprotein lipase deficiency, familial); LIPD deficiency (lipoprotein lipase deficiency, familial); Lipidosis, cerebroside (Gaucher disease); Lipidosis, ganglioside, infantile (Tay-Sachs disease); Lipoid histiocytosis (kerasin type) (Gaucher disease); lipoprotein lipase deficiency, familial; Liver diseases (galactosemia); Lou Gehrig disease (amyotrophic lateral sclerosis); Louis-Bar syndrome (ataxia-telangiectasia); Lynch syndrome (hereditary nonpolyposis colorectal cancer); Lysyl-hydroxylase deficiency (Ehlers-Danlos syndrome # kyphoscoliosis type); Machado-Joseph disease (Spinocerebellar ataxia # type 3); Male breast cancer (breast cancer); Male genital disorders; Male Turner syndrome (Noonan syndrome); Malignant neoplasm of breast (breast cancer); malignant tumor of breast (breast cancer); Malignant tumor of urinary bladder (bladder cancer); Mammary cancer (breast cancer); Marfan syndrome 15; Marker X syndrome (fragile X syndrome); Martin-Bell syndrome (fragile X syndrome); McCune-Albright syndrome; McLeod syndrome; MEDNIK; Mediterranean Anemia (beta thalassemia); Mediterranean fever, familial; Mega-epiphyseal dwarfism (otospondylomegaepiphyseal dysplasia); Menkea syndrome (Menkes syndrome); Menkes syndrome; Mental retardation with osteocartilaginous abnormalities (Coffin-Lowry syndrome); Metabolic disorders; Metatropic dwarfism, type II (Kniest dysplasia); Metatropic dysplasia type II (Kniest dysplasia); Methemoglobinemia # beta-globin type; methylmalonic acidemia; MFS (Marfan syndrome); MHAM (Cowden syndrome); MK (Menkes syndrome); Micro syndrome; Microcephaly; MMA (methylmalonic acidemia); MNK (Menkes syndrome); Monosomy 1p36 syndrome (1p36 deletion syndrome); monosomy X (Turner syndrome); Motor neuron disease, amyotrophic lateral sclerosis (amyotrophic lateral sclerosis); Movement disorders; Mowat-Wilson syndrome; Mucopolysaccharidosis (MPS I); Mucoviscidosis (cystic fibrosis); Muenke syndrome; Multi-Infarct dementia (CADASIL); Multiple carboxylase deficiency, late-onset (biotinidase deficiency); Multiple hamartoma syndrome (Cowden syndrome); Multiple neurofibromatosis (neurofibromatosis); Muscular dystrophy; Muscular dystrophy, Duchenne and Becker type; Myotonia atrophica (myotonic dystrophy); Myotonia dystrophica (myotonic dystrophy); myotonic dystrophy; Myxedema, congenital (congenital hypothyroidism); Nance-Insley syndrome (otospondylomegaepiphyseal dysplasia); Nance-Sweeney chondrodysplasia (otospondylomegaepiphyseal dysplasia); NBIA1 (pantothenate kinase-associated neurodegeneration); Neill-Dingwall syndrome (Cockayne syndrome); Neuroblastoma, retinal (retinoblastoma); Neurodegeneration with brain iron accumulation type 1 (pantothenate kinase-associated neurodegeneration); Neurofibromatosis type I; Neurofibromatosis type II; Neurologic diseases; Neuromuscular disorders; neuronopathy, distal hereditary motor, type V (Distal spinal muscular atrophy # type V); neuronopathy, distal hereditary motor, with pyramidal features (Amyotrophic lateral sclerosis # type 4); NF (neurofibromatosis); Niemann-Pick (Niemann-Pick disease); Noack syndrome (Pfeiffer syndrome); Nonketotic hyperglycinemia (Glycine encephalopathy); Non-neuronopathic Gaucher disease (Gaucher disease type 1); Non-phenylketonuric hyperphenylalaninemia (tetrahydrobiopterin deficiency); nonsyndromic deafness; Noonan syndrome; Norrbottnian Gaucher disease (Gaucher disease type 3); Ochronosis (alkaptonuria); Ochronotic arthritis (alkaptonuria); OI (osteogenesis imperfecta); OSMED (otospondylomegaepiphyseal dysplasia); osteogenesis imperfecta; Osteopsathyrosis (osteogenesis imperfecta); Osteosclerosis congenita (achondroplasia); Oto-spondylo-megaepiphyseal dysplasia (otospondylomegaepiphyseal dysplasia); otospondylomegaepiphyseal dysplasia; Oxalosis (hyperoxaluria, primary); Oxaluria, primary (hyperoxaluria, primary); pantothenate kinase-associated neurodegeneration; Patau Syndrome (Trisomy 13); PBGD deficiency (acute intermittent *porphyria*); PCC deficiency (propionic acidemia); PCT (*porphyria* cutanea *tarda*); PDM (Myotonic dystrophy # type 2); Pendred syndrome; Periodic disease (Mediterranean fever, familial); Periodic peritonitis (Mediterranean fever, familial); Periorificial lentiginosis syndrome (Peutz-Jeghers syndrome); Peripheral nerve disorders (familial dysautonomia); Peripheral neurofibromatosis (neurofibromatosis 1); Peroneal muscular atrophy (Charcot-Marie-Tooth disease); peroxisomal alanine:glyoxylate aminotransferase deficiency (hyperoxaluria, primary); Peutz-Jeghers syndrome; Pfeiffer syndrome; Phenylalanine hydroxylase deficiency disease (phenylketonuria); phenylketonuria; Pheochromocytoma (von Hippel-Lindau disease); Pierre Robin syndrome with fetal chondrodysplasia (Weissenbacher-Zweymiiller syndrome); Pigmentary cirrhosis (hemochromatosis); PJS (Peutz-Jeghers syndrome); PKAN (pantothenate kinase-associated neurodegeneration); PKU (phenylketonuria); Plumboporphyria (ALA deficiency *porphyria*); PMA (Charcot-Marie-tooth disease); polyostotic fibrous dysplasia (McCune-Albright syndrome); polyposis *coli* (familial adenomatous polyposis); polyposis, hamartomatous intestinal (Peutz-Jeghers syndrome); polyposis, intestinal, II (Peutz-Jeghers syndrome); polyps-and-spots syndrome (Peutz-Jeghers syndrome); Porphobilinogen synthase deficiency (ALA deficiency *porphyria*); *porphyria*; porphyrin disorder (*porphyria*); PPH (primary pulmonary hypertension); PPOX deficiency (variegate *porphyria*); Prader-Labhart-Willi syndrome (Prader-Willi syndrome); Prader-Willi syndrome; presenile and senile dementia (Alzheimer disease); primary hemochromatosis (hemochromatosis); primary hyperuricemia syndrome (Lesch-Nyhan syndrome); primary pulmonary hypertension; primary senile degenerative dementia (Alzheimer disease); prion disease; procollagen type EDS VII, mutant (Ehlers-Danlos syndrome # arthrochalasia type); progeria (Hutchinson Gilford Progeria Syndrome); Progeria-like syndrome (Cockayne syndrome); progeroid nanism (Cockayne syndrome); progressive chorea, chronic hereditary (Huntington) (Huntington's disease); progressive muscular atrophy (spinal muscular atrophy); progressively deforming osteogenesis imperfecta with normal sclerae (Osteogenesis imperfecta # type III); PROMM (Myotonic dystrophy # type 2); propionic academia; propionyl-CoA carboxylase deficiency (propionic acidemia); protein C deficiency; protein S deficiency; protoporphyria (erythropoietic protoporphyria); protoporphyrinogen oxidase deficiency (variegate *porphyria*); proximal myotonic dystrophy (Myotonic dystrophy # type 2); proximal myotonic myopathy (Myotonic dystrophy # type 2); pseudo-Gaucher disease; pseudo-Ullrich-Turner syndrome (Noonan syndrome); pseudoxanthoma elasticum; psychosine lipidosis (Krabbe disease); pulmonary arterial hypertension (primary pulmonary hypertension); pulmonary hypertension (primary pulmonary hypertension); PWS (Prader-Willi syndrome); PXE—pseudoxanthoma elasticum (pseudoxanthoma elasticum); Rb (retinoblastoma); Recklinghausen disease, nerve (neurofibromatosis 1); Recurrent polyserositis (Mediterranean fever, familial); Retinal disorders; Retinitis pigmentosa-deafness syndrome (Usher syndrome); Retinoblastoma; Rett syndrome; RFALS type 3 (Amyotrophic lateral sclerosis # type 2); Ricker syndrome (Myotonic dystrophy # type 2); Riley-Day syndrome (familial dysautonomia); Roussy-Levy syndrome (Charcot-Marie-Tooth disease); RSTS (Rubinstein-Taybi syndrome); RTS (Rett syndrome) (Rubinstein-Taybi syndrome); RTT (Rett syndrome); Rubinstein-Taybi syndrome; Sack-Barabas syndrome (Ehlers-Danlos syndrome, vascular type); SADDAN; sarcoma family syndrome of Li and Fraumeni (Li-Fraumeni syndrome); sarcoma, breast, leukemia, and adrenal gland (SBLA) syndrome (Li-Fraumeni syndrome); SBLA syndrome (Li-Fraumeni syndrome); SBMA (X-linked spinal-bulbar muscle atrophy); SCD (sickle cell anemia); Schwannoma, acoustic, bilateral (neurofibromatosis 2); SCIDX1 (X-linked severe combined immunodeficiency); sclerosis *tuberosa* (tuberous sclerosis); SDAT (Alzheimer disease); SED congenita (spondyloepiphyseal dysplasia congenita); SED Strudwick (spondyloepimetaphyseal dysplasia, Strudwick type); SEDc (spondyloepiphyseal dysplasia congenita); SEMD, Strudwick type (spondyloepimetaphyseal dysplasia, Strudwick type); senile dementia (Alzheimer disease # type 2); severe achondroplasia with developmental delay and acanthosis *nigricans* (SADDAN); Shprintzen syndrome (22q11.2 deletion syndrome); sickle cell anemia; skeleton-skin-brain syndrome (SADDAN); Skin pigmentation disorders; SMA (spinal muscular atrophy); SMED, Strudwick type (spondyloepimetaphyseal dysplasia, Strudwick type); SMED, type I (spondyloepimetaphyseal dysplasia, Strudwick type); Smith Lemli Opitz Syndrome; South-African genetic *porphyria* (variegate *porphyria*); spastic paralysis, infantile onset ascending (infantile-onset ascending hereditary spastic paralysis); Speech and communication disorders; sphingolipidosis, Tay-Sachs (Tay-Sachs disease); spinal-bulbar muscular atrophy; spinal muscular atrophy; spinal muscular atrophy, distal type V (Distal spinal muscular atrophy # type V); spinal muscular atrophy, distal, with upper limb predominance (Distal spinal muscular atrophy # type V); spinocerebellar ataxia; spondyloepimetaphyseal dysplasia, Strudwick type; spondyloepiphyseal dysplasia congenital; spondyloepiphyseal dysplasia (collagenopathy, types II and XI); spondylometaepiphyseal dysplasia congenita, Strudwick type (spondyloepimetaphyseal dysplasia, Strudwick type); spondylometaphyseal dysplasia (SMD) (spondyloepimetaphyseal dysplasia, Strudwick type); spondylometaphyseal dysplasia, Strudwick type (spondyloepimetaphyseal dysplasia, Strudwick type); spongy degeneration of central nervous system (Canavan disease); spongy degeneration of the brain (Canavan disease); spongy degeneration of white matter in infancy (Canavan disease); sporadic primary pulmonary hypertension (primary pulmonary hypertension); SSB syndrome (SADDAN); steely hair syndrome (Menkes syndrome); Steinert disease (myotonic dystrophy); Steinert myotonic dystrophy syndrome (myotonic dystrophy); Stickler syndrome; stroke (CADASIL); Strudwick syndrome (spondyloepimetaphyseal dysplasia, Strudwick type); subacute neuronopathic Gaucher disease (Gaucher disease type 3); Swedish genetic *porphyria* (acute intermittent *porphyria*); Swedish *porphyria* (acute intermittent *porphyria*); Swiss cheese cartilage dysplasia (Kniest dysplasia); Tay-Sachs disease; TD—thanatophoric dwarfism (thanatophoric dysplasia); TD with straight femurs and cloverleaf skull (thanatophoric dysplasia # Type 2); Telangiectasia, cerebello-oculocutaneous (ataxia-telangiectasia); Testicular feminization syndrome (androgen insensitivity syndrome); tetrahydrobiopterin deficiency; TFM—testicular feminization syndrome (androgen insensitivity syndrome); thalassemia *intermedia* (beta thalassemia); Thalassemia Major (beta thalassemia); thanatophoric dysplasia; thiamine-responsive megaloblastic anemia with diabetes mellitus and sensorineural deafness; Thrombophilia due to deficiency of cofactor for activated protein C, Leiden type (factor V Leiden thrombophilia); Thyroid disease; Tomaculous neuropathy (hereditary neuropathy with liability to pressure palsies); Total HPRT deficiency (Lesch-Nyhan syndrome); Total hypoxanthine-guanine phosphoribosyl transferase deficiency (Lesch-Nyhan syndrome); Tourette's Syndrome; Transmissible dementias (prion disease); Transmissible spongiform encephalopathies (prion disease); Treacher Collins syndrome; Trias fragilitis ossium (osteogenesis imperfecta # Type I); triple X syndrome; Triplo X syndrome (triple X syndrome); Trisomy 21 (Down syndrome); Trisomy X (triple X syndrome); Troisier-Hanot-Chauffard syndrome (hemochromatosis); TS (Turner syndrome); TSD (Tay-Sachs disease); TSEs (prion disease); tuberose sclerosis (tuberous sclerosis); tuberous sclerosis; Turner syndrome; Turner syndrome in female with X chromosome (Noonan syndrome); Turner's phenotype, karyotype normal (Noonan syndrome); Turner's syndrome (Turner syndrome); Turner-like syndrome (Noonan syndrome); Type 2 Gaucher disease (Gaucher disease type 2); Type 3 Gaucher disease (Gaucher disease type 3); UDP-galactose-4-epimerase deficiency disease (galactosemia); UDP glucose 4-epimerase deficiency disease (galactosemia); UDP glucose hexose-1-phosphate uridylyltransferase deficiency (galactosemia); Ullrich-Noonan syndrome (Noonan syndrome); Ullrich-Turner syndrome (Turner syndrome); Undifferentiated deafness (nonsyndromic deafness); UPS deficiency (acute intermittent *porphyria*); Urinary bladder cancer (bladder cancer); UROD deficiency (*porphyria* cutanea *tarda*); Uroporphyrinogen decarboxylase deficiency (*porphyria* cutanea *tarda*); Uroporphyrinogen synthase deficiency (acute intermittent *porphyria*); UROS deficiency (congenital erythropoietic *porphyria*); Usher syndrome; UTP hexose-1-phosphate uridylyltransferase deficiency (galactosemia); Van Bogaert-Bertrand syndrome (Canavan disease); Van der Hoeve syndrome (osteogenesis imperfecta # Type I); variegate *porphyria*; Velocardiofacial syndrome (22q11.2 deletion syndrome); VHL syndrome (von Hippel-Lindau disease); Vision impairment and blindness (Alstrom syndrome); Von Bogaert-Bertrand disease (Canavan disease); von Hippel-Lindau disease; Von Recklenhausen-Applebaum disease (hemochromatosis); von Recklinghausen disease (neurofibromatosis 1); VP (variegate *porphyria*); Vrolik disease (osteogenesis imperfecta); Waardenburg syndrome; Warburg Sjo Fledelius Syndrome (Micro syndrome); WD (Wilson disease); Weissenbacher-Zweymiiller syndrome; Wilson disease; Wilson's disease (Wilson disease); Wolf-Hirschhorn syndrome; Wolff Periodic disease (Mediterranean fever, familial); WZS (Weissenbacher-Zweymiiller syndrome); Xeroderma Pigmentosum; X-linked mental retardation and macroorchidism (fragile X syndrome); X-linked primary hyperuricemia (Lesch-Nyhan syndrome); X-linked severe combined immunodeficiency; X-linked sideroblastic anemia; X-linked spinal-bulbar muscle atrophy (Kennedy disease); X-linked uric aciduria enzyme defect (Lesch-Nyhan syndrome); X-SCID (X-linked severe combined immunodeficiency); XLSA (X-linked sideroblastic anemia); XSCID (X-linked severe combined immunodeficiency); XXX syndrome (triple X syndrome); XXXX syndrome (48, XXXX); XXXXX syndrome (49, XXXXX); XXY syndrome (Klinefelter syndrome); XXY trisomy (Klinefelter syndrome); XYY karyotype (47,XYY syndrome); XYY syndrome (47,XYY syndrome); and YY syndrome (47,XYY syndrome).

In a further preferred aspect, the modified RNA as defined herein or the composition comprising a plurality of modified RNA's as defined herein may be used for the preparation of a pharmaceutical composition, particularly for purposes as defined herein, preferably for the use in gene therapy or genetic vaccination in the treatment of diseases as defined herein.

The pharmaceutical composition may furthermore be used in gene therapy or genetic vaccination particularly in the treatment of a disease or a disorder, preferably as defined herein.

According to a further aspect, the present invention also provides kits, particularly kits of parts. Such kits, particularly kits of parts, typically comprise as components alone or in combination with further components as defined herein at least one modified RNA as defined herein, the pharmaceutical composition or vaccine comprising the modified RNA. The at least one modified RNA as defined herein, is optionally in combination with further components as defined herein, whereby the at least one modified RNA according to the invention is provided separately (first part of the kit) from at least one other part of the kit comprising one or more other components. The pharmaceutical composition may e.g. occur in one or different parts of the kit. As an example, e.g. at least one part of the kit may comprise at least one modified RNA as defined herein, and at least one further part of the kit at least one other component as defined herein, e.g. at least one other part of the kit may comprise at least one pharmaceutical composition or a part thereof, e.g. at least one part of the kit may comprise the modified RNA as defined herein, at least one further part of the kit at least one other component as defined herein, at least one further part of the kit at least one component of the pharmaceutical composition or the pharmaceutical composition as a whole, and at least one further part of the kit e.g. at least one pharmaceutical carrier or vehicle, etc. In case the kit or kit of parts comprises a plurality of modified RNA molecules, one component of the kit can comprise only one, several or all modifiedRNA molecules comprised in the kit. In an alternative embodiment every/each modified RNA may be comprised in a different/separate component of the kit such that each component forms a part of the kit. Also, more than one modified RNA may be comprised in a first component as part of the kit, whereas one or more other (second, third etc.) components (providing one or more other parts of the kit) may either contain one or more than one modified RNA's, which may be identical or partially identical or different from the first component. The kit or kit of parts may furthermore contain technical instructions with information on the administration and dosage of the modified RNA, the pharmaceutical composition or of any of its components or parts, e.g. if the kit is prepared as a kit of parts.

Preferably, the kit according to the invention comprises the modified RNA, preferably in lyophilized form and a suitable vector for reconstitution of the modified RNA. In a preferred embodiment the modified RNA is provided in a container, preferably in a container, in which the modified RNA is resolubilized. Preferably, the container can be connected to a needle-free injection device, e.g. for filling a disposable syringe of a the needle-free injection device.

Additionally, the invention relates to a method for enhancing the (localized) expression of RNA-encoded peptides or proteins in the dermis or muscle (of a mammal) comprising administering the modified RNA as defined herein by jet injection.

Furthermore, the present invention provides a method for treating or preventing a disease or disorder comprising administration of a modified RNA as defined herein by jet injection to a subject in need thereof, particularly a human patient.

The method of treating or preventing a disorder according to the present invention is preferably a vaccination method and/or a gene therapy method as described above.

EXAMPLES

The examples shown in the following are merely illustrative and shall describe the present invention in a further way. These examples shall not be construed to limit the present invention thereto.

1. Expression of Luciferase In Vivo

Preparation of DNA-Templates

A vector for in vitro transcription was constructed containing a T7 promoter followed by a GC-enriched sequence coding for *Photinus pyralis* luciferase (PpLuc(GC)), a mutated 3'-UTR of alpha globin (muag), an A64 poly(A) sequence, a poly(C) sequence (C30) and a histone stem-loop sequence (histone-SL):

SEQ ID No. 46 (FIG. 4): PpLuc(GC)-muag-A64-C30-histoneSL (R1265)

For comparison a vector was constructed containing a T7 promoter followed by a wild type sequence coding for *Photinus pyralis* luciferase (PpLuc(wt)) and a A30 poly(A) sequence:

SEQ ID No. 47 (FIG. 5): PpLuc(wt)-A30 (R2652)

To determine the effect of the used modifications following vectors were constructed:

SEQ ID No. 48 (FIG. 6): PpLuc(wt)-A64 (R3454)

SEQ ID No. 49 (FIG. 7): PpLuc(GC)-A64-C30-HistoneSL (R2462)

SEQ ID No. 50 (FIG. 8): PpLuc(GC)-muag-A64-C30 (R1256)

SEQ ID No. 51 (FIG. 9): PpLuc(nat)-muag-A64-C30-HistoneSL (R2393)

For Further Experiments, the Following Vector Encoding the G Protein of Rabies Virus (RAV-G) was Constructed:

Simarly to the vector PpLuc(GC)-muag-A64-C30-histoneSL (R1265) encoding luciferase, RAV-G(GC)-muag-A64-C30-histoneSL (R2403) contains a T7 promoter followed by a GC-enriched sequence encoding the G protein of Rabies virus, a mutated 3'-UTR of alpha globin (muag), an A64 poly(A) sequence, a poly(C) sequence (C30) and a histone stem-loop sequence (histone-SL):

SEQ ID No. 52 (FIG. 10): RAV-G(GC)-muag-A64-C30-histoneSL (R2403)

For Further Experiments, the Following Vectors Encoding Murine EPO Were Constructed:

A vector for in vitro transcription was constructed containing a T7 promoter followed by the 5'-TOP-UTR sequence of HSD17B4, a GC-enriched sequence encoding EPO (EPO(GC)), the 3'-UTR sequence of albumin (albumin7), an A64 poly(A) sequence, a poly(C) sequence (C30) and a histone stem-loop sequence (histone-SL):
SEQ ID No. 54 (FIG. 12): HSD17B4-EPO(GC)-albumin7-A64-C30-histoneSL (R3135)

For comparison, a vector was constructed containing a T7 promoter followed by a wild type sequence encoding EPO (EPO(wt)) and an A30 poly(A) sequence:
SEQ ID No. 53 (FIG. 11): EPO(wt)-A30 (R3513)

In Vitro Transcription

The DNA-templates according to Example 1 were linearized and transcribed in vitro using T7-Polymerase. The DNA-template was then digested by DNase-treatment. mRNA transcripts contained a 5'-CAP structure (mCap) obtained by adding an excess of N7-Methyl-Guanosine-5'-Triphosphate-5'-Guanosine to the transcription reaction. mRNA thus obtained was purified and resuspended in water.

Expression of Luciferase In Vivo:

For determining luciferase expression in vivo, guinea pigs were intradermally injected with the indicated amounts of naked mRNA by jet injection.

After 24 h, the animals were sacrificed and the samples (ear, skin from the back or muscle) were collected, frozen at −78° C. and lysed for 3 minutes at full speed in a tissue lyser (Qiagen, Hilden, Germany). Afterwards 600 l of lysis buffer (25 mM Tris, pH 7.5 (HCl), 2 mM EDTA, 10% glycerol, 1% Triton X-100, 2 mM DTT, 1 mM PMSF) were added and the resulting solutions were subjected another 6 minutes at full speed in the tissue lyser. After 10 minutes of centrifugation at 13,500 rpm at 4° C., the supernatants were mixed with luciferin buffer (25 mM Glycylglycin, 15 mM MgSO4, 5 mM ATP, 62.5 µM luciferin) and luminiscence was detected using a luminometer (Lumat LB 9507 (Berthold Technologies, Bad Wildbad, Germany)).

Figure 1:
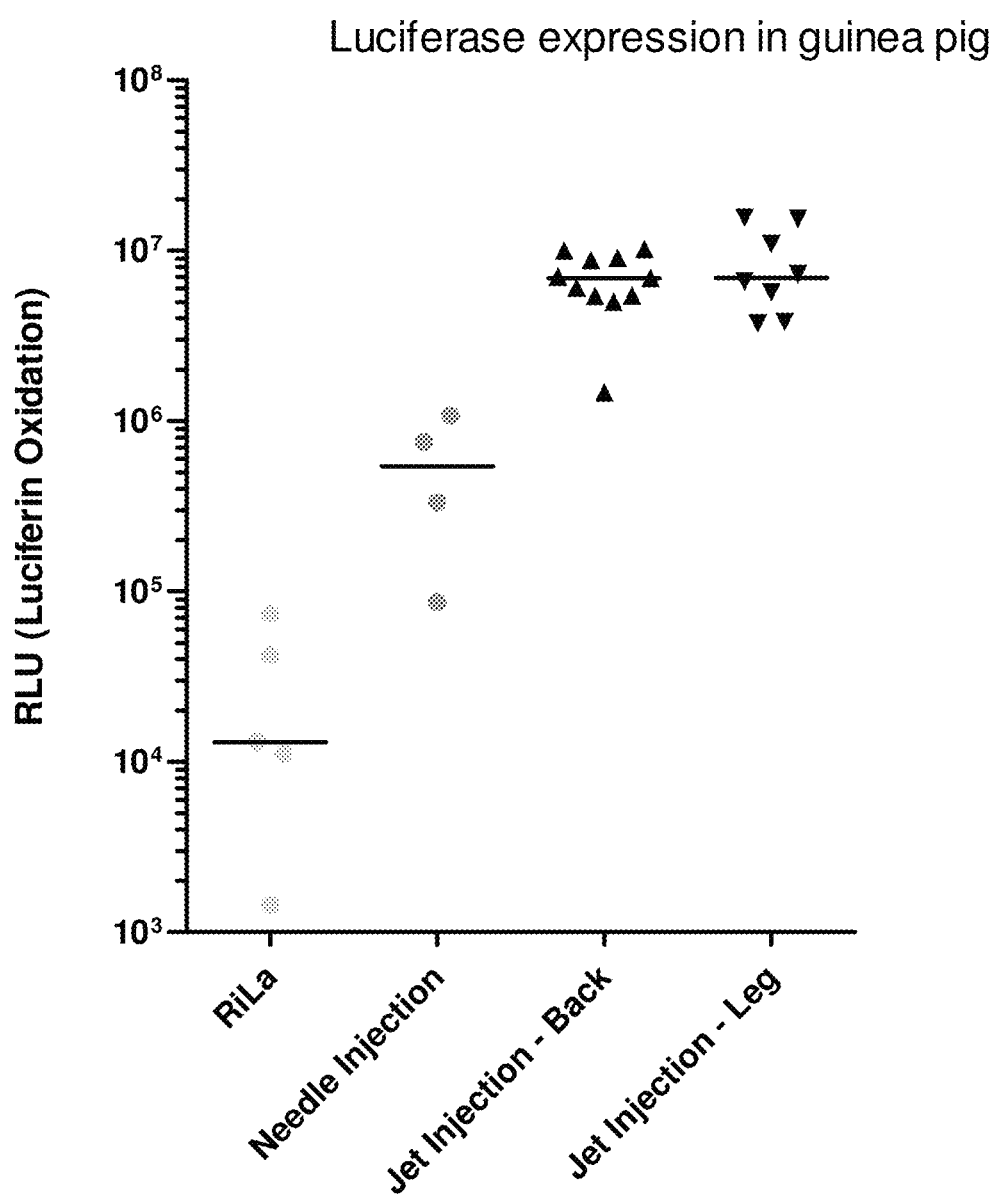
FIG. 1: Luciferase expression in guinea pigs

Results:

As a first result, it has been found that expression of luciferase encoded by a modified mRNA is strongly enhanced in guinea pigs by jet injection compared to conventional intradermal needle injection (see FIG. 1).

Moreover, it has surprisingly been found that the saturation level of expression could be increased by jet injection compared to conventionally injected mRNA by needle-syringe (see FIG. 2).

Unexpectedly, it could further be shown that the expression of luciferase from a modified mRNA (PpLuc(GC)) is significantly more enhanced by jet injection than the expression of luciferase from an unmodified reference mRNA (PpLuc(wt); see FIG. 3).

TABLE 1

Summary of the measured increase in protein expression

|  | Luciferase expression | Effect of jet injection | Effect of modification | Effect of jet injection and modification |
|---|---|---|---|---|
| PpLuc(GC) 5 µg - conv. | 275476 |  | 123 |  |
| PpLuc(GC) 5 µg - Jet | 2267492 |  |  | 1013 |
| PpLuc(wt) 5 µg - conv. | 2238 |  |  |  |

TABLE 1-continued

Summary of the measured increase in protein expression

|  | Luciferase expression | Effect of jet injection | Effect of modification | Effect of jet injection and modification |
|---|---|---|---|---|
| PpLuc(wt) 5 µg - Jet | 4469 | 2 |  |  |
| PpLuc(GC) 80 µg - conv. | 1926120 |  | 117 |  |
| PpLuc(GC) 80 µg - Jet | 17932040 |  |  | 1089 |
| PpLuc(wt) 80 µg - conv. | 16471 |  |  |  |
| PpLuc(wt) 80 µg - Jet | 27086 | 1.6 |  |  |
| mock | 1107 |  |  |  |

Thus, the modification of RNA and the administration of said modified RNA by jet injection act synergistically in increasing the expression of the protein encoded by the RNA (see Table 1).

In further experiments, it has been found that the additional increase of expression, which was achieved by jet injection using the modified RNA according to the invention (see Table 2 below; e.g. R1265, R2462, R1256, R2393), as compared to using an unmodified reference RNA (see Table 2; R2652), was achieved by using distinct modified RNAs, each comprising one or more of several distinct modifications. Table 2 shows the fold increase in protein expression achieved by administration of a given RNA (e.g. R1265) normalized to the protein expression achieved by administration of the respective RNA by conventional intradermal injection using a needle. For instance, the expression of modified RNA R1265 is increased by jet injection by a factor of 8.23 (as compared to the expression obatained after needle injection), whereas the expression of an unmodified reference RNA (R2652) is increased merely by a factor of 2.00. In this example, the expression increase achieved by modification of the RNA as described herein is 4-fold with respect to an unmodified reference RNA.

TABLE 2

Effect of jet injection using different modified RNAs

|  | Effect of jet injection |
|---|---|
| PpLuc(nat)-A30 R2652 | 2.00 |
| PpLuc(GC)-muag-A64-C30-HistoneSL R1265 | 8.23 |
| PpLuc(GC)-A64-C30-HistoneSL R2462 | 6.25 |
| PpLuc(GC)-muag-A64-C30 R1256 | 3.02 |
| PpLuc(nat)-muag-A64-C30-HistoneSL R2393 | 2.86 |

2. Induction of a Humoral Immune Response by the RAV-G mRNA Vaccine in Humans

Immunization

Preliminary results obtained in an ongoing clinical trial (phase I) demonstrate safety as well as efficacy of the vaccine according to the invention. In the clinical study, human volunteers were intradermally injected via jet injection using a Tropis device on day 0, 7 and 28 with the RAV-G mRNA vaccine R2403. The mRNA was prepared as described in Example 1 herein, i.e. mRNA complexed with protamine in a ratio of 2:1 (w/w) was mixed with an equal amount of free mRNA. On each of the three vaccination days, 80 μg of mRNA were administered.

In order to assess the safety profile of the vaccine according to the invention, subjects were monitored after administration (vital signs, vaccination site tolerability assessments, hematologic analysis after the second and third injection). The preliminary results obtained in the ongoing clinical study suggest that immunization with the mRNA according to the invention is well-tolerated in humans.

The efficacy of the immunization was analysed by determination of virus neutralizing titers (VNT) in sera from six subjects. To this end, blood samples were collected on day 0 as baseline and on day 42. Sera were analysed for virus neutralizing antibodies in the fluorescent antibody virus neutralisation (FAVN) test as described below.

Virus Neutralization Test

Detection of the virus neutralizing antibody response (specific B-cell immune response) was carried out by a virus neutralisation assay. The result of that assay is referred to as virus neutralization titer (VNT). According to WHO standards, an antibody titer is considered protective if the respective VNT is at least 0.5 IU/ml. The sera obtained as described above were used in a fluorescent antibody virus neutralisation (FAVN) test using the cell culture adapted challenge virus strain (CVS) of rabies virus as recommended by the OIE (World Organisation for Animal Health) and first described in Cliquet F., Aubert M. & Sagne L. (1998); J. Immunol. Methods, 212, 79-87. Shortly, heat inactivated sera will be tested as quadruplicates in serial two-fold dilutions as quadruplicates for their potential to neutralise 100 $TCID_{50}$ (tissue culture infectious doses 50%) of CVS in 50 l of volume. Therefore sera dilutions are incubated with virus for 1 hour at 37° C. (in humid incubator with 5% $CO_2$) and subsequently trypsinized BHK-21 cells are added ($4 \times 10^5$ cells/ml; 50 1 per well). Infected cell cultures are incubated for 48 hours in humid incubator at 37° C. and 5% $CO_2$. Infection of cells is analysed after fixation of cells using 80% acetone at room temperature using FITC anti-rabies conjugate. Plates were washed twice using PBS and excess of PBS was removed. Cell cultures are scored positive or negative for the presence of rabies virus. Negative scored cells in sera treated wells represent neutralization of rabies virus. Each FAVN tests includes WHO or OIE standard serum (positive reference serum) that serves as reference for standardisation of the assay. Neutralization activity of test sera is calculated with reference to the standard serum provided by the WHO and displayed as International Units/ml (IU/ml). The results are summarized in Table 3.

Results:

TABLE 3

Virus neutralizing titers after immunization of human subjects

| Subject no. | Virus neutralizing titer (VNT; IU/ml) |
|---|---|
| 1 | 4.0 |
| 2 | 0.7 |
| 3 | 0.2 |
| 4 | 0.7 |

TABLE 3-continued

Virus neutralizing titers after immunization of human subjects

| Subject no. | Virus neutralizing titer (VNT; IU/ml) |
|---|---|
| 5 | 1.4 |
| 6 | 0.5 |

In five out of six subjects (subject no. 1, 2, 4, 5 and 6), a virus neutralizing titer of at least 0.5 IU/ml was detected on day 42. According to the WHO standard, a protective antibody response has thus been achieved in these subjects, demonstrating the efficacy of the immunization with the mRNA according to the invention.

Conclusion:

According to preliminary results from the ongoing clinical trial, the use of the mRNA according to the invention for immunization of human subjects has a favourable safety profile. The efficacy of the approach has been demonstrated by these preliminary studies with a protective antibody response (VNT≥0.5 IU/ml) achieved on day 42 in five out of six investigated subjects.

3. Expression of EPO In Vivo

In order to determine erythropoetin expression in vivo, guinea pigs were intradermally injected with naked mRNA either by conventional needle injection or by jet injection (3 animals per group, each receiving 3 injections of 80 ag of RNA per injection site). After 24 hours, blood was sampled from the saphenous vein. Erythropoetin levels in serum were determined by ELISA (Mouse Erythropoetin Quantikine ELISA Kit, R&D Systems).

Results: Expression of EPO encoded by a modified mRNA (HSD17B4-EPO(GC)-albumin7-A64-C30-histoneSL (R3135)) is strongly enhanced in guinea pigs by jet injection compared to conventional intradermal needle injection (see FIG. 13).

Unexpectedly, expression of EPO from a modified mRNA (HSD17B4-EPO(GC)-albumin7-A64-C30-histoneSL (R3135)) is significantly more enhanced by jet injection than the expression of EPO from an unmodified reference mRNA (EPO(wt)-A30 (R3513)) (see FIG. 13).

4. Comparison of Conventional and Jet Injection of the RSV-F mRNA Vaccine for the Induction of a Humoral Immune Response in Guinea Pigs Preparation of DNA and mRNA Constructs:

For the present Examples, DNA sequences encoding the RSV-F protein of the RSV long strain (ATCC VR-26) were prepared and used for subsequent in vitro transcription reactions.

Fusion protein F of the RSV strain ATCC VR-26 long (Amino acid sequence according to SEQ ID No. 63):

```
MELPILKANA ITTILAAVTF CFASSQNITE EFYQSTCSAV

SKGYLSALRT GWYTSVITIE LSNIKENKCN GTDAKVKLIN

QELDKYKNAV TELQLLMQST TAANNRARRE LPRFMNYTLN

NTKKTNVTLS KKRKRRFLGF LLGVGSAIAS GIAVSKVLHL

EGEVNKIKSA LLSTNKAVVS LSNGVSVLTS KVLDLKNYID
```

-continued

```
KQLLPIVNKQ SCRISNIETV IEFQQKNNRL LEITREFSVN

AGVTTPVSTY MLTNSELLSL INDMPITNDQ KKLMSNNVQI

VRQQSYSIMS IIKEEVLAYV VQLPLYGVID TPCWKLHTSP

LCTTNTKEGS NICLTRTDRG WYCDNAGSVS FFPQAETCKV

QSNRVFCDTM NSLTLPSEVN LCNVDIFNPK YDCKIMTSKT

DVSSSVITSL GAIVSCYGKT KCTASNKNRG IIKTFSNGCD

YVSNKGVDTV SVGNTLYYVN KQEGKSLYVK GEPIINFYDP

LVFPSDEFDA SISQVNEKIN QSLAFIRKSD ELLHHVNAGK

STTNIMITTI IIVIIVILLS LIAVGLLLYC KARSTPVTLS

KDQLSGINNI AFSN
```

According to a first preparation, the DNA sequences encoding the above mentioned mRNAs were prepared. The DNA construct encoding RNA sequence R2510 (SEQ ID NO: 64) was prepared by introducing a 5'-TOP-UTR derived from the ribosomal protein 32 L according to SEQ ID No. 55, modifying the wild type coding sequence by introducing a GC-optimized sequence for stabilization, followed by a stabilizing sequence derived from the albumin-3'-UTR (albumin7 according to SEQ ID No. 58), a stretch of 64 adenosines (poly(A)-sequence), a stretch of 30 cytosines (poly(C)-sequence), and a histone stem loop according to SEQ ID No. 44. In FIG. 14 the sequence of the corresponding mRNA (R2510; SEQ ID NO: 64) is shown.

In Vitro Transcription:

The respective DNA plasmids prepared according to paragraph 1 were transcribed in vitro using T7 polymerase in the presence of a CAP analog (m⁷GpppG). Subsequently the mRNA was purified using PureMessenger® (CureVac, Tübingen, Germany; WO2008/077592A1).

Reagents:

Complexation Reagent: protamine

Preparation of the Vaccine:

The mRNA was complexed with protamine by addition of protamine to the mRNA in the ratio (1:2) (w/w) (adjuvant component). After incubation for 10 minutes, the same amount of free mRNA used as antigen-providing RNA was added.

RSV-F long vaccine (R2510): comprising an adjuvant component consisting of mRNA coding for RSV F protein long (R2510) according to SEQ ID NO. 63 complexed with protamine in a ratio of 2:1 (w/w) and the antigen-providing free mRNA coding for RSV F protein long (R2510) according to SEQ ID NO. 63 (ratio 1:1; complexed RNA:free RNA).

Immunization

On day zero, female guinea pigs (n=8/group) were intradermally (i.d.) injected with the RSV-F mRNA vaccine as described above (80 ag of R2510/mouse/vaccination day) either 1×100 al with conventional needle injection (i.d.), 4×25 µl with needle injection (i.d.), or 1×100 µl with jet injection (i.d.) as shown in Table 4. A control group (n=2) was needle-injected intramuscularly (i.m.) with 20 ag of inactivated RSV long (2×50 al). The inactivated "Respiratory Syncytial Virus Antigen" (inactivated RSV long) was purchased from the INSTITUT VIRION/SERION GmbH-SERION IMMUNDIAGNOSTICA GmbH. The inactivated virus was diluted in sterile PBS, so that a final concentration of 0.2 ag/L was achieved. All animals received boost injections on days 14 and 28. Blood samples were collected on day −3 (three days before the first vaccination) and on days 7, 21 and 42 for the determination of anti-RSV F antibody titers.

TABLE 4

Animal groups

| Group | Strain sex | No. mice | Volume route | Vaccine dose | Vaccination day | Bleeding day |
|---|---|---|---|---|---|---|
| 1 | Guinea Pigs, female | 8 | 1 × 100 µl, i.d., conventional | R2510 80 µg | 0, 14, 28 | −3, 7, 21, 42 |
| 2 | Guinea Pigs, female | 8 | 4 × 25 µl, i.d., conventional | R2510 80 µg | 0, 14, 28 | −3, 7, 21, 42 |
| 3 | Guinea Pigs, female | 8 | 1 × 100 µl, i.d., jet injection | R2510 80 µg | 0, 14, 28 | −3, 7, 21, 42 |
| 4 | Guinea Pigs, female | 2 | 2 × 50 µl, i.m., conventional | Inactivated RSV long 20 µg | 0, 14, 28 | −3, 7, 21, 42 |

Determination of Anti-RSV F Protein Antibodies by ELISA

ELISA plates were coated with inactivated RSV-LONG (Virion/Serion, final concentration 5 ag/mL) (Sino Biological Inc.). Coated plates were incubated with guinea pig serum using indicated dilutions (1:50 to 1:3906250 in 5× dilution steps) and binding of specific antibodies to the F protein was detected using biotinylated isotype specific anti-guinea pig IgG and IgG2a antibodies in combination with streptavidin-HRP (horse radish peroxidase) with 2,2'-Azinobis [3-ethylbenzothiazoline-6-sulfonic acid]-diammonium salt (ABTS) substrate.

RSV Neutralizing Antibody Titers (VNTs)

Sera were analysed by determining virus neutralization titers (VNTs). Briefly, sera samples were diluted 1:10 with Eagle's Minimum Essential Medium (EMEM), heat inactivated and serially diluted further 1:4. Diluted sera samples were incubated with RSV (25-50 PFU) for one hour at room temperature and inoculated in duplicates onto confluent HEp-2 cell monolayers in 24 well plates. After one hour incubation at 37° C. in a 5% $CO_2$ incubator, the wells were overlayed with 0.75% Methylcellulose medium. After 4 days of incubation, the overlay was removed and the cells were fixed with 0.1% crystal violet stain for one hour and then rinsed and air dried. The corresponding reciprocal neutralizing antibody titers were determined at the 60% reduction end-point of the virus control.

Results

As shown in FIG. 15, the RSV-F mRNA vaccine already induced anti-F protein antibodies of the IgG1 subclass (A) and the IgG2a subclass (B) on day 21 (one week after the first boost vaccination on day 14) when the vaccine was administered by jet injection (1×100 al). Comparable antibody titers were only reached on day 42 (two weeks after the second boost vaccination on day 28) when the vaccine was administered by conventional needle injection (4×25 µl). Thus the RSV-F mRNA vaccine administered by jet injection induced a humoral immune response against the RSV-F protein with a faster kinetic compared to administration by conventional needle injection.

As shown in FIG. 16, significant RSV neutralization titers were only measured on day 42 when the vaccine was administered by jet injection (100 al). Thus the vaccination with jet injection leads to a faster onset of immune responses than conventional needle injection.

The invention claimed is:

1. A method for enhancing the localized expression of an RNA-encoded polypeptide in an organism, the method comprising administering by jet injection a modified RNA in the dermis or muscle of a mammal, wherein the modified RNA comprises a polypeptide coding region, wherein the polypeptide coding region of the modified RNA encodes a polypeptide antigen, wherein the polypeptide coding region has an increased G/C content as compared with the G/C content of a corresponding polypeptide coding region of a native RNA, wherein the polypeptide sequence encoded by the modified RNA is not altered compared with the polypeptide sequence encoded by the native RNA, thereby enhancing the localized expression of the polypeptide antigen within the organism.

2. The method of claim 1, wherein the RNA is an mRNA and comprises a 5' cap.

3. The method of claim 2, wherein the mRNA sequence further comprises a stabilizing sequence from the alpha globin 3' UTR, positioned 3' relative to the coding region of the mRNA sequence.

4. The method of claim 2, wherein the mRNA sequence comprises from 5' to 3': a 5'-cap structure, a 5' UTR sequence, the sequence encoding the polypeptide, a 3' UTR, a poly(A) sequence, a poly(C) sequence, and a histone stem-loop sequence.

5. The method of claim 1, wherein the RNA further comprises at least one further modification selected from the group consisting of codon optimization, UTR modification, Poly(A) tail with more than 30 adenosine nucleotides, Poly(C) sequence, 5'-CAP structure except of m7GpppN, histone-stem-loop sequence, a base modification, and a chemically modified nucleotide.

6. The method of claim 5, wherein the at least one further modification is a chemically modified ARCA-CAP.

7. The method of claim 6, wherein the ARCA-CAP is modified with phosphorothioate.

8. The method of claim 5, wherein the at least one further modification comprises a base modification selected from the group consisting of 2-amino-6-chloropurineriboside-5'-triphosphate, 2-aminopurine-riboside-5'-triphosphate; 2-aminoadenosine-5'-triphosphate, 2'-amino-2'-deoxycytidine-triphosphate, 2-thiocytidine-5'-triphosphate, 2-thiouridine-5'-triphosphate, 2'-fluorothymidine-5'-triphosphate, 2'-O-methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-bromo-2'-deoxycytidine-5'-triphosphate, 5-bromo-2'-deoxyuridine-5'-triphosphate, 5-iodocytidine-5'-triphosphate, 5-iodo-2'-deoxycytidine-5'-triphosphate, 5-iodouridine-5'-triphosphate, 5-iodo-2'-deoxyuridine-5'-triphosphate, 5-methylcytidine-5'-triphosphate, 5-methyluridine-5'-triphosphate, 5-propynyl-2'-deoxycytidine-5'-triphosphate, 5-propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, puromycin-5'-triphosphate, and xanthosine-5'-triphosphate.

9. The method of claim 5, wherein the histone stem-loop comprises a nucleic acid sequence according to SEQ ID NO: 44.

10. The method of claim 1, wherein the RNA is complexed with a cationic or polycationic compound.

11. The method of claim 10, wherein the cationic or polycationic compound is protamine, poly-L-lysine (PLL), or poly-arginine.

12. The method of claim 10, wherein the RNA is complexed with a cationic or polycationic lipid.

13. The method of claim 1, wherein the RNA is administered intradermally.

14. The method of claim 1, wherein the RNA is administered intramuscularly.

15. The method of claim 1, wherein the RNA is administered subcutaneously.

16. The method of claim 1, wherein the polypeptide antigen is a Influenza virus antigen, a respiratory syncytial virus (RSV) antigen, a Herpes simplex virus (HSV) antigen, a human Papilloma virus (HPV) antigen, a Human immunodeficiency virus (HIV) antigen, a *Plasmodium* antigen, a *Staphylococcus aureus* antigen, a Dengue virus antigen, a *Chlamydia trachomatis* antigen, a Cytomegalovirus (CMV) antigen, a Hepatitis B virus (HBV) antigen, a *Mycobacterium tuberculosis* antigen, a Rabies virus antigen, or a Yellow Fever Virus antigen.

17. The method of claim 1, wherein the polypeptide antigen is a tumor antigen.

18. The method of claim 1, wherein the mammal is a human subject.

19. The method of claim 1, wherein the immune response is a humoral immune response.

20. The method of claim 1, further comprising administering an adjuvant to the organism.

* * * * *